US009750793B2

(12) United States Patent
Dharmasena et al.

(10) Patent No.: US 9,750,793 B2
(45) Date of Patent: Sep. 5, 2017

(54) MULTIFUNCTIONAL ORAL VACCINE BASED ON CHROMOSOME RECOMBINEERING

(71) Applicant: The United States of America, as represented by the Secretary, Dept. of Health and Human Services, Washington, DC (US)

(72) Inventors: Madushini Nirosha Dharmasena, Germantown, MD (US); Dennis J. Kopecko, Silver Spring, MD (US)

(73) Assignee: The United States of America, as Represented by the Secretary, Department of Health and Human Services, Washington, DC (US)

( * ) Notice: Subject to any disclaimer, the term of this patent is extended or adjusted under 35 U.S.C. 154(b) by 0 days.

(21) Appl. No.: 14/428,870

(22) PCT Filed: Sep. 16, 2013

(86) PCT No.: PCT/US2013/059980
§ 371 (c)(1),
(2) Date: Mar. 17, 2015

(87) PCT Pub. No.: WO2014/043637
PCT Pub. Date: Mar. 20, 2014

(65) Prior Publication Data

US 2015/0238591 A1 Aug. 27, 2015

Related U.S. Application Data

(60) Provisional application No. 61/701,939, filed on Sep. 17, 2012.

(51) Int. Cl.

| | |
|---|---|
| ***A61K 39/112*** | (2006.01) |
| ***C07H 21/02*** | (2006.01) |
| ***A61K 39/00*** | (2006.01) |
| ***C07K 14/25*** | (2006.01) |
| ***C07K 14/255*** | (2006.01) |
| ***C12N 1/20*** | (2006.01) |

(52) U.S. Cl.
CPC ...... *A61K 39/0283* (2013.01); *A61K 39/0275* (2013.01); *C07K 14/25* (2013.01); *C07K 14/255* (2013.01); *C12N 1/20* (2013.01); *A61K 2039/522* (2013.01); *A61K 2039/523* (2013.01); *A61K 2039/542* (2013.01); *A61K 2039/70* (2013.01); *C07K 2319/40* (2013.01)

(58) Field of Classification Search
CPC . A61K 39/02; A61K 39/0275; A61K 39/0283
USPC ................................ 424/184.1, 185.1, 234.1
See application file for complete search history.

(56) References Cited

U.S. PATENT DOCUMENTS

| | | | | |
|---|---|---|---|---|
| 7,541,043 | B2 * | 6/2009 | Kopecko ............ | A61K 39/0283 424/258.1 |
| 2012/0040433 | A1 | 2/2012 | Kopecko et al. | |
| 2012/0058142 | A1 | 3/2012 | Kopecko et al. | |

OTHER PUBLICATIONS

Black et al. (1987) The Journal of infectious diseases 155(6):1260-1265 "Prevention of Shigellosis by a *Salmonella typhi-Shigella sonnei* Bivalent Vaccine".

Cherepanov et al. (1994) Gene 158:9-14 "Gene disruption in *Escherichia coli*: $Tc^R$ and $Km^R$ cassettes with the option of Flp-catalyzed excision of the antibiotic-resistance determinant".

Churchward et al. (1984) Gene 31:165-171 "A pSC101-derived plasmid which shows no sequence homology to other commonly used cloning vectors".

D'Amelio et al. (1988) Infection and Immunity 56(10):2731-2735 "Comparative Analysis of Immunological Responses to Oral (Ty21a) and Parenteral (TAB) Typhoid Vaccines".

Datsenko et al. (2000) PNAS 97(12): 6640-6645 "One-step inactivation of chromosomal genes in *Escherichia coli* K-12 using PCR products".

Dharmasena et al. (2013) International Journal of Medical Microbiology 303:105-113 "Stable expression of *Shigella sonnei* form I O-polysaccharide genes recombineered into the chromosome of live *Salmonella* oral vaccine vector Ty21a".

DuPont et al. (1972) The Journal of Infectious Diseases 125(1):5-11 "Immunity in Shigellosis. I. Response of Man to Attenuated Strains of *Shigella*".

DuPont et al. (1972) The Journal of Infectious Diseases 125(1):12-16 "Immunity in Shigellosis. II. Protection Induced by Oral Live Vaccine or Primary Infection".

Formal et al. (1981) Infection and Immunity 34(3):746-750 "Construction of a Potential Bivalent Vaccine Strain: Introduction of *Shigella sonnei* Form I Antigen Genes into the *galE Salmonella typhi* Ty21a Typhoid Vaccine Strain".

Germanier et al. (1975) The Journal of Infectious Diseases 131(5):553-558 "Isolation and Characterization of *Gal* E Mutant Ty 21a of *Salmonella typhi*: A Candidate Strain for a Live, Oral Typhoid Vaccine".

Herrington et al. (1990) Vaccine 8:353-357 "Studies in volunteers to evaluate candidate *Shigella* vaccines: further experience with a bivalent *Salmonella typhi-Shigella sonnei* vaccine and protection conferred by previous *Shigella sonnei* disease".

Kopecko et al. (1980) Infection and Immunity 29(1):207-214 "Genetic and Physical Evidence for Plasmid Control of *Shigella sonnei* Form I Cell Surface Antigen".

Kopecko et al. (2009) International Journal of Medical Microbiology 299:233-246 "Genetic stability of vaccine strain *Salmonella* Typhi Ty21a over 25 years".

Kotloff et al. (1999) Bulletin of the World Health Organization 77(8):651-666 "Global burden of *Shigella* infections: implications for vaccine development and implementation of control strategies".

Mead et al. (1999) Emerging Infectious Diseases 5(5):607-625 "Food-Related Illness and Death in the United States".

(Continued)

*Primary Examiner* — Rodney P Swartz
(74) *Attorney, Agent, or Firm* — Klarquist Sparkman, LLP

(57) ABSTRACT

A recombineered *Salmonella typhi* Ty21a, compositions and vaccines comprising such a Ty21a, and a method for recombineering comprising inserting a large antigenic region into a bacterial chromosome for the purpose of making multivalent vaccines to protect against one or more disease agents are described herein.

22 Claims, 13 Drawing Sheets

(56) References Cited

OTHER PUBLICATIONS

Murphy, K. C. (1998) Journal of Bacteriology 180(8):2063-2071 "Use of Bacteriophage λ Recombination Functions to Promote Gene Replacement in *Escherichia coli*".
NCBI (Jul. 29, 2002) GenBank accession No. AF294823.
NCBI (Aug. 8, 2007) GenBank accession No. AY585348.
NCBI (Jan. 18, 2012) GenBank accession No. JN639000.
Noriega et al. (1999) Infection and Immunity 67:782-788 "Strategy for Cross-Protection among *Shigella flexneri* Serotypes".
Ohtake et al. (2011) Vaccine 29:2761-2771 "Room temperature stabilization of oral, live attenuated *Salmonella enterica* serovar Typhi-vectored vaccines".
Osorio et al.. (2009) Infection and Immunity 77(4):1475-1482 "Anthrax Protective Antigen Delivered by *Salmonella enterica* Serovar Typhi Ty21a Protects Mice from a Lethal Anthrax Spore Challenge".
Putthasri et al. (2009) Emerging Infectious Diseases 15(3):423-432 "Capacity of Thailand to Contain an Emerging Influenza Pandemic".
Sawitzke et al. (2007) Methods in Enzymology 421: 171-199 "Recombineering: In Vivo Genetic Engineering in *E. coli, S. enterica*, and Beyond".
Seid et al. (1984) The Journal of Biological Chemistry 259(14); 9028-9034 "Unusual Lipopolysaccharide Antigens of a *Salmonella typhi* Oral Vaccine Strain Expressing the *Shigella sonnei* Form I Antigen*".
Uzzau et al. (2001) PNAS 98(26):15264-15269 "Epitope tagging of chromosomal genes in *Salmonella*".
Van de Verg et al. (1990) Infection and Immunity 58, 2002-2004.
World Health Organization (2005) "Guidelines for the control of shigellosis, including epidemics due to Shigella dysenteriae type 1".
Xu et al. (2002) Infection and Immunity 70(8):4414-4423 "Molecular Cloning and Characterization of Genes for *Shigella sonnei* Form I O Polysaccharide: Proposed Biosynthetic Pathway and Stable Expression in a Live *Salmonella* Vaccine Vector".
Xu et al. (2007) Vaccine 25:6167-6175 "Core-linked LPS expression of *Shigella dysenteriae* serotype 1 O-antigen in live *Salmonella* Typhi vaccine vector Ty21a: Preclinical evidence of immunogenicity and protection".
Yu et al. (2011) Appl. Microbiol Biotechnol 91:177-188 "A method to generate recombinant *Salmonella typhi* Ty21a strains expressing multiple heterologous genes using an improved recombineering strategy".
Baron et al. (1987) Infection and Immunity 55(11):2797-2801 "Introduction of *Shigella flexneri* 2a Type and Group Antigen Genes into Oral Typhoid Vaccine Strain *Salmonella typhi* Ty21a".
Bumann et al. (2000) FEMS Immunology and Medical Microbiology 27:357-364 "Recombinant live *Salmonella* spp. for human vaccination against heterologous pathogens".
Cárdenas et al. (1993) Vaccine 11(2): 126-135 "Stability, immunogenicity and expression of foreign antigens in bacterial vaccine vectors".
Dharmasena et al. (2012) Amer. Soc. Microbiology $112^{th}$ General Meeting "Progress Towards Development of a Multivalent Typhoid-Shigella Oral Vaccine".
EP Partial Search Report for EP Application No. 13836396.5 dated Mar. 11, 2016.
Hone et al. (1988) Microbial Pathogenesis 5:407-418 "A chromosomal integration system for stabilization of heterologous genes in *Salmonella* based vaccine strains".

* cited by examiner

Anti-*S. flexneri 3a*

*FIG. 13*
Ty21a
Ty21a p2a
Ty21a p3a
Ty21a-Y
Ty21a-2a
Ty21a-3a
Ty21a-2al

Anti-*S. flexneri 2a*

MULTIFUNCTIONAL ORAL VACCINE BASED ON CHROMOSOME RECOMBINEERING

RELATED APPLICATION DATA

This application is a 35 U.S.C. §371 national phase application of PCT/US2013/059980, filed on Sep. 16, 2013, entitled "MULTIFUNCTIONAL ORAL VACCINE BASED ON CHROMOSOME RECOMBINEERING", which application claims the priority benefit of U.S. Provisional Application No. 61/701,939, filed Sep. 17, 2012, entitled "MULTIFUNCTIONAL ORAL VACCINE BASED ON CHROMOSOME RECOMBINEERING", all of which are incorporated herein by reference in their entirety. Each of the applications and patents cited in this text, as well as each document or reference cited in each of the applications and patents (including during the prosecution of each issued patent; "application cited documents"), and each of the PCT and foreign applications or patents corresponding to and/or claiming priority from any of these applications and patents, and each of the documents cited or referenced in each of the application cited documents, are hereby expressly incorporated herein by reference and may be employed in the practice of the invention. More generally, documents or references are cited in this text, either in a Reference List before the claims, or in the text itself; and, each of these documents or references ("herein cited references"), as well as each document or reference cited in each of the herein cited references (including any manufacturer's specifications, instructions, etc.), is hereby expressly incorporated herein by reference.

STATEMENT OF GOVERNMENT INTEREST

The instant application was made with government support; the government has certain rights in this invention.

SEQUENCE LISTING DATA

The Sequence Listing text file attached hereto, created Sep. 12, 2013, size 144 kilobytes, filename "6137FDA9PCT_SEQ_Listing_20130912_ST25.txt" is incorporated herein by reference in its entirety.

BACKGROUND

Bacillary dysentery and enteric fevers continue to be important causes of morbidity in both developed and developing nations. *Shigella* cause an estimated >150 million cases of dysentery, and enteric fever occurs in >27 million people, annually (Bardhan, et al. (2010) *Emerging Infec Diseases* 16:1718-1723; Crump, et al. (2004) *Bulletin of the WHO* 82:346-353; Crump and Mintz (2010) *Clin Infec Diseases* 50:241-246; WHO (2005) *Guidelines for the control of shigellosis* . . . ). Shigellosis and enteric fevers together cause >250,000 deaths annually (Bardhan, et al. (2010) *Emerging Infec Diseases* 16:1718-1723; Crump, et al. (2004) *Bulletin of the WHO* 82:346-353), demonstrating a continuing need for a multi-valent vaccine for protection against these diseases. Importantly, two thirds of all *Shigella* cases occur in children under the age of five years (Kotloff et al. (1999) *Bull. WHO,* 77:651-666; Kweon (2008) *Curr. Opin. Infect. Dis.,* 21:313-318), and enteric fevers are most common in young school-age children (Crump and Mintz (2010) *Clin Infec Diseases* 50:241-246).

The genus *Shigella* includes four species; *S. dysenteriae, S. flexneri, S. boydii* and *S. sonnei*, also designated as serogroups A, B, C and D, respectively. The first three species, respectively, are further divided into serotypes based upon differences in LPS structures. Upon ingestion of contaminated food or water, *Shigella* cause an acute invasive infection of the large intestine that typically results in severe abdominal cramps, fever, and dysentery (i.e., small volume <5 ml stools comprised of mucus, polymorphonuclear neutrophils, necrotic tissue, and streaks of blood). *S. boydii* and *S. sonnei* oftentimes cause a milder disease when compared to *S. dysenteriae* and *S. flexneri*. *S. flexneri* is responsible for most endemic infections in developing countries. *S. sonnei* is the species responsible for most endemic infections observed in industrialized countries. The US CDC estimates an incidence of ~450,000 cases of *S. sonnei* disease in the US each year, which occurs mostly in child daycare facilities. *S. sonnei* is also responsible for a considerable amount of morbidity in developing countries such as Thailand, where it is the cause of ~95% of shigellosis (Mead et al. (1999) *Emerg. Infect. Dis.,* 5:607-625; Putthasri et al. (2009) *Emerg. Infect. Dis.,* 15:423-432). *S. dysenteriae* serotype 1 (Sd1) is especially important, as it causes severe dysentery plus hemolytic uremic syndrome (as a result of producing the potent cytotoxin Shiga toxin), typically resulting in a higher mortality rate than infections due to other *Shigella* species. Furthermore, Sd1 classically causes large epidemics with high attack rates (World Health Organization (2005) *Guidelines for the Control of Shigellosis, Including Epidemics Due to Shigella dysenteriae Type* 1, ISBN 924159330X).

Currently, there is no licensed vaccine available to prevent the occurrence of shigellosis. Increasing multiple antibiotic resistance in *Shigella* commonly thwarts local therapies. As a result, the World Health Organization considers development of a vaccine against shigellosis a top priority. Most importantly, there is a global public health need for a vaccine to prevent shigellosis in endemic populations, travelers, and the military. Due to the existence of a large number of *Shigella* serotypes (>40), some investigators have attempted to find surface antigens common to most serotypes (Kaminski et al. (2009) *Expert Rev. Vaccines,* 8:1693-1704). Despite significant efforts, common surface proteins by themselves (e.g., ipaA,B,C,D) do not appear to stimulate significant or sustained protective immunity to *Shigella* infection. However, there is considerable evidence that protective immunity is directed primarily against *Shigella* serotype specific LPS O-antigen, which highlights the importance of O-antigens as targets for vaccine development (Ferreccio et al. (1991) *Am. J. Epidemiol.,* 134:614-627; DuPont et al. (1972) *J. Infect. Dis.,* 125:5-11; DuPont et al. (1972) *J. Infect. Dis.,* 125:12-16).

Indeed, lipopolysaccharide (LPS) alone has been shown to be a potent vaccine antigen for specific protection against shigellosis. The plasmid cloning of heterologous LPS biosynthetic genes and the expression in Ty21a of either *S. sonnei* or of *S. dysenteriae* 1 LPS's have previously been reported. The resulting plasmids encoding *Shigella* LPSs were reasonably stable for more than 50 generations of growth in non-selective media, but they still contained an objectionable antibiotic resistance marker. The deletion of this antibiotic resistance marker resulted in significant plasmid instability.

Based upon specific *Shigella* serotype prevalence worldwide and previous studies of serotype cross-protection among Shigellae, Noriega, et al. (1999 *Infection and Immunity* 67:782-788) have suggested that a multivalent vaccine containing LPSs of *S. Sonnei, S. dysenteriae* 1, *S. flexneri* 2a, *S. flexneri* 3a, and *S. flexneri* 6 could protect against~85% of shigellosis worldwide.

The live, attenuated, oral vaccine *Salmonella enterica* serovar *Typhi* strain Ty21a has been utilized extensively as a broad-based oral vaccine vector for the expression of various foreign antigens (Xu et al. (2007) *Vaccine,* 25:6167-6175; Xu et al. (2002) *Infect. Immun.,* 70:4414-4423; Osorio et al. (2009) *Infect. Immun.,* 44:1475-1482). Ty21a is the only licensed, live, attenuated vaccine for protection against typhoid fever. Moreover, it has been safely administered to more than 200 million recipients around the world. As a whole-cell vaccine, Ty21a induces mucosal, humoral, and cellular immunity, leading to high-level, long-term protection (i.e., virtually undiminished protection at the end of 7 full years) against typhoid fever (Levine, et al. (1999) *Vaccine* 17 Suppl 2: S22-27) with considerable evidence of cross-protection against both *S. Paratyphi* A and B (Bardhan, et al. (2010) *Emerging Infec Diseases* 16:1718-1723; D'Amelio et al. (1988) *Infect. Immun.,* 56:2731-2735; Levine, et al. (2007) *Clin Infec Diseases* 45 Supp 1:S24-28; Schwartz, et al. (1990) *Archives Internal Med* 150:349-351; Wahid, et al. (2012) *Clin and Vaccine Immunol* CVI 19:825-834).

SUMMARY

In earlier vaccine efforts, the 180 kb form 1 O-antigen encoding plasmid of *S. sonnei* was transferred, as a proof-of-principle, as part of a large~300 kb plasmid cointegrate to the vaccine strain Ty21a. The resulting hybrid vaccine strain, 5076-1C, expressed both homologous *S. typhi* 9,12 O-antigen and heterologous *S. sonnei* O-antigen that were immunogenic (Seid et al. (1984) *J. Biol. Chem.,* 259:9028-9034; Formal et al. (1981) *Infect. Immun.,* 34:746-750). Importantly, oral immunization of volunteers with 5076-1C was safe and elicited significant protection against virulent *S. sonnei* oral challenge (i.e., 100% protection against severe dysentery) (Black et al. (1987) *J. Infect. Dis.,* 155:1260-1265; Herrington et al. (1990) *Vaccine,* 8:353-357; Van de Verg et al. (1990) *Infect. Immun.,* 58:2002-2004). Unfortunately, though not entirely unexpectedly, the considerable protection afforded volunteers receiving the first two lots of vaccine was not observed with subsequent vaccine lots, due to loss of the form I gene region from the genetically unstable, large cointegrate plasmid in 5076-1C (Formal et al. (1981) *Infect. Immun.,* 34:746-750). Thus, further molecular studies were carried out to stabilize the *S. sonnei* form I gene region in vaccine vector constructs. In these subsequent studies, the minimal size gene regions needed for stable expression of *S. sonnei* or *S. dysenteriae* serotype 1 O-antigens were determined to be between 11 and 15 kb (Xu et al. (2007) *Vaccine,* 25:6167-6175; Xu et al. (2002) *Infect. Immun.,* 70:4414-4423). These studies also revealed that the *S. sonnei* O-antigen could be expressed as core-linked LPS or as a Group 4 O-antigen capsule in either Ty21a or in *Shigella*, as are LPSs of certain other *Shigella* serotypes and of *Salmonella Typhi*, but that either form of O-antigen expression appears to be equally immunogenic.

These early *Shigella* LPS constructs were made in the low copy genetically stable plasmid pGB-2, which carries an antibiotic resistance marker for genetic utility. Removal of this antibiotic resistance marker to facilitate human vaccine use proved problematic, and resulted in unexplained lower plasmid genetic stability (i.e., the antibiotic resistant plasmid was stable during growth in the absence of antibiotic pressure for more than 60 generations, but removal of just the antibiotic resistance gene sequences somehow resulted in genetic instability).

Thus, a study was undertaken to address the issues of genetic stability and the need for a selectable, but removable antibiotic resistance marker. Towards this end, the previously described recombination techniques (Datsenko et al. (2000) *Proc. Natl. Acad. Sci. USA,* 97:6640-6645 were modified to recombineer a >11 kb *Shigella sonnei* O-antigen biosynthetic gene region into the *Salmonella Typhi* Ty21a chromosome to construct Ty21a-Ss (Ty21a expressing *S. sonnei* O-antigen). Further, this chromosomal integration of essential *S. sonnei* LPS biosynthetic genes was 100% genetically stable, even after removal of a selectable antibiotic resistance gene cassette. Heterologous *S. sonnei* form 1 LPS was stably expressed in Ty21a-Ss along with homologous *Salmonella Typhi* O-antigen. Of note, the candidate vaccine strain Ty21a-Ss elicited solid immune protection in mice against virulent *S. sonnei* challenge.

In one aspect, the invention provides a *Salmonella typhi* Ty21a comprising a *Shigella sonnei* O-antigen biosynthetic gene region inserted into the *Salmonella typhi* Ty21a chromosome, wherein: a) heterologous *Shigella sonnei* form 1 O-antigen is stably expressed together with or without homologous *Salmonella typhi* O-antigen; b) immune protection is elicited against virulent *Shigella sonnei* challenge; and c) immune protection is elicited against virulent *Salmonella Typhi* challenge. In another aspect, the invention provides a *Salmonella typhi* Ty21a comprising a *Shigella sonnei* O-antigen biosynthetic gene region inserted into the *Salmonella typhi* Ty21a chromosome, wherein: a) heterologous *Shigella sonnei* form 1 O-antigen is stably expressed together with homologous *Salmonella typhi* O-antigen; b) immune protection is elicited against virulent *Shigella sonnei* challenge; and c) immune protection is elicited against virulent *Salmonella Typhi* challenge.

In one embodiment of the invention, the region is encoded by a DNA sequence selected from the group consisting of: a) a DNA sequence as set out in SEQ ID NO:2; b) a DNA sequence that shares at least about 90% sequence identity with the DNA sequence set out in SEQ ID NO:2; and c) a DNA sequence that is a functional variant of the DNA sequence set out in SEQ ID NO:2. SEQ ID NO:2 is provided herein and has been submitted to GENBANK and designated JX436479 but will not be released until publication of a manuscript describing portions of this study. The sequence with accession number AF294823 (SEQ ID NO:23) actually contains about 19 ORFs and includes the IS elements. In the current study, only the essential 10 ORFs (out of the 19 ORFs displayed in AF294823 (SEQ ID NO:23)) were cloned and inserted into the Ty21a chromosome.

In a further embodiment of the invention, the Ty21a further comprises an O-antigen biosynthetic gene region from a bacterial strain selected from the group consisting of: *Shigella* species (*Shigella dysenteriae, Shigella flexneri*, and *Shigella boydii*), *Escherichia coli* serotypes, *Salmonella enterica* serovars, *Vibrio cholerae* serotypes, *Enterobacter* species, *Yersinia* species, and *Pseudomonas* species.

In another aspect, the invention provides a *Salmonella typhi* Ty21a comprising a *Shigella dysenteriae* 1 O-antigen biosynthetic gene region inserted into the *Salmonella typhi* Ty21a chromosome, wherein: a) heterologous *Shigella dysenteriae* serotype 1 O-antigen is stably expressed together with or without homologous *Salmonella typhi* O-antigen; b) immune protection is elicited against virulent *Shigella dysenteriae* 1 challenge; and c) immune protection is elicited against virulent *Salmonella Typhi* challenge. In still another aspect, the invention provides a *Salmonella typhi* Ty21a comprising a *Shigella dysenteriae* 1 O-antigen biosynthetic gene region inserted into the *Salmonella typhi* Ty21a chromosome, wherein: a) heterologous *Shigella dysenteriae* serotype 1 O-antigen is stably expressed together with homologous *Salmonella typhi* O-antigen; b) immune protection is elicited against virulent *Shigella dysenteriae* 1 challenge; and c) immune protection is elicited against virulent *Salmonella Typhi* challenge.

In one embodiment of the invention, the region is encoded by a DNA sequence selected from the group consisting of: a) a DNA sequence as set out in SEQ ID NOs:3 or 4; b) a DNA sequence that shares at least about 90% sequence identity with the DNA sequence set out in SEQ ID NO:3 or 4; and c) a DNA sequence that is a functional variant of the DNA sequence set out in SEQ ID NO:3 or 4.

In a preferred embodiment of the invention, the region is encoded by a DNA sequence selected from the group consisting of: a) a DNA sequence as set out in SEQ ID NO:33; b) a DNA sequence that shares at least about 90% sequence identity with the DNA sequence set out in SEQ ID NO:33; and c) a DNA sequence that is a functional variant of the DNA sequence set out in SEQ ID NO:33.

In still another embodiment of the invention, the Ty21a further comprises an O-antigen biosynthetic gene region from a bacterial strain selected from the group consisting of: *Shigella* species (*Shigella sonnei, Shigella flexneri*, and *Shigella boydii*), *Escherichia coli* serotypes, *Salmonella enterica* serovars, *Vibrio cholerae* serotypes, *Enterobacter* species, *Yersinia* species, and *Pseudomonas* species.

In another aspect, the invention provides a plasmid construct having i) a DNA sequence as set out in SEQ ID NO: 1 or ii) a DNA sequence that shares at least about 90% sequence identity with the DNA sequence set out in SEQ ID NO:1. In a further embodiment of the invention, the plasmid construct further comprises a *Shigella sonnei* O-antigen biosynthetic gene region. In still a further embodiment of the invention, the plasmid construct further comprises a *Shigella dysenteriae* 1 O-antigen biosynthetic gene region.

In another aspect, the invention provides a method of recombineering a large antigenic gene region into a bacterial chromosome, comprising: i) cloning the region into a vector containing: ia) a genetically selectable marker flanked 5' and 3' by an FRT site, respectively; ib) a multiple cloning site downstream of the 3' FRT site; and ic) two sites of chromosome homology, one of the two located upstream of the 5' FRT site, and one of the two located downstream of the multiple cloning site; ii) integrating the region into the bacterial chromosome using λ red recombination; iii) selecting for the genetically selectable marker; and iv) removing the selectable marker (e.g., gene), thus recombineering the region into the chromosome. In one embodiment of the inventive method, the genetically selectable marker is an antibiotic resistance marker. In another embodiment of the inventive method, the selectable marker is rendered non-functional (rather than removed). In another embodiment of the inventive method, the bacterial chromosome can be varied. In still another embodiment of the inventive method, the insertion site (within the chromosome) can be varied.

In yet another embodiment of the inventive method, the antigenic gene region is about 5 to about 20 kb long. In still another embodiment of the inventive method, the antigenic region is longer than 20 kb. In another embodiment of the inventive method, the vector is selected from the group consisting of a plasmid, phage, phasmid, and cosmid construct. In another embodiment, the plasmid construct is the above-disclosed plasmid construct having i) a DNA sequence as set out in SEQ ID NO: 1 or ii) a DNA sequence that shares at least about 90% sequence identity with the DNA sequence set out in SEQ ID NO:1.

In another embodiment of the inventive method, the bacterial chromosome is *Salmonella typhi* Ty21a. In still another embodiment of the inventive method, the antibiotic resistance marker is kanamycin. In still another embodiment of a method according to the invention, the antigenic region is a *Shigella sonnei* O-antigen biosynthetic gene region. In yet another embodiment of a method according to the invention, the antigenic region is a *Shigella dysenteriae* 1 O-antigen biosynthetic gene region. In yet another embodiment of a method according to the invention, the antigenic region is a *Shigella flexneri* 2a O-antigen biosynthetic gene region. In yet another embodiment of a method according to the invention, the antigenic region is a *Shigella flexneri* 3a O-antigen biosynthetic gene region.

In another embodiment, the inventive method is for use in a whole cell bacterial vaccine. In still another embodiment, the inventive method is for use in a live attenuated *Salmonella* strain, a *Shigella* strain, a *Listeria* strain, a *Yersinia* strain, an *Escherichia coli* strain, an Enterobacteriaceae strain, in a protozoan strain, or in another live vectored vaccine.

In still another embodiment of a method according to the invention, the region is engineered between about 500 to about 1000 bp regions of bacterial chromosome homology before step ii. In still another embodiment of a method according to the invention, the kanamycin resistance gene is removed via recombination induced following transformation with pCP20.

In one aspect, the invention provides a composition of matter comprising the herein-disclosed *Salmonella typhi* Ty21a in combination with a physiologically acceptable carrier.

In another aspect, the invention provides a vaccine comprising the herein-disclosed *Salmonella typhi* Ty21a in combination with a physiologically acceptable carrier.

In yet another aspect, the invention provides a method of preventing or treating at least one bacterial infection comprising administering a prophylactically or therapeutically effective amount of the herein-disclosed *Salmonella typhi* Ty21a to a subject, thus preventing or treating the at least one bacterial infection.

In another embodiment of the inventive *Salmonella typhi* Ty21a, the gene region is partially or wholly chemically synthesized.

In another embodiment of the inventive plasmid construct, the DNA sequence is partially or wholly chemically synthesized.

In one aspect, the invention provides the use of an O-antigen biosynthetic gene region in a bacterial strain designed to biologically manufacture protein-LPS conjugate products.

In an additional embodiment of the invention, the gene cluster responsible for the biosynthesis of the bacterial LPS, capsule polysaccharide (CPS), or oligo polysaccharides (oligo PS) is transformed into *E. coli* together with the protein carrier of interest along with an enzyme that performs the bioconjugation reaction in vivo. Once produced upon induction, simple purification steps are performed, and the biological products are formulated for use as a vaccine (Dro (2012) *Gen. Eng. Biotech. News*, Vol. 32, www.genengnews.com/gen-articles/developing-next-gen-conjugate-vaccines/4042; Gambillara (2012) *BioPharm Int.,* 25:28-32; Kowarik et al. (2006) *Science,* 314:1148-1150; Wacker et al. (2006) *Proc. Natl. Acad. Sci. USA,* 103:7088-

7093; Kowarik et al. (2006) *EMBO J.,* 25:1957-1966; Feldman et al. (2005) *Proc. Natl. Acad. Sci. USA,* 102:3016-3021; Nita-Lazar et al. (2005) *Glycobiology,* 15:361-367; Wacker et al. (2002) *Science,* 298:1790-1793; Wacker (2002) *N-linked Protein Glycosylation: From Eukaryotes to Bacteria*, Ph.D. thesis submitted to the Swiss Federal Institute of Technology, Zurich).

The methods according to the invention will, in additional embodiments, allow for the insertion of antigenic gene region(s) into other enteric bacteria, as well.

The *Salmonella* serovars *Typhi* and *Paratyphi* are acquired through ingestion of contaminated food and water and cause indistinguishable enteric fevers. Though peak incidence occurs in young school children, enteric fever affects all ages. Multiple antibiotic resistance complicates treatment and makes vaccination a desired priority in areas lacking proper sanitation. Although two typhoid vaccines are available, there has been little effort to introduce them on a large scale in the developing world. A multivalent vaccine that would simultaneously protect against enteric fevers and shigellosis would have great practical advantages in advancing immunization against these diseases, not only to travelers and the military, but also to the developing nations which suffer high resulting disease mortality.

In yet another aspect, the invention provides a *Salmonella typhi* Ty21a comprising a *Shigella flexneri* 2a O-antigen biosynthetic gene region inserted into the *Salmonella typhi* Ty21a chromosome, wherein: a) heterologous *Shigella flexneri* 2a O-antigen is stably expressed together with or without homologous *Salmonella typhi* O-antigen; b) immune protection is elicited against virulent *Shigella flexneri* 2a challenge; and c) immune protection is elicited against virulent *Salmonella typhi* challenge. In still another aspect, the invention provides a *Salmonella typhi* Ty21a comprising a *Shigella flexneri* 2a O-antigen biosynthetic gene region inserted into the *Salmonella typhi* Ty21a chromosome, wherein: a) heterologous *Shigella flexneri* 2a O-antigen is stably expressed together with homologous *Salmonella typhi* O-antigen; b) immune protection is elicited against virulent *Shigella flexneri* 2a challenge; and c) immune protection is elicited against virulent *Salmonella typhi* challenge.

In still another aspect, the invention provides a *Salmonella typhi* Ty21a comprising a *Shigella flexneri* 3a O-antigen biosynthetic gene region inserted into the *Salmonella typhi* Ty21a chromosome, wherein: a) heterologous *Shigella flexneri* 3a O-antigen is stably expressed together with or without homologous *Salmonella typhi* O-antigen; b) immune protection is elicited against virulent *Shigella flexneri* 3a challenge; and c) immune protection is elicited against virulent *Salmonella typhi* challenge. In yet another aspect, the invention provides a *Salmonella typhi* Ty21a comprising a *Shigella flexneri* 3a O-antigen biosynthetic gene region inserted into the *Salmonella typhi* Ty21a chromosome, wherein: a) heterologous *Shigella flexneri* 3a O-antigen is stably expressed together with homologous *Salmonella typhi* O-antigen; b) immune protection is elicited against virulent *Shigella flexneri* 3a challenge; and c) immune protection is elicited against virulent *Salmonella typhi* challenge.

Other aspects of the invention are described in or are obvious from the following disclosure and are within the ambit of the invention.

BRIEF DESCRIPTION OF THE DRAWINGS

The following Detailed Description, given by way of Examples, but not intended to limit the invention to specific embodiments described, may be understood in conjunction with the accompanying figures, in which:

FIG. 7A quantifies the IgG elicited against *S. dysenteriae* LPS. FIG. 7B quantifies the IgG elicited against *S. Typhi* 9,12 LPS.

DETAILED DESCRIPTION

Figure 1:
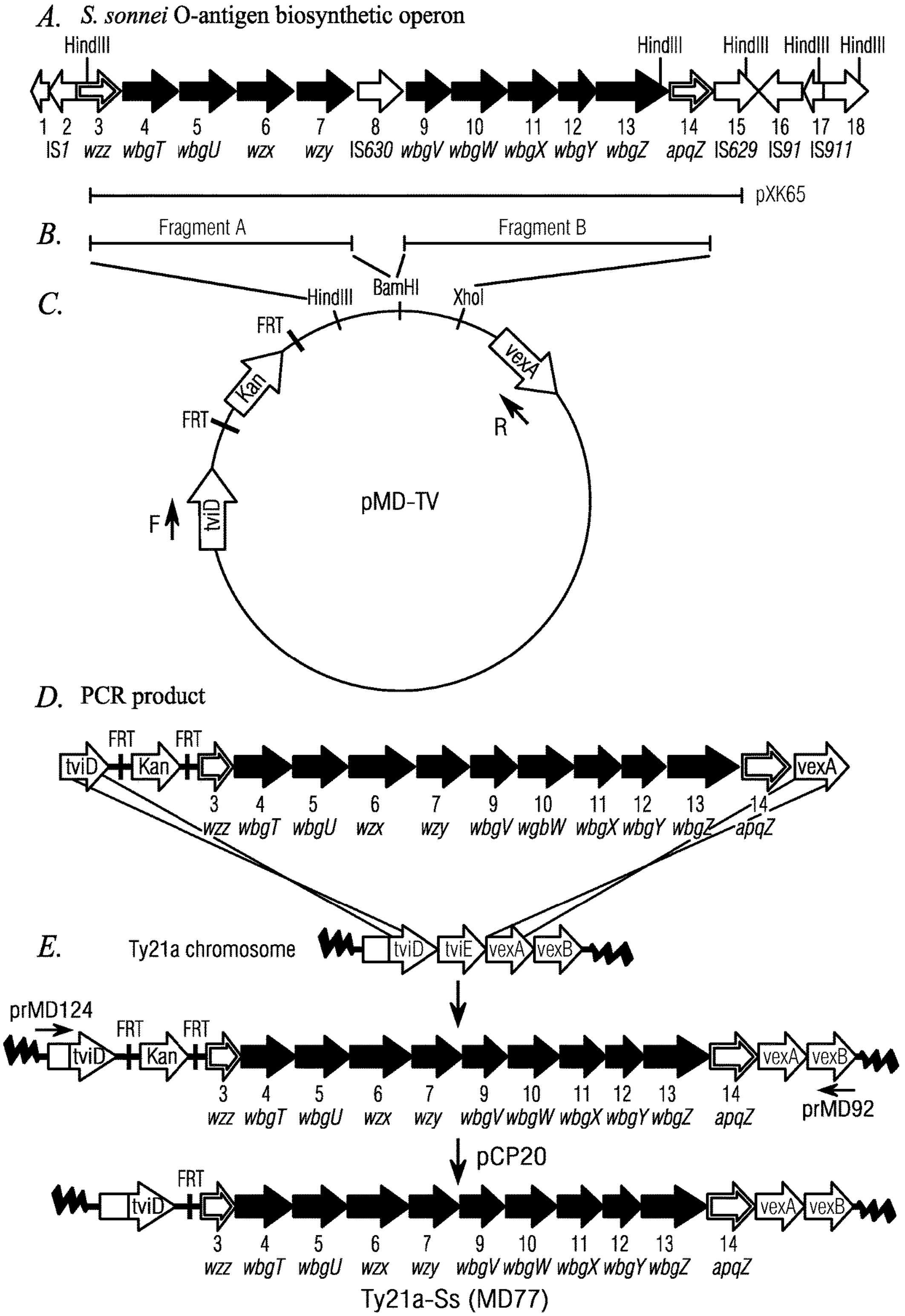
FIG. 1 provides a schematic representation of the cloning and chromosomal integration of *S. sonnei* form I LPS biosynthetic genes. Panel A shows the ORFs involved in form 1 O-antigen biosynthesis and adjacent IS elements from the cloned insert of pXK65, reported previously (Xu, et al. (2002) *Infect and immunity* 70:4414-4423). In Panel B, the latter part of wzz (orf3), containing the promoter of the O-antigen operon, through wzy(orf7) was PCR-amplified as fragment A and cloned into HindIII and BamHI sites of pMD-TV (SEQ ID NO:1). Next, the genes wbgV (orf9) through apqZ (orf14) were PCR-amplified as fragment B and cloned into the BamHI and XhoI sites adjacent to fragment A. In Panel C, the resulting plasmid pMD-TV-Ss-1, was used as a template to PCR-amplify tviD through vexA using forward (F) and reverse (R) primers. In Panel D, the PCR product was integrated into the tviD-tviE-vexA region of the Ty21a chromosome by λ red-mediated recombination. Finally, in Panel E, the $Kan^r$ cassette was removed following temporary introduction of the temperature-sensitive plasmid pCP20 by expression of FLP recombinase, generating the final antibiotic-sensitive, chromosomal integrant Ty21a-Ss (strain MD77).

In an effort to elucidate a method to insert the large >10 kb *S. sonnei* LPS gene region into the chromosome that would allow for removal of a selectable marker and would result in 100% genetic stability, an existing recombination method was optimized to mediate the insertion of a >11 kb region encoding the *S. sonnei* LPS genes into the Ty21a genome in a region that does affect normal cell metabolism. This chromosomal insert was shown to be 100% genetically stable. Further testing demonstrated that the resulting strain Ty21a-Ss simultaneously expresses both homologous Ty21a and heterologous *S. sonnei* O-antigens. Moreover, Ty21a-Ss elicited a strong dual anti-LPS serum immune response and 100% protection in mice against a virulent *S. sonnei* challenge. This new vaccine candidate, absolutely stable for vaccine manufacture, should provide combined protection against enteric fevers due to *Salmonella* serovar *Typhi* (and some *Paratyphi* infections) and against shigellosis due to *S. sonnei.*

Definitions

The terms "O-Ps (O polysaccharide) biosynthesis" and "O-antigen biosynthetic" genes are used interchangeably herein. The O-antigen is a polysaccharide that can be expressed as a core-linked lipopolysaccharide (LPS) or as a group 4 capsule where the O-antigen is expressed at the cell surface but linked to a lipid other than lipid A-core oligosaccharide.

The terms "vector" and "vehicle" are used interchangeably in reference to nucleic acid molecules that transfer DNA segment(s) from one cell to another. The term "expression vector" as used herein refers to a recombinant DNA molecule containing a desired coding sequence and appropriate nucleic acid sequences necessary for the expression (i.e., transcription and/or translation) of an operably linked coding sequence in a particular host organism. Expression vectors are exemplified by, but not limited to, plasmids, plasmid constructs, plasmids, phagemids, shuttle vectors, cosmids, viral vectors, the chromosome, mitochondrial DNA, plastid DNA, and nucleic acid fragments, that may be used for expression of a desired sequence in a cell, such as a human cell, avian cell, a fungal cell, a protozoan cell, and/or insect cell. Nucleic acid sequences used for expression in prokaryotes include a promoter, optionally an operator sequence, a ribosome-binding site and possibly other sequences. Eukaryotic cells are known to utilize promoters, enhancers, and termination and polyadenylation signals. Flippase Recognition Target (FRT) sites and multiple cloning sites (MCS), also called polylinkers, are also utilized. A MCS is a short DNA segment containing many (up to about 20) restriction sites that are typically unique, occurring only once within a given plasmid.

The term "transformation" as used herein, refers to any mechanism by which a DNA molecule (i.e., plasmid or PCR amplicon) may be incorporated into a host cell. A successful transformation results in the capability of the host cell to express any operative genes carried by the plasmid or incorporated into the chromosome. Transformations may result in genetically stable or transient gene expression. One example of a transient transformation comprises a plasmid vector within a cell, wherein the plasmid is not integrated into the host cell chromosome and is segregated from cells during cell division. Alternatively, a stable transformation comprises a plasmid within a cell, wherein the plasmid is integrated within the host cell genome or exists stably in the cytoplasm after many cell divisions.

The terms "subject", "patient", and "individual", as used herein, interchangeably refer to a multicellular animal (including mammals (e.g., humans, non-Human primates, murines, ovines, bovines, ruminants, lagomorphs, porcines, caprines, equines, canines, felines, ayes, etc.), avians (e.g., chicken), amphibians (e.g. *Xenopus*), reptiles, and insects (e.g. *Drosophila*). "Animal" includes guinea pig, hamster, ferret, chinchilla, mouse and cotton rat.

As is well known in this art, amino acid or nucleic acid sequences may be compared using any of a variety of algorithms, including those available in commercial computer programs such as BLASTN for nucleotide sequences and BLASTP, gapped BLAST®, and PSI-BLAST for amino acid sequences. Exemplary such programs are described in Altschul et al. (1990) *J. Mol. Biol.,* 215:403-410; Altschul, et al., Methods in Enzymology; Altschul et al. (1997) *Nucleic Acids Res.,* 25:3389-3402; Baxevanis, et al., Bioinformatics: A Practical Guide to the Analysis of Genes and Proteins, Wiley, 1998; and Misener, et al., (eds.), Bioinformatics Methods and Protocols (Methods in Molecular Biology, Vol. 132), Humana Press, 1999; all of which are incorporated herein by reference. In addition to identifying homologous sequences, the programs mentioned above typically provide an indication of the degree of homology.

The phrases "homology" or "substantial homology", as used herein, refers to a comparison between amino acid sequences. As will be appreciated by those of ordinary skill in the art, two sequences are generally considered to be "substantially homologous" if they contain homologous residues in corresponding positions. Homologous residues may be identical residues. Alternatively, homologous residues may be non-identical residues with appropriately similar structural and/or functional characteristics. For example, as is well known by those of ordinary skill in the art, certain amino acids are typically classified as "hydrophobic" or "hydrophilic" amino acids, and/or as having "polar" or "non-polar" side chains. Substitution of one amino acid for another of the same type may often be considered a "homologous" substitution.

In some embodiments, two sequences are considered to be substantially homologous if at least 50%, 55%, 60%, 65%, 70%, 75%, 80%, 85%, 90%, 91%, 92%, 93%, 94%, 95%, 96%, 97%, 98%, 99% or more of their corresponding residues are homologous over a relevant stretch of residues. In some embodiments, the relevant stretch is a complete sequence. In some embodiments, the relevant stretch is at least 10, 15, 20, 25, 30, 35, 40, 45, 50, 55, 60, 65, 70, 75, 80, 85, 90, 95, 100, 125, 150, 175, 200, 225, 250, 275, 300, 325, 350, 375, 400, 425, 450, 475, 500 or more residues.

The phrases "identity" or "substantial identity", as used herein, refer to a comparison between amino acid or nucleic acid sequences. As will be appreciated by those of ordinary skill in the art, two sequences are generally considered to be "substantially identical" if they contain identical residues in corresponding positions. Indeed, "identity" refers to the overall relatedness between polymeric molecules, e.g., between nucleic acid molecules (e.g., DNA molecules and/or RNA molecules) and/or between polypeptide molecules. Calculation of the percent identity of two nucleic acid sequences can, for example, be performed by aligning the two sequences for optimal comparison purposes (e.g., gaps can be introduced in stretches of one or both of a first and a second nucleic acid sequence for optimal alignment and non-identical sequences can be disregarded for comparison purposes). In certain embodiments, the length of a sequence aligned for comparison purposes is at least 30%, at least 40%, at least 50%, at least 60%, at least 70%, at least 80%, at least 90%, at least 95%, or substantially 100% of the length of the reference sequence. The nucleotides at corresponding nucleotide positions are then compared. When a position in the first sequence is occupied by the same nucleotide as the corresponding position in the second sequence, then the molecules are identical at that position. The percent identity between the two sequences is a function of the number of identical positions shared by the sequences, taking into account the number of gaps, and the length of each gap, which needs to be introduced for optimal alignment of the two sequences. The comparison of sequences and determination of percent identity between two sequences can be accomplished using a mathematical algorithm.

In some embodiments, two sequences are considered to be substantially identical if at least 50%, 55%, 60%, 65%, 70%, 75%, 80%, 85%, 90%, 91%, 92%, 93%, 94%, 95%, 96%, 97%, 98%, 99% or more of their corresponding residues are identical over a relevant stretch of residues. In some embodiments, the relevant stretch is a complete sequence. In some embodiments, the relevant stretch is at least 10, 15, 20, 25, 30, 35, 40, 45, 50, 55, 60, 65, 70, 75, 80, 85, 90, 95, 100, 125, 150, 175, 200, 225, 250, 275, 300, 325, 350, 375, 400, 425, 450, 475, 500 or more residues.

Reference herein to any numerical range (for example, a dosage range) expressly includes each numerical value (including fractional numbers and whole numbers) encompassed by that range. For example, but without limitation, reference herein to a range of "$2\times10^9$ to $5\times10^{10}$" CFU (colony-forming units) includes all whole numbers of and fractional numbers between the two. In a further illustration, reference herein to a range of "less than x" (wherein x is a specific number) includes whole numbers x−1, x−2, x−3, x−4, x−5, x−6, etc., and fractional numbers x−0.1, x−0.2, x−0.3, x−0.4, x−0.5, x−0.6, etc. In yet another illustration, reference herein to a range of from "x to y" (wherein x is a specific number, and y is a specific number) includes each whole number of x, x+1, x+2 . . . to y−2, y−1, y, as well as each fractional number, such as x+0.1, x+0.2, x+0.3 . . . to y−0.2, y−0.1. In another example, the term "at least 95%" includes each numerical value (including fractional numbers and whole numbers) from 95% to 100%, including, for example, 95%, 96%, 97%, 98%, 99% and 100%.

The terms "antigen," "immunogen," "antigenic," "immunogenic," "antigenically active," "immunologic," and "immunologically active", as used herein, refer to any substance that is capable of inducing a specific immune response (including eliciting a soluble antibody response) and/or cell-mediated immune response (including eliciting a cytotoxic T-lymphocyte (CTL) response).

An individual referred to as "suffering from" a disease, disorder, and/or condition (e.g., influenza or typhoid fever infection) herein has been diagnosed with and/or displays one or more symptoms of a disease, disorder, and/or condition.

As used herein, the term "at risk" for disease (such as bacterial infection), refers to a subject (e.g., a human) that is predisposed to contracting the disease and/or expressing one or more symptoms of the disease. Such subjects include those at risk for failing to elicit an immunogenic response to a vaccine against the disease. This predisposition may be genetic (e.g., a particular genetic tendency to expressing one or more symptoms of the disease, such as heritable disorders, the presence of bacterial species blocking antibodies, the presence of reduced levels of bactericidal antibodies, etc.), or due to other factors (e.g., immune suppressive conditions, environmental conditions, exposures to detrimental compounds, including immunogens, present in the environment, etc.). The term subject "at risk" includes subjects "suffering from disease," i.e., a subject that is experiencing the disease. It is not intended that the present invention be limited to any particular signs or symptoms. Thus, it is intended that the present invention encompasses subjects that are experiencing any range of disease, from sub-clinical infection to full-blown disease, wherein the subject exhibits at least one of the indicia (e.g., signs and symptoms) associated with the disease.

The terms "treat," "treatment," or "treating", as used herein, refer to any method used to partially or completely alleviate, ameliorate, relieve, inhibit, prevent, delay onset of, reduce severity of and/or reduce incidence of one or more symptoms or features of a disease, disorder, and/or condition (e.g., bacterial infection). Treatment may be administered to a subject who does not exhibit signs of a disease, disorder, and/or condition. In some embodiments, treatment may be administered to a subject who exhibits only early signs of the disease, disorder, and/or condition for the purpose of decreasing the risk of developing pathology associated with the disease, disorder, and/or condition.

As used herein, the terms "immunogenically effective amount," "immunologically effective amount", and "antigenically effective amount" refer to that amount of a molecule that elicits and/or increases production of an immune response (including production of specific antibodies and/or induction of a TCL response) in a host upon vaccination. It is preferred, though not required, that the immunologically-effective (i.e., immunogenically effective) amount is a "protective" amount. The terms "protective" and "therapeutic" amount of a composition or vaccine refer to an amount of the composition or vaccine that prevents, delays, reduces, palliates, ameliorates, stabilizes, and/or reverses disease (for example, bacterial infection) and/or one or more symptoms of disease.

As used herein, the term "vaccination" refers to the administration of a composition or vaccine intended to generate an immune response, for example, to a disease-causing agent. For the purposes of the present invention, vaccination can be administered before, during, and/or after exposure to a disease-causing agent, and, in certain embodiments, before, during, and/or shortly after exposure to the agent. In some embodiments, vaccination includes multiple administrations, appropriately spaced in time, of a vaccinating composition (vaccine).

The terms "comprises", "comprising", are intended to have the broad meaning ascribed to them in US Patent Law and can mean "includes", "including" and the like.

The invention can be understood more fully by reference to the following detailed description and illustrative examples, which are intended to exemplify non-limiting embodiments of the invention.

Additional Embodiments of the Invention

In one embodiment, the invention comprises a prokaryotic microorganism. In another embodiment, the prokaryotic microorganism is a bacterial species. Preferably, the prokaryotic microorganism is an attenuated strain of *Salmonella*. However, other prokaryotic microorganisms, such as attenuated strains of *Escherichia coli, Shigella, Yersinia, Lactobacillus, Mycobacteria, Listeria* or *Vibrio* are likewise contemplated for the invention. Examples of suitable strains of microorganisms include, but are not limited to, *Salmonella typhimurium, Salmonella Typhi, Salmonella dublin, Salmonella enteritidis, Escherichia coli, Shigella flexneri, Shigella sonnei, Vibrio cholerae* (Yamamoto, et al. (2009) *Gene* 438:57-64), *Pseudomonas aeruginosa* (Lesic, et al. (2008) *BMC Mol Biol* 9:20), *Yersinia pestis* (Sun, et al. (2008) *Applied and Env Microbiol* 74:4241-4245), and *Mycobacterium bovis* (BCG). Of note, lambda red does not work in *mycobacteria*, but another phage (for example, Che9c gp61) has been used for recombineering in *mycobacteria* (van Kessel, et al. (2008) *Methods mol biol* 435:203-215).

In one preferred embodiment the prokaryotic microorganism is *Salmonella typhi* Ty21a. VIVOTIF® Typhoid Vaccine Live Oral Ty21a is a live attenuated vaccine intended for oral administration. The vaccine contains the attenuated strain *Salmonella Typhi* Ty21a. (Germanier et al. (1975) *J. Infect. Dis.,* 131:553-558). It is manufactured by Bema Biotech Ltd. Berne, Switzerland. *Salmonella Typhi* Ty21a is also described in U.S. Pat. No. 3,856,935.

The attenuated strain of the prokaryotic microorganism undergoes recombineering, such that a large antigenic region is integrated into the chromosome of the microorganism. In one embodiment, the large antigenic region is a *Shigella sonnei* O-antigen biosynthetic gene region, and the prokaryotic organism is a *Salmonella Typhi* Ty21a.

In a further aspect, the present invention provides a composition comprising one or more of above attenuated prokaryotic microorganisms, optionally in combination with a pharmaceutically or physiologically acceptable carrier. Preferably, the composition is a vaccine, especially a vaccine for mucosal immunization, e.g., for administration via the oral, rectal, nasal, vaginal or genital routes. Advantageously, for prophylactic vaccination, the composition comprises one or more strains of *Salmonella* expressing a plurality of different O-Ps genes or of different protein antigens (e.g. anthrax protective antigen or malaria parasite surface proteins).

In a further aspect, the present invention provides an attenuated strain of a prokaryotic microorganism described above for use as a medicament, especially as a vaccine.

In a further aspect, the present invention provides the use of an attenuated strain of a prokaryotic microorganism comprising an O-antigen biosynthetic gene region inserted into a chromosome of the prokaryotic microorganism, wherein the O antigens are produced in the microorganism, in the preparation of a medicament for the prophylactic or therapeutic treatment of one or several different types of bacterial infection (e.g. typhoid fever and dysentery).

Generally, the microorganisms expressing O-Ps according to the present invention are provided in an isolated and/or purified form, i.e., substantially pure. This may include being in a composition where it represents at least about 90% active ingredient, more preferably at least about 95%, more preferably at least about 98%. Such a composition may, however, include inert carrier materials or other pharmaceutically and physiologically acceptable excipients. A composition according to the present invention may include in addition to the microorganisms expressing O-Ps as disclosed, one or more other active ingredients for therapeutic or prophylactic use (e.g. other antigens) and an adjuvant.

The compositions of the present invention are preferably given to an individual in a "prophylactically effective amount" or a "therapeutically effective amount" (as the case may be, although prophylaxis may be considered therapy), this being sufficient to show benefit to the individual. The actual amount administered, and rate and time-course of administration, will depend on the nature and severity of who/what is being treated. Prescription of treatment, e.g., final decisions on acceptable dosage etc., will be dictated by Vaccine Regulatory Authorities, after review of safety and efficacy data following human immunizations.

A composition may be administered alone or in combination with other treatments, either simultaneously or sequentially dependent upon the condition to be treated.

Pharmaceutical compositions according to the present invention, and for use in accordance with the present invention, may include, in addition to active ingredient, a pharmaceutically or physiologically acceptable excipient, carrier, buffer, stabilizer or other materials well known to those skilled in the art. Such materials should be non-toxic and should not interfere with the efficacy of the active ingredient. The precise nature of the carrier or other material will depend on the route of administration.

Examples of techniques and protocols mentioned above can be found in Remington's Pharmaceutical Sciences, 16th edition, Osol, A. (Ed.), 1980.

The invention further relates to the identification and sequencing of 9 ORFs in the rfb locus (GENBANK® accession number: AY585348; SEQ ID NO:3) and an ORF in the rfp locus (GENBANK® accession number: AY763519; SEQ ID NO:4) for *S. dysenteriae* 1 LPS. These genes may be present in whole or in part in the vaccine strains described herein.

Accordingly, the present invention relates to vaccine strains further characterized by the presence of heterologous genes or a set of heterologous genes coding for O-Ps.

In a preferred embodiment of the vaccine strains, the heterologous gene(s) is (are) stably integrated into the chromosome of said strain at a defined integration site which is to be nonessential for growth, for inducing a protective immune response by the carrier strain.

In one embodiment, the heterologous genes of the invention include all 9 ORFs from the rfb locus and the ORF from rfp. In another embodiment, the ninth ORF from rfb is not present, because it is not essential for O-Ps biosynthesis. The ORFs may, in one embodiment, be separated by an insertion sequence element. The latter is the case for *S. sonnei* only.

The ORFs may be under the control of the cognate promoter or other non-cognate promoters. The essential O-antigen biosynthetic genes may be physically together in one operon or separated on the chromosome and present on separate DNA regions under the control of different promoters. The genes may vary in gene order when placed next to one another, as long as they are biologically functional.

Alternatively, the above vaccine strains contain the rfbB, rfbC, and rfbA and/or any additional gene(s) necessary for the synthesis of complete core-linked O-antigen LPS which are integrated in tandem into a single chromosomal site or located at separate chromosomal sites.

Such vaccine strains allow expression of heterologous O-Ps, which is covalently coupled to a heterologous LPS core region, which, preferably, exhibits a degree of polymerization similar to that of native LPS produced by the enteric pathogen. Such vaccine strains can, if desired, be modified in such a way that they are deficient in the synthesis of homologous LPS core.

The invention also relates to a live vaccine comprising the above vaccine strain and optionally a pharmaceutically or physiologically acceptable carrier and/or a buffer for neutralizing gastric acidity and/or a system for delivering said vaccine in a viable state to the intestinal tract.

Said vaccine comprises an immunoprotective or immunotherapeutic and non-toxic amount of said vaccine strain. Suitable dosage amounts can be determined by the person skilled in the art and are typically $10^7$ to $10^{10}$ bacteria.

Pharmaceutically and physiologically acceptable carriers, suitable neutralizing buffers, and suitable delivering systems can be selected by the person skilled in the art.

In a preferred embodiment said live vaccine is used for immunization against gram-negative enteric pathogens.

The mode of administration of the vaccines of the present invention may be any suitable route which delivers an immunoprotective or immunotherapeutic amount of the vaccine to the subject. However, the vaccine is preferably administered orally or intranasally.

The invention also relates to the use of the above vaccine strains for the preparation of a live vaccine for immunization against gram-negative enteric pathogens. For such use the vaccine strains are combined with the carriers, buffers and/or delivery systems described above.

The invention also provides polypeptides and corresponding polynucleotides required for synthesis of core linked O-specific polysaccharide. The invention includes both naturally occurring and unnaturally occurring polynucleotides and polypeptide products thereof. Naturally occurring O-antigen biosynthesis products include distinct gene and polypeptide species as well as corresponding species homologs expressed in organisms other than *Shigella* or *Salmonella* strains. Non-naturally occurring O-antigen biosynthesis products include variants of the naturally occurring products such as analogs and O-antigen biosynthesis products, which include covalent modifications. The sequences of the O-antigen biosynthesis polynucleotides include SEQ ID NOs:3-4 (DNA including *Shigella dysenteriae* serotype 1 polypeptides), which are disclosed in U.S. Pat. No. 8,071,113.

Purified and isolated *Shigella sonnei* polynucleotides (e.g., DNA sequences and RNA transcripts, both sense and complementary antisense strands) encode the bacterial O-antigen biosynthesis gene products. Certain DNA sequences, including genomic and cDNA sequences as well as wholly or partially chemically synthesized DNA sequences, are described in U.S. Pat. No. 8,071,113. Genomic DNA comprises the protein coding region for a polypeptide of the invention and includes variants that may be found in other bacterial strains of the same species. "Synthesized," as used herein and is understood in the art, refers to purely chemical, as opposed to enzymatic, methods for producing polynucleotides. "Wholly" synthesized DNA sequences are therefore produced entirely by chemical means, and "partially" synthesized DNAs embrace those wherein only portions of the resulting DNA were produced by chemical means. Preferred DNA sequences encoding *Shigella sonnei* O-antigen biosynthesis gene products are set out in SEQ ID NO:2, and species homologs thereof. Preferred DNA sequences encoding *Shigella dysenteriae* O-antigen biosynthesis gene products are set out in SEQ ID NOs:3 and 4, and species homologs thereof.

Autonomously replicating recombinant expression constructions such as plasmid and viral DNA vectors incorporating O-antigen biosynthesis gene sequences are also provided. Expression constructs wherein O-antigen biosynthesis polypeptide-encoding polynucleotides are operatively linked to an endogenous or exogenous expression control DNA sequence and a transcription terminator are also provided. The O antigen biosynthesis genes may be cloned by PCR, using *Shigella sonnei* genomic DNA as the template. For ease of inserting the gene into expression vectors, PCR primers are chosen so that the PCR-amplified gene(s) has a restriction enzyme site at the 5' end preceding the initiation codon ATG, and a restriction enzyme site at the 3' end after the termination codon TAG, TGA or TAA. If desirable, the codons in the gene(s) are changed, without changing the amino acids, according to *E. coli* codon preference described by Grosjean et al. (1982) *Gene,* 18:199-209; and Konigsberg et al. (1983) *Proc. Natl. Acad. Sci. USA,* 80:687-691. Optimization of codon usage may lead to an increase in the expression of the gene product when produced in *E. coli*. If a protein gene product is to be produced extracellularly, either in the periplasm of *E. coli* or other bacteria, or into the cell culture medium, the gene is cloned into an expression vector and linked to a signal sequence.

According to another aspect of the invention, host cells are provided, including prokaryotic and eukaryotic cells, either stably or transiently transformed, transfected, or electroporated with polynucleotide sequences of the invention in a manner which permits expression of O antigen biosynthesis polypeptides of the invention. Potential expression systems of the invention include bacterial, yeast, fungal, viral, parasitic, invertebrate, and mammalian cells systems. Host cells of the invention are a valuable source of immunogen for development of anti-bodies specifically immunoreactive with the O antigen. Host cells of the invention are conspicuously useful in methods for large scale production of O antigen biosynthesis polypeptides wherein the cells are grown in a suitable culture medium and the desired polypeptide products are isolated from the cells or from the medium in which the cells are grown by, for example, immunoaffinity purification or any of the multitude of purification techniques well known and routinely practiced in the art. Any suitable host cell may be used for expression of the gene product, such as *E. coli*, other bacteria, including *P. multocida, Bacillus* and *S. aureus*, yeast, including *Pichia pastoris* and *Saccharomyces cerevisiae*, insect cells, or mammalian cells, including CHO cells, utilizing suitable vectors known in the art. Proteins may be produced directly or fused to a peptide or polypeptide, and either intracellularly or extracellularly by secretion into the periplasmic space of a bacterial cell or into the cell culture medium. Secretion of a protein requires a signal peptide (also known as pre-sequence); a number of signal sequences from prokaryotes and eukaryotes are known to function for the secretion of recombinant proteins. During the protein secretion process, the signal peptide is removed by signal peptidase to yield the mature protein.

To simplify the protein purification process, a purification tag may be added either at the 5' or 3' end of the gene coding sequence. Commonly used purification tags include a stretch of six histidine residues (U.S. Pat. Nos. 5,284,933 and 5,310,663), a streptavidin affinity tag described by Schmidt et al. (1993) *Protein Eng.,* 6:109-122, a FLAG peptide (Hopp et al. (1988) *Biotechnology,* 6:1205-1210), glutathione 5-transferase (Smith et al. (1988) *Gene,* 67:31-40), and thioredoxin (LaVallie et at. (1993) *Bio/Technology,* 11:187-193). To remove these peptide or polypeptides, a proteolytic cleavage recognition site may be inserted at the fusion junction. Commonly used proteases are factor Xa, thrombin, and enterokinase.

In one embodiment, the invention employs purified and isolated *Shigella sonnei* O-antigen biosynthesis polypeptides as described above. Presently preferred are polypeptides comprising the amino acid sequences encoded by any one of the polynucleotides set out in SEQ ID NO:2, and species homologs thereof. In certain embodiments, the invention utilizes O antigen biosynthesis polypeptides encoded by a DNA selected from the group consisting of:

a) the DNA sequence set out in any one of SEQ ID NO:2 and species homologs thereof;

b) DNA molecules encoding *Shigella sonnei* O-antigen biosynthetic polypeptides encoded by any one of SEQ ID NO:2, and species homologs thereof; and c) a DNA molecule encoding a O-antigen biosynthesis gene product that hybridizes under moderately stringent conditions to the DNA of (a) or (b). Moderately stringent hybridization conditions are well-known to the ordinarily skilled artisan.

The invention also embraces polypeptides that have at least about 99%, at least about 95%, at least about 90%, at least about 85%, at least about 80%, at least about 75%, at least about 70%, at least about 65%, at least about 60%, at least about 55%, and at least about 50% identity and/or homology to the preferred polypeptides of the invention. Percent amino acid sequence "identity" with respect to the preferred polypeptides of the invention is defined herein as the percentage of amino acid residues in the candidate sequence that are identical with the residues in the O antigen biosynthesis gene product sequence after aligning both sequences and introducing gaps, if necessary, to achieve the maximum percent sequence identity, and not considering any conservative substitutions as part of the sequence identity. Percent sequence "homology" with respect to the preferred polypeptides of the invention is defined herein as the percentage of amino acid residues in the candidate sequence that are identical with the residues in one of the O antigen biosynthesis polypeptide sequences after aligning the sequences and introducing gaps, if necessary, to achieve the maximum percent sequence identity, and also considering any conservative substitutions as part of the sequence identity. Conservative substitutions can be defined as set out below in Tables A and B.

TABLE A

Conservative Substitutions I

| SIDE CHAIN | CHARACTERISTIC | AMINO ACID |
|---|---|---|
| Aliphatic | Non-polar | G, A, P |
| | | I, L, V |
| | Polar-uncharged | C, S, T, M |
| | | N, Q |
| | Polar-charged | D, E |
| | | K, R |
| Aromatic | | H, F, W, Y |
| Other | | N, Q, D, E |

Polypeptides of the invention may be isolated from natural bacterial cell sources or may be chemically synthesized, but are preferably produced by recombinant procedures involving host cells of the invention. O antigen biosynthesis gene products of the invention may be full length polypeptides, biologically active fragments, or variants thereof which retain specific biological or immunological activity. The biological activity is, in one embodiment, the biosynthesis of the antigen, for example, the *Shigella sonnei* O-antigen. The immunological activity is, in one embodiment, the protective immunological activity of the antigenic gene product, for example, the O-antigen product. Variants may comprise O antigen biosynthesis polypeptide analogs wherein one or more of the specified (i.e., naturally encoded) amino acids is deleted or replaced or wherein one or more non-specified amino acids are added: (1) without loss of one or more of the biological activities or immunological characteristics (activity) specific for the O antigen biosynthesis gene product; or (2) with specific disablement of a particular biological activity of the O antigen biosynthesis gene product. Deletion variants contemplated also include fragments lacking portions of the polypeptide not essential for biological activity, and insertion variants include fusion polypeptides in which the wild-type polypeptide or fragment thereof have been fused to another polypeptide.

Variant O antigen biosynthesis polypeptides include those wherein conservative substitutions have been introduced by modification of polynucleotides encoding polypeptides of the invention. Conservative substitutions are recognized in the art to classify amino acids according to their related physical properties and can be defined as set out in Table A (from WO 1997/009433, page 10). Alternatively, conservative amino acids can be grouped as defined in Lehninger, (Biochemistry, Second Edition (1975) W.H. Freeman & Co., pp. 71-77) as set out in Table B.

TABLE B

Conservative Substitutions II

| SIDE CHAIN CHARACTERISTIC | AMINO ACID |
|---|---|
| Non-polar (hydrophobic) | |
| A. Aliphatic: | A, L, I, V, P |
| B. Aromatic: | F, W |
| C. Sulfur-containing: | M |
| D. Borderline: | G |
| Uncharged-polar | |
| A. Hydroxyl: | S, T, Y |
| B. Amides: | N, Q |
| C. Sulfhydryl: | C |
| D. Borderline: | G |
| Positively Charged (Basic): | K, R, H |
| Negatively Charged (Acidic): | D, E |

Variant O antigen biosynthesis products of the invention include mature O antigen biosynthesis gene products, i.e., wherein leader or signal sequences are removed, having additional amino terminal residues. O antigen biosynthesis gene products having an additional methionine residue at position −1 are contemplated, as are O antigen biosynthesis products having additional methionine and lysine residues at positions −2 and −1. Variants of these types are particularly useful for recombinant protein production in bacterial cell types. Variants of the invention also include gene products wherein amino terminal sequences derived from other proteins have been introduced, as well as variants comprising amino terminal sequences that are not found in naturally occurring proteins.

The invention also embraces variant polypeptides having additional amino acid residues which result from use of specific expression systems. For example, use of commercially available vectors that express a desired polypeptide as fusion protein with glutathione-S-transferase (GST) provide the desired polypeptide having an additional glycine residue at position −1 following cleavage of the GST component from the desired polypeptide. Variants which result from expression using other vector systems are also contemplated.

Also comprehended by the present invention are antibodies (e.g., monoclonal and polyclonal antibodies, single chain antibodies, chimeric antibodies, humanized, human, and CDR-grafted antibodies, including compounds which include CDR sequences which specifically recognize a polypeptide of the invention) and other binding proteins specific for O antigen biosynthesis gene products or fragments thereof. The term "specific for" indicates that the variable regions of the antibodies of the invention recognize and bind O antigen exclusively (i.e., are oftentimes able to distinguish a single O antigen from related O antigens, but may also interact with other proteins (for example, *S. aureus* protein A or other antibodies in ELISA techniques) through interactions with sequences outside the variable region of the antibodies, and in particular, in the constant region of the molecule. Screening assays to determine binding specificity of an antibody of the invention are well known and routinely practiced in the art. For a comprehensive discussion of such assays, see Harlow et al. (Eds.); Antibodies A Laboratory Manual (1988) Cold Spring Harbor Laboratory; Cold Spring Harbor, N.Y., chapter 6. Antibodies that recognize and bind fragments of the O antigen of the invention are also contemplated, provided that the antibodies are first and foremost specific for, as defined above, an O antigen of the invention from which the fragment was derived.

Treatment/Therapy

In certain embodiments, the present invention provides compositions (including vaccines) and methods to treat (e.g., alleviate, ameliorate, relieve, delay onset of, inhibit progression of, reduce severity of, and/or reduce incidence of one or more symptoms or features of) and/or prevent bacterial infection.

In some embodiments, methods of vaccination and/or treatment (such as those described in the sections below) involve stratification of a patient population based on prior exposure to bacterial strains. Such methods involve steps of determining whether a patient has been previously exposed to one or more of the bacterial strains. In some embodiments, if it is determined that a patient has been previously been exposed to one or more of the bacterial strains, that patient may receive less concentrated, less potent, and/or less frequent doses of the inventive vaccine or composition. If it is determined that a patient has not been previously been exposed to one or more of the bacterial strains, that patient may receive more concentrated, more potent, and/or more frequent doses of the inventive vaccine or composition.

In one embodiment, the recombineered bacterial strain or vaccine or composition of the invention treats more than one bacterial infection, i.e., infection with more than one bacterial species. It can, in such an embodiment, be deemed a "multifunctional" vaccine (or strain or composition—either of the latter two are contemplated in the continued description, below). A multifunctional vaccine according to the invention may also be useful for treating and/or preventing simultaneously a number of different disorders in a subject. Accordingly, the present invention further provides, in an additional embodiment, a method for treating and/or preventing more than one disorder in a subject, by administering to the subject a multifunctional vaccine according to the invention.

Exemplary disorders which potentially may be treated and/or prevented by a multifunctional vaccine according to the invention include, without limitation, multiple bacterial species infections, burns, infections, neoplasia, or radiation injuries. "Neoplasia" refers to the uncontrolled and progressive multiplication of tumour cells, under conditions that would not elicit, or would cause cessation of, multiplication of normal cells. Neoplasia results in a "neoplasm", which is defined herein to mean any new and abnormal growth, particularly a new growth of tissue, in which the growth of cells is uncontrolled and progressive. Thus, neoplasia includes "cancer", which herein refers to a proliferation of tumour cells having the unique trait of loss of normal controls, resulting in unregulated growth, lack of differentiation, local tissue invasion, and/or metastasis.

Administration

Compositions and vaccines (the terms used interchangeably herein) may be administered using any amount and any route of administration effective for treatment and/or vaccination. The exact amount required will vary from subject to subject, depending on the species, age, and general condition of the subject, the severity of the infection, the particular composition, its mode of administration, its mode of activity, and the like. Compositions are typically formulated in dosage unit form for ease of administration and uniformity of dosage. It will be understood, however, that the total daily usage of the compositions of the present invention will be decided by the attending physician within the scope of sound medical judgment. The specific therapeutically effective dose level for any particular subject or organism will depend upon a variety of factors including the disorder being treated and/or vaccinated and the severity of the disorder; the activity of the specific vaccine composition employed; the half-life of the composition after administration; the age, body weight, general health, sex, and diet of the subject; the time of administration, route of administration, and rate of excretion of the specific compound employed; the duration of the treatment; drugs used in combination or coincidental with the specific compound employed; and like factors, well known in the medical arts.

Compositions (and vaccines) according to the invention may be administered by any route. In some embodiments, pharmaceutical compositions of the present invention are administered by a variety of routes, including oral (PO), intravenous (IV), intramuscular (IM), intra-arterial, intramedullary, intrathecal, subcutaneous (SQ), intraventricular, transdermal, interdermal, intradermal, rectal (PR), vaginal, intraperitoneal (IP), intragastric (IG), topical or transcutaneous (e.g., by powders, ointments, creams, gels, lotions, and/or drops), mucosal, intranasal, buccal, enteral, vitreal, sublingual; by intratracheal instillation, bronchial instillation, and/or inhalation; as an oral spray, nasal spray, and/or aerosol, and/or through a portal vein catheter.

In general, the most appropriate route of administration will depend upon a variety of factors including the nature of the agent being administered (e.g., its stability upon administration), the condition of the subject (e.g., whether the subject is able to tolerate a particular mode of administration), etc. In specific embodiments, compositions may be administered intranasally. In specific embodiments, compositions may be administered by intratracheal instillation. In specific embodiments, compositions may be administered by bronchial instillation. In specific embodiments, compositions may be administered by inhalation. In specific embodiments, compositions may be administered as a nasal spray. In specific embodiments, compositions may be administered mucosally. In specific embodiments, compositions may be administered orally. In specific embodiments, compositions may be administered by intravenous injection. In specific embodiments, compositions may be administered by intramuscular injection. In specific embodiments, compositions may be administered by subcutaneous injection. The oral or nasal spray or aerosol route (e.g., by inhalation) is most commonly used to deliver therapeutic agents directly to the lungs and respiratory system. However, the invention encompasses the delivery of a pharmaceutical composition by any appropriate route taking into consideration likely advances in the sciences of drug delivery.

For oral administration, the composition (including vaccine) may be presented as capsules, tablets, dissolvable membranes, powders, granules, or as a suspension. The composition may have conventional additives, such as lactose, mannitol, corn starch, or potato starch. The composition also may be presented with binders, such as crystalline cellulose, cellulose derivatives, acacia, corn starch, or gelatins. Additionally, the composition may be presented with disintegrators, such as corn starch, potato starch, or sodium carboxymethylcellulose. The composition may be further presented with dibasic calcium phosphate anhydrous or sodium starch glycolate. Finally, the composition may be presented with lubricants, such as talc or magnesium stearate.

For parenteral administration, the composition may be combined with a sterile aqueous solution, which is preferably isotonic with the blood of the subject. Such a formulation may be prepared by dissolving a solid active ingredient in water containing physiologically-compatible substances, such as sodium chloride, glycine, and the like, and having a buffered pH compatible with physiological conditions, so as to produce an aqueous solution, then rendering said solution sterile. The formulation may be presented in unit or multi-dose containers, such as sealed ampoules or vials. The formulation also may be delivered by any mode of injection, including any of those described herein.

Compositions for rectal or vaginal administration are typically suppositories which can be prepared by mixing compositions with suitable non-irritating excipients such as cocoa butter, polyethylene glycol or a suppository wax which are solid at ambient temperature but liquid at body temperature and therefore melt in the rectum or vaginal cavity and release the active ingredient.

Solid dosage forms for oral administration include capsules, tablets, pills, powders, dissolvable membranes, and granules. In such solid dosage forms, the active ingredient is mixed with at least one inert, pharmaceutically acceptable excipient such as sodium citrate or dicalcium phosphate and/or fillers or extenders (e.g., starches, lactose, sucrose, glucose, mannitol, and silicic acid), binders (e.g., carboxymethylcellulose, alginates, gelatin, polyvinylpyrrolidinone, sucrose, and acacia), humectants (e.g., glycerol), disintegrating agents (e.g., agar, calcium carbonate, potato starch, tapioca starch, alginic acid, certain silicates, and sodium carbonate), solution retarding agents (e.g., paraffin), absorption accelerators (e.g., quaternary ammonium compounds), wetting agents (e.g., cetyl alcohol and glycerol monostearate), absorbents (e.g., kaolin and bentonite clay), and lubricants (e.g., talc, calcium stearate, magnesium stearate, solid polyethylene glycols, sodium lauryl sulfate), taste/olfactory components, and mixtures thereof. In the case of capsules, tablets and pills, the dosage form may comprise buffering agents.

Dosage forms for topical and/or transdermal administration of a composition in accordance with this invention may include ointments, pastes, creams, lotions, gels, powders, solutions, sprays, inhalants and/or patches. Generally, the active ingredient is admixed under sterile conditions with a pharmaceutically acceptable excipient and/or any needed preservatives and/or buffers as may be required. Additionally, the present invention contemplates the use of transdermal patches, which often have the added advantage of providing controlled delivery of a compound to the body. Such dosage forms may be prepared, for example, by dissolving and/or dispensing the compound in the proper medium. Alternatively or additionally, the rate may be controlled by either providing a rate controlling membrane and/or by dispersing the compound in a polymer matrix and/or gel.

For transdermal administration, the composition (including vaccine) according to the invention may be combined with skin penetration enhancers, such as propylene glycol, polyethylene glycol, isopropanol, ethanol, oleic acid, N-methylpyrrolidone, and the like, which increase the permeability of the skin to the composition, and permit the composition to penetrate through the skin and into the bloodstream. The composition of enhancer and vaccine also may be further combined with a polymeric substance, such as ethylcellulose, hydroxypropyl cellulose, ethylene/vinylacetate, polyvinyl pyrrolidone, and the like, to provide the composition in gel form, which may be dissolved in solvent, such as methylene chloride, evaporated to the desired viscosity, and then applied to backing material to provide a patch. The composition may be administered transdermally, at or near the site on the subject where the infection, neoplasm, or other disorder may be localized. Alternatively, the composition may be administered transdermally at a site other than the affected area, in order to achieve systemic administration.

For intranasal administration (e.g., nasal sprays) and/or pulmonary administration (administration by inhalation), a composition (including vaccine) according to the invention, including aerosol formulations, may be prepared in accordance with procedures well known to persons of skill in the art. Aerosol formulations may comprise either solid particles or solutions (aqueous or non-aqueous). Nebulizers (e.g., jet nebulizers, ultrasonic nebulizers, etc.) and atomizers may be used to produce aerosols from solutions (e.g., using a solvent such as ethanol); metered-dose inhalers and dry-powder inhalers may be used to generate small-particle aerosols. The desired aerosol particle size can be obtained by employing any one of a number of methods known in the art, including, without limitation, jet-milling, spray drying, and critical-point condensation.

Compositions for intranasal administration may be solid formulations (e.g., a coarse powder) and may contain excipients (e.g., lactose). Solid formulations may be administered from a container of powder held up to the nose, using rapid inhalation through the nasal passages. Compositions for intranasal administration may also comprise aqueous or oily solutions of nasal spray or nasal drops. For use with a sprayer, the formulation may comprise an aqueous solution and additional agents, including, for example, an excipient, a buffer, an isotonicity agent, a preservative, or a surfactant. A nasal spray may be produced, for example, by forcing a suspension or solution of the composition through a nozzle under pressure.

Formulations of a composition (including vaccine) according to the invention for pulmonary administration may be presented in a form suitable for delivery by an inhalation device, and may have a particle size effective for reaching the lower airways of the lungs or sinuses. For absorption through mucosal surfaces, including the pulmonary mucosa, the formulation may comprise an emulsion that includes, for example, a bioactive peptide, a plurality of submicron particles, a mucoadhesive macromolecule, and/or an aqueous continuous phase. Absorption through mucosal surfaces may be achieved through mucoadhesion of the emulsion particles.

Compositions (including vaccines) according to the invention for use with a metered-dose inhaler device may include a finely-divided powder containing the composition as a suspension in a non-aqueous medium. For example, the composition may be suspended in a propellant with the aid of a surfactant (e.g., sorbitan trioleate, soya lecithin, or oleic acid). Metered-dose inhalers typically use a propellant gas (e.g., a chlorofluorocarbon, a hydrochlorofluorocarbon, a hydrofluorocarbon, or a hydrocarbon) stored in a container (e.g., a canister) as a mixture (e.g., as a liquefied, compressed gas). Inhalers require actuation during inspiration. For example, actuation of a metering valve may release the mixture as an aerosol. Dry-powder inhalers use breath-actuation of a mixed powder.

A composition (including vaccine) according to the invention also may be released or delivered from an osmotic mini-pump or other timed-release device. The release rate from an elementary osmotic mini-pump may be modulated with a microporous, fast-response gel disposed in the release orifice. An osmotic mini-pump would be useful for controlling release, or targeting delivery, of the composition.

A composition (including vaccine) according to the invention may be administered or introduced to a subject by known techniques used for the introduction of drugs, including, for example, injection and transfusion. Where a disorder is localized to a particular portion of the body of the subject, it may be desirable to introduce the composition directly to that area by injection or by some other means (e.g., by introducing the composition into the blood or another body fluid).

A composition (including vaccine) according to the invention may be administered to a subject who has a disorder, either alone or in combination with one or more drugs used to treat that disorder. For example, where the subject has neoplasia, the composition may be administered to a subject in combination with at least one antineoplastic drug. Examples of antineoplastic drugs with which the composition may be combined include, without limitation, carboplatin, cyclophosphamide, doxorubicin, etoposide, and vincristine. Additionally, when administered to a subject who suffers from neoplasia, the composition may be combined with other neoplastic therapies, including, without limitation, surgical therapies, radiotherapies, gene therapies, and immunotherapies.

Vaccine

A "vaccine" is a composition that induces an immune response in the recipient or host of the vaccine. The vaccine can induce protection against infection upon subsequent challenge with a bacterial species (or other microorganism). Protection refers to resistance (e.g., partial resistance) to persistent infection of a host animal with at least one bacterial species (or other microorganism). Neutralizing antibodies generated in the vaccinated host can provide this protection. In other situations, CTL responses can provide this protection. In some situations, both neutralizing antibodies and cell-mediated immune (e.g., CTL) responses provide this protection.

Vaccines are useful in preventing or reducing infection or disease by inducing immune responses, to an antigen or antigens, in an individual. For example, vaccines can be used prophylactically in naive individuals, or therapeutically in individuals already infected with at least one bacterial species (or other microorganism).

Protective responses can be evaluated by a variety of methods. For example, either the generation of neutralizing antibodies against bacterial (or other microorganism) proteins, and/or the generation of a cell-mediated immune response against such proteins can indicate a protective response. Protective responses also include those responses that result in lower number of bacteria colonized in a vaccinated host animal exposed to a given inoculum (of bacteria or other microorganism) as compared to a host animal exposed to the same inoculum, but that has not been administered the vaccine.

Vaccines according to the invention may, in one embodiment, contain an adjuvant. The term "adjuvant", as used herein, refers to any compound which, when injected together with an antigen, non-specifically enhances the immune response to that antigen. Exemplary adjuvants include Complete Freund's Adjuvant, Incomplete Freund's Adjuvant, Gerbu adjuvant (GMDP; C.C. Biotech Corp.), RIBI fowl adjuvant (MPL; RIBI Immunochemical Research, Inc.), potassium alum, aluminum phosphate, aluminum hydroxide, QS21 (Cambridge Biotech), TITERMAX® adjuvant (CytRx Corporation), and QUIL A® adjuvant. Other compounds that may have adjuvant properties include binders such as carboxymethylcellulose, ethyl cellulose, microcrystalline cellulose, or gelatin; excipients such as starch, lactose or dextrins, disintegrating agents such as alginic acid, sodium alginate, PRIMOGEL®, corn starch and the like; lubricants such as magnesium stearate or STEROTEX®; glidants such as colloidal silicon dioxide; sweetening agents such as sucrose or saccharin, a flavoring agent such as peppermint, methyl salicylate or orange flavoring, and a coloring agent.

Furthermore, a useful compendium of many adjuvants is prepared by the National Institutes of Health and can be found on the internet (www.niaid.nih.gov/daids/vaccine/pdf/compendium.pdf). Hundreds of different adjuvants are known in the art and could be employed in the practice of the present invention. Exemplary adjuvants that can be utilized in accordance with the invention include, but are not limited to, cytokines, aluminum salts (e.g., aluminum hydroxide, aluminum phosphate, etc.), gel-type adjuvants (e.g., calcium phosphate, etc.); microbial adjuvants (e.g., immunomodulatory DNA sequences that include CpG motifs; endotoxins such as monophosphoryl lipid A); exotoxins such as cholera toxin, *E. coli* heat labile toxin, and pertussis toxin; muramyl dipeptide, etc.); oil-emulsion and emulsifier-based adjuvants (e.g., Freund's Adjuvant, MF59 [Novartis], SAF, etc.); particulate adjuvants (e.g., liposomes, biodegradable microspheres, etc.); synthetic adjuvants (e.g., nonionic block copolymers, muramyl peptide analogues, polyphosphazene, synthetic polynucleotides, etc.); and/or combinations thereof. Other exemplary adjuvants include some polymers (e.g., polyphosphazenes), Q57, saponins (e.g., QS21), squalene, tetrachlorodecaoxide, CPG 7909, poly[di(carboxylatophenoxy)phosphazene] (PCCP), interferon-gamma, block copolymer P1205 (CRL1005), interleukin-2 (IL-2), polymethyl methacrylate (PMMA), etc. In one embodiment of the instant invention, the carrier bacterium (e.g. *S. Typhi* Ty21a) itself serves as an adjuvant for expressed foreign antigens such as *Shigella* O antigens or anthrax protective antigen.

Vaccines according to the invention may, in another embodiment, be formulated using a diluent. Exemplary "diluents" include water, physiological saline solution, human serum albumin, oils, polyethylene glycols, glycerine, propylene glycol or other synthetic solvents, antibacterial agents such as benzyl alcohol, antioxidants such as ascorbic acid or sodium bisulphite, chelating agents such as ethylene diamine-tetra-acetic acid, buffers such as acetates, citrates or phosphates and agents for adjusting the osmolarity, such as sodium chloride or dextrose. Exemplary "carriers" include liquid carriers (such as water, saline, culture medium, saline, aqueous dextrose, and glycols) and solid carriers (such as carbohydrates exemplified by starch, glucose, lactose, sucrose, and dextrans, anti-oxidants exemplified by ascorbic acid and glutathione, and hydrolyzed proteins.

Vaccines according to the invention may, in still another embodiment, contain an excipient. The term "excipient" refers herein to any inert substance (e.g., gum arabic, syrup, lanolin, starch, etc.) that forms a vehicle for delivery of an antigen. The term excipient includes substances that, in the presence of sufficient liquid, impart to a composition the adhesive quality needed for the preparation of pills or tablets.

As mentioned above, in some embodiments, interfering agents and/or binding agents in accordance with the invention may be utilized for prophylactic applications. In some embodiments, prophylactic applications involve systems and methods for preventing, inhibiting progression of, and/or delaying the onset of bacterial infection. In some embodiments, interfering agents may be utilized for passive immunization (i.e., immunization wherein antibodies are administered to a subject). In some embodiments, vaccines for passive immunization may comprise antibody interfering agents, such as those described herein. In some embodiments, passive immunization occurs when antibodies are transferred from mother to fetus during pregnancy. In some embodiments, antibodies are administered directly to an individual (e.g., by injection, orally, etc.). Of note, it is possible to immunize a person and use their antibodies for passive protection in another individual. For example, Ty21a is contraindicated for use in pregnant women (i.e., they are immunocompromised, and the attenuated *Salmonella* could potentially cause illness). However, it may be appropriate to passively transfer protective antibodies to a pregnant mother, instead of leaving them susceptible to deadly diseases.

The invention provides, in one embodiment, vaccines for active immunization (i.e., immunization wherein microbes, proteins, peptides, epitopes, mimotopes, etc. are administered to a subject). In some embodiments, the vaccines may comprise one or more interfering agents and/or binding agents, as described herein.

In one embodiment, a composition is provided including interfering agents and/or binding agents, as described for vaccines, above. For example, in some embodiments, interfering agent and/or binding agent polypeptides, nucleic acids encoding such polypeptides, characteristic or biologically active fragments of such polypeptides or nucleic acids, antibodies that bind to and/or compete with such polypeptides or fragments, small molecules that interact with or compete with such polypeptides or with glycans that bind to them, etc. are included in compositions. In some embodiments, interfering agents and/or binding agents that are not polypeptides, e.g., that are small molecules, umbrella topology glycans and mimics thereof, carbohydrates, aptamers, polymers, nucleic acids, etc., are included in the compositions. One could, in specific embodiments, envision bacterially delivered therapies for cancer or other maladies, in which the therapeutic nucleic acids or proteins are encoded in the chromosome of the carrier bacterial vaccine/therapeutic strain.

The invention encompasses treatment and/or prophylaxis of bacterial (or other microorganism) infections by administration of compositions according to the invention. In some embodiments, such compositions are administered to a subject suffering from or susceptible to a bacterial infection. In some embodiments, a subject is considered to be suffering from a bacterial infection if the subject is displaying one or more symptoms commonly associated with the bacterial infection. In some embodiments, the subject is known or believed to have been exposed to the at least one bacterial species (or other microorganism). In some embodiments, a subject is considered to be susceptible to a bacterial infection if the subject is known or believed to have been exposed to the bacterial species. In some embodiments, a subject is known or believed to have been exposed to the bacterial species if the subject has been in contact with other individuals known or suspected to have been infected with the same, and/or if the subject is or has been present in a location in which the bacterial infection is known or thought to be prevalent. Compositions provided herein may be administered prior to or after development of one or more symptoms of bacterial (or other microorganism) infection.

In general, a composition will include a "therapeutic agent" (the recombineered *Salmonella Typhi* Ty21a, for example), in addition to one or more inactive, agents such as a sterile, biocompatible pharmaceutical carrier including, but not limited to, sterile water, saline, buffered saline, or dextrose solution. Alternatively or additionally, a composition may comprise a pharmaceutically acceptable excipient, which, as used herein, includes any and all solvents, dispersion media, diluents, or other liquid vehicles, dispersion or suspension aids, disintegrating agents, surface active agents, isotonic agents, thickening or emulsifying agents, preservatives, buffering agents, solid binders, granulating agents, lubricants, coloring agents, sweetening agents, flavoring agents, perfuming agents, and the like, as suited to the particular dosage form desired. Remington's The Science and Practice of Pharmacy, 21st Ed., A. R. Gennaro, (Lippincott, Williams & Wilkins, Baltimore, Md., 2006; incorporated herein by reference) discloses various excipients used in formulating pharmaceutical compositions and known techniques for the preparation thereof. Except insofar as any conventional excipient medium is incompatible with a substance or its derivatives, such as by producing any undesirable biological effect or otherwise interacting in a deleterious manner with any other component of the pharmaceutical composition, its use is contemplated to be within the scope of this invention.

Combinations

Compositions and vaccines according to the invention can be administered to a subject either alone or in combination with one or more other therapeutic agents including, but not limited to, vaccines and/or antibodies. By "in combination with," it is not intended to imply that the agents must be administered at the same time or formulated for delivery together, although these methods of delivery are within the scope of the invention. Compositions and vaccines according to the invention can be administered concurrently with, prior to, or subsequent to, one or more other desired therapeutics or medical procedures. It will be appreciated that therapeutically active agents utilized in combination may be administered together in a single composition or administered separately in different compositions. In general, each agent will be administered at a dose and/or on a time schedule determined for that agent.

In general, each agent (in this context, one of the "agents" is a composition or vaccine according to the invention) will be administered at a dose and on a time schedule determined for that agent. Additionally, the invention encompasses the delivery of the compositions in combination with agents that may improve their bioavailability, reduce or modify their metabolism, inhibit their excretion, or modify their distribution within the body. Although the compositions (including vaccines) according to the invention can be used for treatment and/or vaccination of any subject, they are preferably used in the treatment and/or vaccination of humans.

The particular combination of therapies (e.g., therapeutics or procedures) to employ in a combination regimen will take into account compatibility of the desired therapeutics and/or procedures and the desired therapeutic effect to be achieved. It will be appreciated that the therapies employed may achieve a desired effect for the same purpose (for example, an agent useful for treating, preventing, and/or delaying the onset of a bacterial (or other microorganism) infection may be administered concurrently with another agent useful for treating, preventing, and/or delaying the onset of the bacterial infection), or they may achieve different effects (e.g., prevention of severe illness or control of adverse effects).

In general, it is expected that agents utilized in combination with be utilized at levels that do not exceed the levels at which they are utilized individually. In some embodiments, the levels utilized in combination will be lower than those utilized individually.

Dosages

The dosage of a vaccine (or other composition) according to the invention can be determined by, for example, first identifying doses effective to elicit a prophylactic and/or therapeutic immune response. This may be accomplished by measuring the serum titer of bacterium-specific immunoglobulins and/or by measuring the inhibitory ratio of antibodies in serum samples, urine samples, and/or mucosal secretions. The dosages can be determined from animal studies, including animals that are not natural hosts to the bacterial species in question. For example, the animals can be dosed with a vaccine candidate, e.g., a vaccine according to the invention, to partially characterize the immune response induced and/or to determine if any neutralizing antibodies have been produced. In addition, routine human clinical studies can be performed to determine the effective dose for humans.

Effective doses may be extrapolated from dose-response curves derived from in vitro and/or in vivo animal models. Ty21a is given every other day for three or four doses (depending on country of use), and the dose may be between about $2\times10^9$ and $>10^{10}$ colony forming units (cfu) per dose. In one embodiment, dose spacing of every one to two months works better in some immunization schedules (e.g. in infants), and in another embodiment, doses as high as $10^{11}$ cfu may work better in developing countries (i.e., trigger better protection that persists longer).

An immunologically effective amount, based upon human studies, would, in one embodiment, be sufficient to stimulate an acceptable level of protective immunity in a population. For some vaccines (in certain embodiments), this immunologically effective level would provide an 80% efficacy against a specific diarrheal disease. For other vaccines (in other embodiments), an immunologically effective amount would be one that protects against severe disease but may not protect against all symptoms of a disease.

In one embodiment, a vaccine (or other composition) according to the invention may also be administered to a subject at risk of developing a disorder, in an amount effective to prevent the disorder in the subject. As used herein, the phrase "effective to prevent the disorder" includes effective to hinder or prevent the development or manifestation of clinical impairment or symptoms resulting from the disorder, or to reduce in intensity, severity, and/or frequency, and/or delay of onset of one or more symptoms of the disorder.

Kits

Kits comprising the recombineered *Salmonella Typhi* Ty21a or a vaccine or a composition according to the invention are provided in an additional embodiment. Kits can include one or more other elements including, but not limited to, instructions for use; other reagents, e.g., a diluent, devices or other materials for preparing the vaccine or composition for administration; pharmaceutically acceptable carriers; and devices or other materials for administration to a subject. Instructions for use can include instructions for therapeutic application (e.g., DNA vaccination and protein boosting) including suggested dosages and/or modes of administration, e.g., in a human subject, as described herein.

In another embodiment, a kit according to the invention can further contain at least one additional reagent, such as a diagnostic or therapeutic agent, e.g., a diagnostic agent to monitor an immune response to the compositions or vaccines according to the invention in the subject, or an additional therapeutic agent as described herein (see, e.g., the section herein describing combination therapies).

EXAMPLES

The following examples are provided for illustrative purposes only and are not intended to limit the scope of the invention.

Example 1. Cloning the Minimal Essential *S. sonnei* O-Antigen Biosynthetic Genes A large 30 kb region encoding *S. sonnei* form I O-antigen biosynthesis and flanking sequences were previously characterized (initially by deletion analysis) to determine minimal necessary sequences for O-antigen expression. Together with DNA sequence analyses of this region, these deletion data indicated that a contiguous 12.3 kb region containing a putative promoter and 10 orfs (orf 4 to 13 in FIG. 1) was required for O-antigen biosynthesis in *S. sonnei*. These deletion studies also suggested that wzz (ofr3), typically involved in regulating O-antigen chain length, is not essential for form 1 expression in Ty21a, but the latter part of wzz apparently contains the putative form 1 O-antigen biosynthetic operon promoter (Xu, et al. (2002) *Infect and Immun* 70:4414-4423.

Construction of pMD-TV Plasmid

Standard molecular biology techniques were used for cloning. The restriction endonucleases and ligase were purchased from New England Biolabs (NEB) or FERMENTAS®, and PHUSION® polymerase (Fisher) was used for all PCRs. The $Kan^r$ cassette flanked by FRT sites was PCR-amplified from pKD4 with primers containing NheI and NsiI restriction sites, and plasmid pGB-2 was also PCR amplified with primers containing NheI and NsiI restriction sites, engineered to delete the open reading frame (orf) that confers Spc resistance. The two PCR products were digested with NheI and NsiI and ligated to construct the $Kan^r$, $Spc^S$ plasmid pMD35-36. The vexA gene (~1000 bp) and part of the tviD gene (~500 bp) were PCR-amplified from Ty21a genomic DNA. The amplified tviD sequence was cloned upstream of the $Kan^r$ cassette flanked by FRT sites, and the vexA amplicon was cloned downstream of the multiple cloning site (MCS), as shown in FIG. 1. Restriction endonuclease sites were further added or removed, as needed, by the method described in the PHUSION® site-directed mutagenesis kit (NEB), to construct pMD-TV. Sequences of the primers used to construct pMD-TV are provided in Table C, below.

TABLE C

| Primers used to construct pMD-TV | |
|---|---|
| Primer name | Sequence[a] |
| prMD31.pGB.2.F.Nsi | TCATATATGCATTAATGTCTAACAATTCGTTCAAGCC (SEQ. ID NO: 5) |
| prMD32.pGB2.R.NheI | CTACACGCTAGCACGCTACTTGCATTACAGCTTACG (SEQ. ID NO: 6) |
| prMD33.KD.F.NheI | TAGCGTGCTAGCGTGTAGGCTGGAGCTGCTTCG (SEQ. ID NO: 7) |
| prMD34.KD.R.NsiI | ACATTAATGCATATATGAATATCCTCCTTAGTTCCTATT CCG (SEQ. ID NO: 8) |
| prMD35.pGB.MCS.F.p | TCGAGGGGCGCGCCGGTACCGAATTCCCGACAGTAAGA CGG (SEQ. ID NO: 9) |
| prMD36.pGB.MCS.R.p | GCCCGGGGATCCGCGGCCGCGTCGACCTGCAGCCAAGC TT (SEQ. ID NO: 10) |
| prMD58.tviD.F | GATCGGCTAGCCCGTTCCTCATTGATTTGATTGC (SEQ. ID NO: 11) |
| prMD59.tviD.R | GATCGCCCGGGTTACGACTTCCCTGATGTATTTTTTTGT AATG (SEQ. ID NO: 12) |
| prMD60.vexA.F | GATCGCTCGAGTAATTAATGGGCATCATTTTTCAGCTAT TTC (SEQ. ID NO: 13) |
| prMD83.vexA.R.xhoI.1000 | GATCGCTCGAGTTAGAAAGAATTAGTGCCGCGGG (SEQ. ID NO :14) |
| prMD75.mcs.F.p | CGGTCTCGAGGGGCGCGCCGGTACCGAATTCTAATTAA TGGGCATCATTTTTCAGCTATTTC (SEQ. ID NO: 15) |
| prMD76.mcs.R.p | GTGGATCCAAGCTTGCGGCCGCCCGTCGACAGTAAAGC CCTCGCTAGATTTTAATGCG (SEQ. ID NO: 16) |
| prMD77.sites.remove.F.p | CCGACAGTAAGACGGGTAAGCC (SEQ. ID NO: 17) |
| prMD78.sites.remove.R.p | TTAGAAAGAATTAGTGCCGCGGG (SEQ. ID NO: 18) |

[a]Restriction sites are underlined.

Part of wzz (orf 3) through orf 7 was PCR-amplified (labeled fragment A in FIG. 1) and cloned into pMD-TV.

Cloning *S. sonnei* O-Antigen Genes into pMD-TV

*S. sonnei* O-antigen genes were PCR-amplified from pXK65 (Xu et al. (2002) *Infect. Immun.*, 70:4414-4423). Primers prMD43.ss.F.HindIII, gatcaaagcttgatcaaatagctcatat tcagcg (SEQ ID NO:19), and prMD44.ss.BamHI.R, gatca ggatcctgctcagtccggttggtg (SEQ ID NO:20), were used to amplify part of the wzz gene (orf3) through wzy (orf7), shown as fragment A in FIG. 1. The resulting PCR product and pMD-TV were digested with HindIII and BamHI, PCR purified (QIAGEN®) and ligated using T4 ligase. Primers prMD41.ss.F.BamHI, gtagcggatccaagcgcagctatttaggatgag (SEQ ID NO:21), and prMD42.ss.R.XhoI, gatcg ctcgagttaatttacggggtgattaccagac (SEQ ID NO:22), were used to amplify genes wbgV (orf9) through apqZ (orf 14), shown as fragment B in FIG. 1. The resulting PCR product and plasmid pMD-TV containing genes wzz to wzy (orf3 to orf7) were digested with BamHI and XhoI, PCR-purified, and ligated as before to construct pMD-TV-Ss-1. Thus, orfs 9 to 14 (labeled fragment B in FIG. 1) were PCR-amplified, eliminating the non-essential IS630 element (orf8), and this amplicon was attached to cloned fragment A in pMD-TV to generate pMD-TV-Ss-1.

The plasmid was observed to express *S. sonnei* form I O-antigen in either *E. coli* or Ty21a, as determined by slide agglutination with form I-specific antisera. Also, LPS purified from *E. coli* or Ty21a carrying pMD-TV-Ss-1 reacted with specific form I antibody in Western immunoblotting studies (FIG. 2), demonstrating that IS630 (orf8) is not essential for form I O-antigen biosynthesis.

Example 2. Integration into the Ty21a Chromosome of Linear *Shigella* DNA

Datsenko and Wanner (Datsenko et al. (2000) *Proc. Natl. Acad. Sci. USA,* 97:6640-6645) previously described a method based on the highly efficient λ phage red recombination system that enables one to create specific targeted gene mutations via recombinational replacement of an *E. coli* chromosomal sequence with a small selectable antibiotic resistance gene that is generated by PCR using primers containing 36 to 50 bp extensions that are homologous to the gene targeted for mutation. The λ red system includes β, γ, and exo genes, whose products are called Beta, Gam, and Exo, respectively (Murphy (1998) *J. Bacteriol.,* 180:2063-2071). Gam inhibits the host RecB,C,D exonuclease and the SbcC,D nuclease activities, so that exogenously added linear DNA is not degraded. The Exo protein is a dsDNA-dependent exonuclease that binds to the terminus of each strand while degrading the other strand in a 5' to 3' direction. Beta binds to the resulting ssDNA overhangs, ultimately pairing them with a complementary chromosomal DNA target (Sawitzke et al. (2007) *Methods Enzymol.,* 421:171-199).

The low copy plasmid pKD20 encodes these three λ red proteins under the control of the arabinose-inducible $P_{araB}$ promoter, has an optimized ribosome-binding site for efficient translation of the β, γ, and exo genes, and has a temperature-sensitive replicon to allow for its easy elimination (Datsenko et al. (2000) *Proc. Natl. Acad. Sci. USA,* 97:6640-6645). The λ red system has been widely utilized for specific gene inactivation in *E. coli, Salmonella* and *Shigella* species, and for introducing small biological tags (Uzzau et al. (2001) *Proc. Natl. Acad. Sci. USA,* 98:15264-15269) or single genes into these chromosomes (Yu et al. (2011) *Appl. Microbiol. Biotechnol.,* 91:177-188).

In this study, the lengths of the homologous extensions needed for detectable lambda-Red mediated recombination of large blocks of foreign DNA (≥15,000*bp) into a targeted site in the desired chromosome were increased in a stepwise fashion from 50 to 150 bp and then to 500-1000 bp. In order to integrate the large form 1 O-antigen operon into the chromosome of vaccine strain Ty21a, a new plasmid, pMD-TV, was constructed.

As depicted in FIG. 1, the optimal chromosome insertion vector pMD-TV consists of a replicon plus a multiple cloning site (MCS) and an adjacent selectable $Kan^r$ cassette, which can be removed, when desired, via special recombination between flanking FRT sites. In addition, the MCS plus removable $Kan^r$ cassette are flanked by two large regions (500-1000 bp) of targeted homology with the Ty21a chromosome. The homologous regions chosen are tviD (~500 bp) and vexA (1000 bp) located within the non-expressed Vi capsule locus of Ty21a. The minimal essential *S. sonnei* O-antigen gene region was cloned into the MCS of pMD-TV to construct pMD-TV-Ss-1, the PCR template for subsequent chromosome recombineering. The resulting PCR amplicon, containing the *S. sonnei* O-antigen genes, is 15,532 bp.

Bacterial Strains, Plasmids, and Growth Conditions

The bacterial strains and plasmids utilized herein are described in Table D, below. *E. coli* strains were grown at 37° C. in Luria-Bertani (LB) broth or on LB agar from DIFCO®. *Shigella* strains were grown in tryptic soy broth (TSB) or tryptic soy agar (TSA) from DIFCO®. *Salmonella* strain Ty21a was grown in TSB or TSA supplemented with 0.01% galactose and 0.01% glucose. Plasmid-containing strains were selected in growth medium containing ampicillin (Amp; 100 μg/ml), spectinomycin (Spc; 100 μg/ml), chloramphenicol (Cm; 35 μg/ml), or kanamycin (Kan; 30 μg/ml). All constructed plasmids were sequenced, and the sequences were assembled and analyzed by using the VECTOR NTI® suite 9.0 software (Invitrogen).

TABLE D

Bacterial strains and plasmids

| Strain or plasmid | Genotype or description | Reference or source |
|---|---|---|
| | Strains | |
| *E. coli* DH5α | supE44 hsdR17 recA1 endA1 gyrA96 thi-1 relA1 | New England Biolabs |
| *S. enterica* serovar *Typhi* Ty21a | galE ilvD viaB (Vi-) $H_2S$- | (Germanier and Fuer, 1975) |
| *S. flexneri* 2a 2457 | | Lab stock |
| *S. flexneri* 3a J99 | | Lab stock |
| Ty21a-Ss (MD77) | *S. sonnei* O-antigen genes integrated into tviD-VexA on the chromosome, $Kan^s$, $Amp^s$, $Cm^s$ | This study |

TABLE D-continued

Bacterial strains and plasmids

Figure 3:
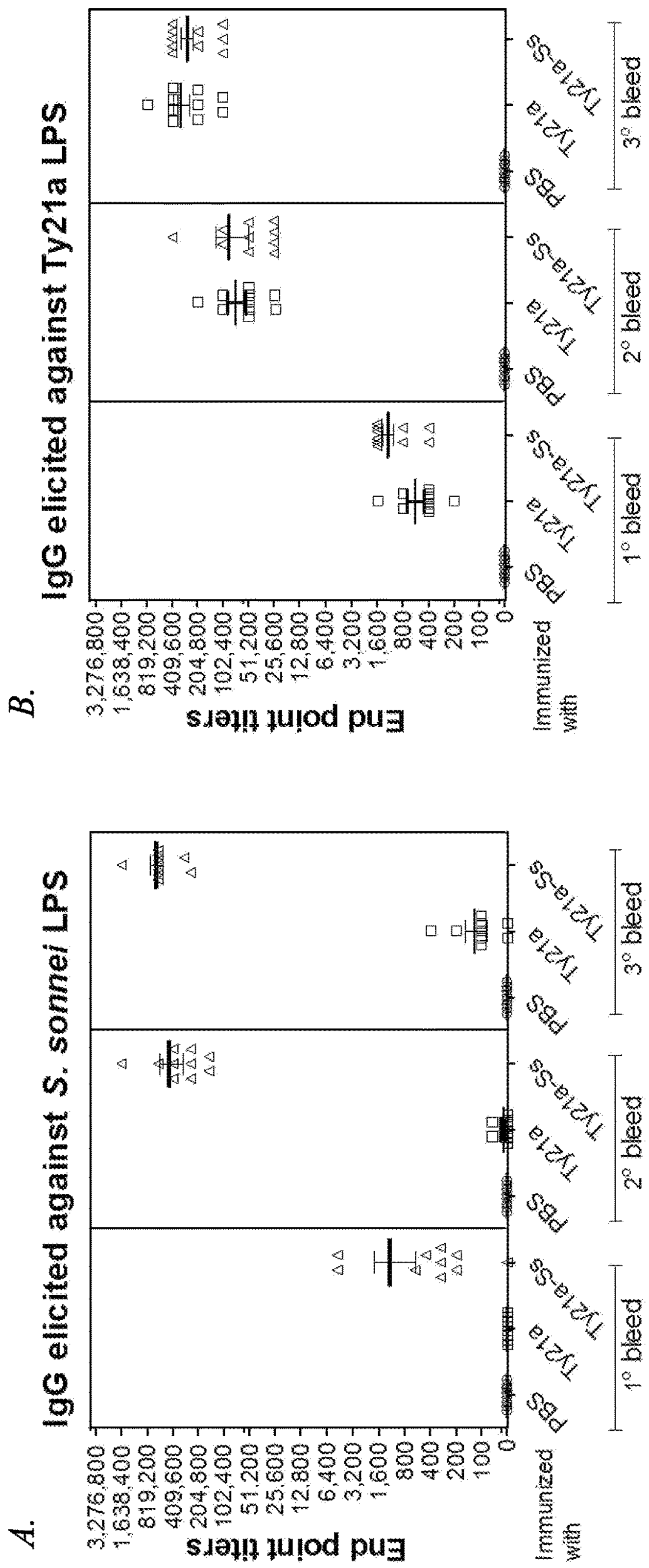
FIG. 3 shows bar graphs depicting mouse serum IgG responses, measured by ELISA, to *S. sonnei* LPS (FIG. 3A) and Ty21a LPS (FIG. 3B) after intraperitoneal immunization of mice with PBS, Ty21a, or vaccine strain Ty21a-Ss simultaneously expressing both Ty21a LPS and *S. sonnei* LPS. ELISA plates were coated with *S. sonnei* LPS or Ty21a LPS and blocked with 1% BSA. Serial dilutions of serum collected from vaccinated mice were added to the microtiter wells, washed, and LPS-bound IgG antibodies were detected using anti-mouse IgG-HPR. End point titers for the three groups of mice that received PBS, Ty21a, or Ty21a-Ss are shown following 1, 2, or 3 vaccine doses. Each symbol represents a single mouse, and bars represent the mean±SEM of each group of 10 mice.
Figure 4:
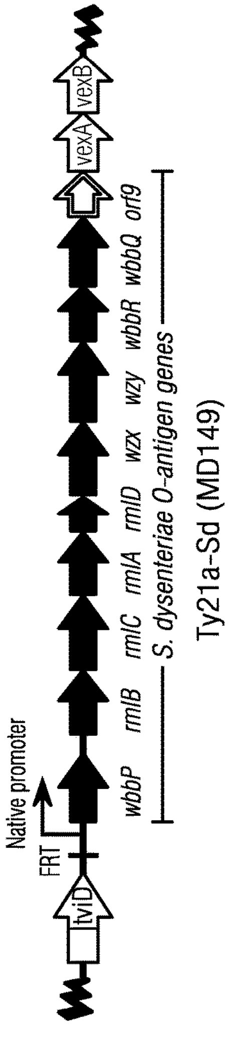
FIG. 4 shows a schematic diagram depicting *S. dysenteriae* biosynthetic genes integrated into Vi capsule operon of Ty21a vaccine strain.
Figure 5:
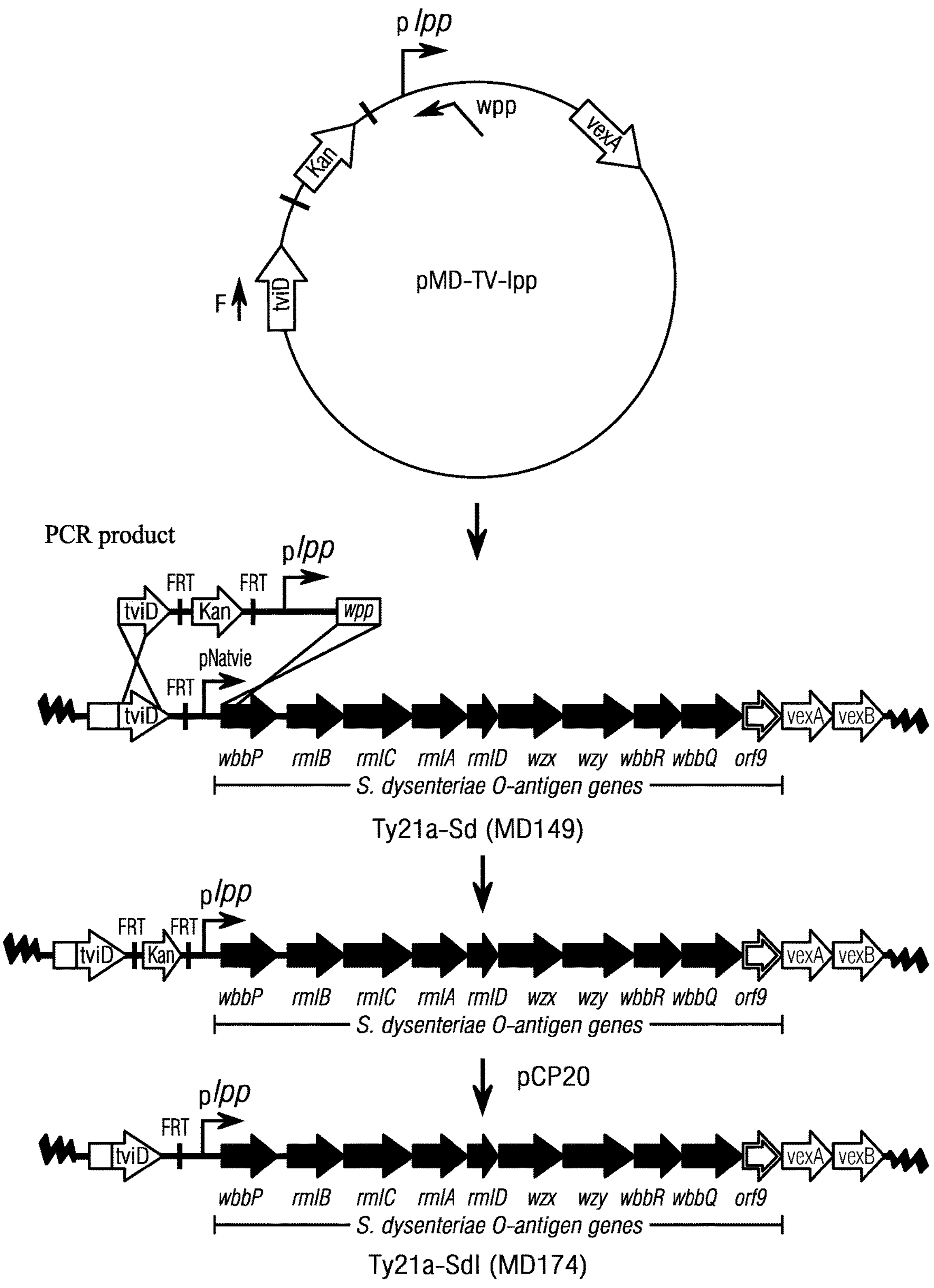
FIG. 5 provides a schematic representation of the cloning and chromosomal integration of *S. dysenteriae* O-antigen genes. The figure shows how the lpp promoter was inserted to replace the native promoter.
Figure 14:
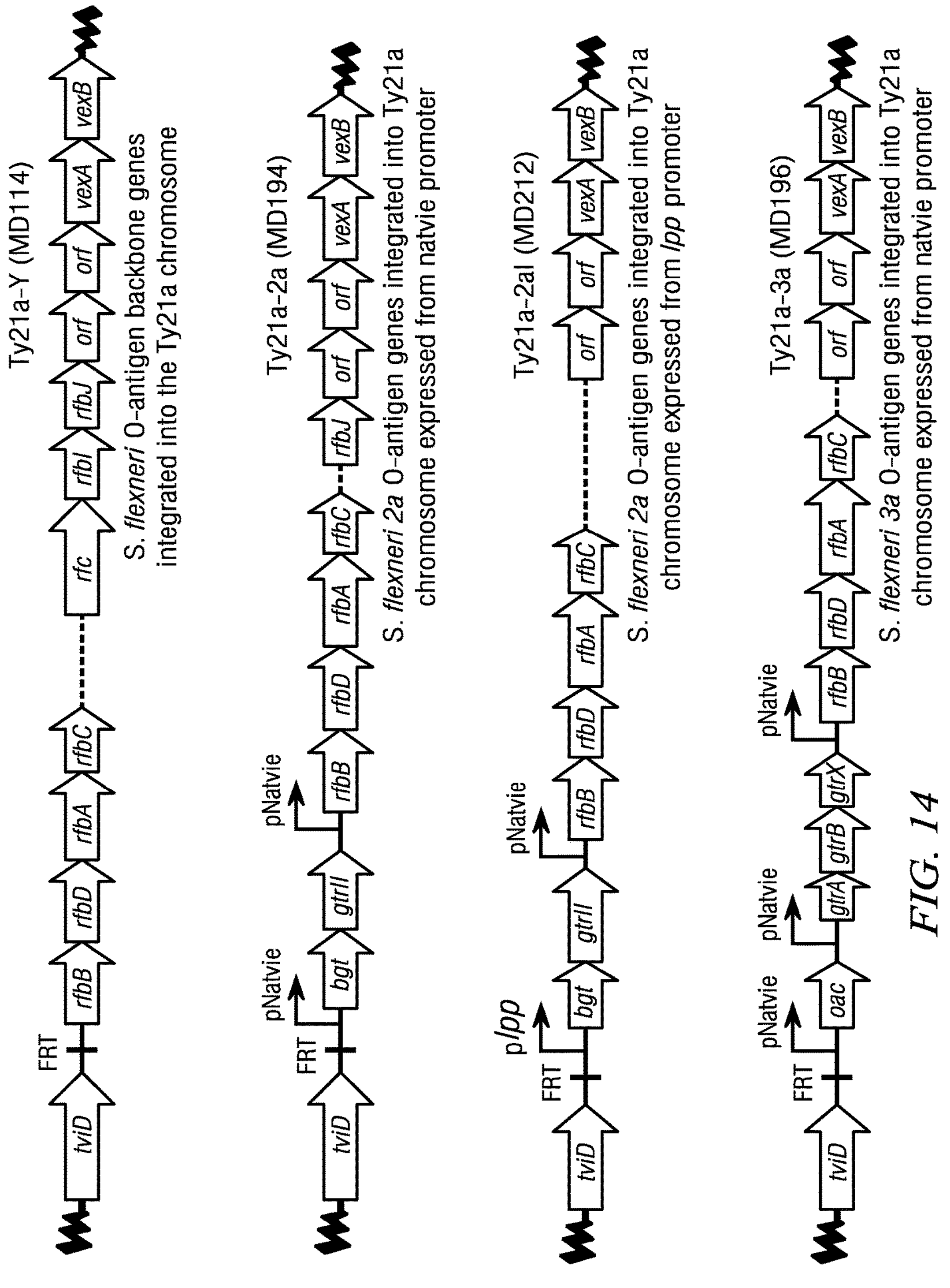
FIG. 14 provides schematic representations of Ty21a-Y (MD114), Ty21a-2a (MD194), Ty21a-2al (MD212), and Ty21a-3a (MD196).

| Strain or plasmid | Genotype or description | Reference or source |
|---|---|---|
| Ty21a-Ss-Kan (MD67) | *S. sonnei* O-antigen genes integrated into tviD-VexA on the chromosome, $Kan^r$, $Amp^s$, $Cm^s$ | This study |
| Ty21a-Sd (MD149) | *S. dysenteriae* O-antigen genes integrated into tviD-VexA on the chromosome, expressed from lpp promoter, $Kan^s$, $Amp^s$, $Cm^s$ | This study, FIG. 4 |
| Ty21a-Sd1 (MD174) | *S. dysenteriae* O-antigen genes integrated into tviD-VexA on the chromosome, expressed from lpp promoter, $Kan^s$, $Amp^s$, $Cm^s$ | This study FIG. 5 |
| Ty21a-Y (MD114) | *S. flexneri* rfb operon integrated into tviD-vexA on the chromosome, expressed from native promoter, $Kan^s$, $Amp^s$, $Cm^s$ | This study FIG. 14 |
| Ty21a-2a (MD194) | *S. flexneri* 2a O-antigen genes integrated into tviD-vexA on the chromosome, expressed from native promoter, $Kan^s$, $Amp^s$, $Cm^s$ | This study FIG. 14 |
| Ty21a-3a (MD196) | *S. flexneri* 3a O-antigen genes integrated into tviD-vexA on the chromosome, expressed from native promoter, $Kan^s$, $Amp^s$, $Cm^s$ | This study FIG. 14 |
| Ty21a-2a1 (MD212) | *S. flexneri* 2a O-antigen genes integrated into tviD-vexA on the chromosome, expressed from lpp promoter, $Kan^s$, $Amp^s$, $Cm^s$ | This study FIG.3 14 |
| *S. dysenteriae* type 1 1617 | Virulent strain | (Mendizabal-Morris et al., 1971; Neill et al., 1988) |
| 1617ΔstxA | Deletion of most of stxA of strain 1617 | (Xu et al., 2007) |
| *S. sonnei* 53GI | Form I (phase I), virulent isolate | (Kopecko et al., 1980) |
| | Plasmids | |
| pGB-2 | pSC101 derivative, low-copy plasmid; $Sm^r$, $Spc^r$ | (Churchward et al., 1984) |
| pKX65 | *S. sonnei* genes cloned into pGB-2 | (Xu et al., 2002) |
| pXK65 | pGB-2 containing the cloned Rfb region of *S. sonnei* | (Xu et al., 2002 |
| pKD4 | $Kan^r$ flanked by FRT sites, $Amp^r$, oriR6Kgamma | (Datsenko and Wanner, 2000) |
| pKD46 | Gam-beta-exo proteins under the control of arabinose promoter, ts-rep[a], $Amp^r$ | (Datsenko and Wanner, 2000) |
| pCP20 | yeast Flp recombinase gene FLP, $Cm^r$, $Amp^r$, ts-rep[a] | (Cherepanov and Wackernagel, 1995) |
| pMD35-36 | pSC101 derivative, low-copy plasmid, $Kan^r$ flanked by FRT | This study |
| pMD-TV | pSC101 derivative, low-copy plasmid, $Kan^r$ flanked by FRT, containing homologous regions for Ty21a tviD and vexA genes | This study |
| pMD-TV-Ss-1 (SEQ ID NO: 24) | *S. sonnei* O-antigen genes cloned into pMD-TV | This study |
| pMD-TV-Sd-4 | *S. dysenteriae* 1 O-antigen genes cloned into pMD-TV | This study |
| pMD-TV-lpp | lpp promoter cloned into pMD-TV | This study |

[a]ts-rep; temperature sensitive replication

Chromosomal Integration of O-Antigen Genes

The *S. sonnei* O-antigen biosynthetic genes described above, engineered between 500-1000 bp regions of Ty21a chromosome homology to enhance recombination efficiency, were integrated into the Ty21a chromosome using λ red recombination (Datsenko et al. (2000) *Proc. Natl. Acad. Sci. USA,* 97:6640-6645). Ty21a was transformed with pKD46 and grown at 30° C. in TBS-Amp supplemented with 0.01% galactose and 0.01% glucose and induced with L-arabinose until $OD_{600}$=~0.7. The resulting cells were made electrocompetent by washing with 10 mM Hepes and 10% glycerol and concentrating 500-fold by centrifugation. As shown in FIG. 1, pMD-TV-Ss—was used as a template with the tviD forward primer and vexA reverse primer for PCR amplification. This PCR-amplified region contains part of the tviD gene, a $Kan^r$ gene flanked by FTR sites, a genetically-minimized set of essential *S. sonnei* O-antigen biosynthetic genes, and the vexA gene.

The PCR product was DpnI-digested to remove circular plasmid DNA, was purified, and ~1-2 μg was transformed into freshly grown electrocompetent cells of Ty21a expressing λ red proteins. Thus, the linear ds-DNA amplicon was used to transform competent Ty21a cells expressing the λ red proteins from pKD46.

Transformants for the above-described amplicon were selected for $Kan^r$; the transformed cells were recovered by growing in SOC media at 30° C. and plating on TSA-Kan plates. Of note, the above PCR products were DpnI-digested to remove any remaining circular plasmids. Despite this step, a few copies of plasmid inevitably escaped DpnI-digestion and generated $Kan^r$ transformants. These plasmid transformants can then recombine at either chromosomal region of homology, creating unstable merodiploids, making molecular characterization confusing, because PCR results reflect a mixture of possibilities. After primary selection with antibiotic, mutants were maintained on medium without an antibiotic. Isolates were colony-purified once non-selectively at 37° C. and then tested for ampicillin sensitivity to demonstrate loss of plasmid pKD46.

To detect appropriate chromosomal integrants (i.e., containing 15,532 kb inserts of *S. sonnei* form 1 genes inserted between tviD and vexA), DNA from individual transformants was subjected to PCR using primers prMD92 and prMD124 (FIG. 1) recognizing Ty21a sequences just upstream and downstream of the targeted integration site. Colonies were further analyzed by PCR to confirm chromosomal integration with primers prMD92, GTTGCGGTAATGGTATAACGAAATAACAGATAC (SEQ ID NO:25) and prMD124, CACGCAATATTTCAATGATGGCAAC (SEQ ID NO:26), as shown in FIG. 1. Furthermore, expression of the form 1 O-antigen was confirmed by slide-agglutination and Western immunoblot with form 1-specific antisera. (DIFCO®-BBL). The wild-type Ty21a sequence, in the integration region tviD-tviE-vexA, detected by using primers prMD92 and prMD124, generated a ~4 kb band. Undesired integration of the whole plasmid into the Ty21a chromosome at tviD and/or vexA could also be detected by PCR.

Next, the desired $Kan^r$ chromosomal integrants of linear *S. sonnei* DNA were transformed with temperature-sensitive plasmid pCP20, which expresses the FLP recombinase, to eliminate the FRT-flanked $Kan^r$ cassette. In brief, chromosomal integrants expressing $Kan^r$ were transformed with pCP20 (Cherepanov et al. (1995) *Gene,* 158:9-14), and $Cm^r$ transformants were selected at 30° C., after which a few isolates were colony-purified non-selectively at 37° C. and then tested for loss of all antibiotic resistances.

Antibiotic-sensitive chromosomal integrants were further analyzed by PCR to demonstrate deletion of the Kan cassette. Furthermore, the final PCR products generated from primers prMD92 and prMD124, were sequenced entirely. When the chromosomally integrated Ty21a-Ss sequence was compared to the GENBANK® *S. sonnei* O-antigen gene cluster AF294823 (SEQ ID NO:23), only a single change ($E_{273}$K) was detected in wbgZ (orf13 in FIG. 1), which had no apparent effect on O-antigen expression, as determined by slide agglutination and western blotting of resulting LPS.

Example 3. Two-Year Ear Studies to Attain Stable Expression of the Approximately 12 kb *Shigella sonnei* O-Antigen Gene Region Via Recombinational Insertion into the Chromosome of Vaccine Vector Strain *Salmonella Typhi* Ty21a Expression in Low Copy Plasmid Vector

*S. sonnei* O-antigen genes were cloned into the low copy plasmid pGB-2, and this heterologous O-antigen was stably expressed in vaccine vector Ty21a, with only a 2% loss after 60 generations. This plasmid contains a spectinomycin-resistance gene cassette for genetic selection purposes. In contrast, high copy plasmid vectors, containing this cloned *Shigella* region were not genetically stable (3). Although pGB-2 appeared suitably stable, the spectinomycin-resistance gene needed to be removed.

Achieving Stable Expression after Removal of Antibiotic Cassette

*S. sonnei* genes on pGB-2 were stably expressed with 98% stability for 60 generations of growth in the absence of antibiotics. For FDA regulatory purposes, however, the antibiotic resistance cassette needs to be removed prior to administration of the vaccine to humans on a large scale. Thus, attempts were made to remove the resistance gene cassette by deletion using targeted restriction endonucleases, by deletion using recombination techniques or PCR-generated deletions. Regardless of the method used or the length of the region deleted, removal of the antibiotic cassette resulted, unexpectedly, in plasmid instability. Plasmid loss over 60 generations reached 50%. The spectinomycin cassette was then replaced with a kanamycin-resistance gene cassette flanked by FRT sites. If the kanamycin-resistance could be removed via recombination between FRT sites, perhaps the resulting plasmid would be genetically stable. However, removal of kanamycin-resistance also resulted in plasmid instability.

Construction of pMD35-36 for Chromosomal Integration of O-Antigen Genes

In order to achieve stable expression of heterologous *Shigella sonnei* O-antigen genes in Ty21a in the absence of an antibiotic resistance cassette, the O-antigen genes were integrated into the Ty21a chromosome. To facilitate this task, the low copy plasmid pMD35-36 was constructed to contain a kanamycin-resistance gene cassette, flanked by FRT sites, and located adjacent to a multiple cloning site (MCS) locus. In addition, the kanamycin-resistance cassette, FRT sites, and MCS locus were synthesized by PCR from this plasmid using primers containing regions of homology to the Ty21a chromosome for recombinational insertion. The Ty21a tviD and vexA gene regions were used for homology. They are located adjacent to each other in the Vi capsule biosynthesis operon, which is nonfunctional in Ty21a.

Cloning *S. sonnei* Genes into pMD35-36

Essential genes of the *S. sonnei* O-antigen operon (eliminating a non-essential IS630 element) were cloned into plasmid pMD35-36 in two steps.

Optimizing Lambda Red Expression in Ty21a

Datsenko and Wanner (2000) (Datsenko et al. (2000) *Proc. Natl. Acad. Sci. USA,* 97:6640-6645) previously described a method based on the highly efficient lambda phage red recombination system that enables one to create mutations within a targeted gene via recombinational replacement of a chromosomal sequence with a selectable antibiotic resistance gene that is generated by PCR, using primers with 36 to 50 bp extensions that are homologous to the gene targeted for mutation. Lambda red proteins are expressed from plasmid pKD46, and the expression is tightly regulated through an arabinose-inducible promoter. This lambda red system has been widely utilized for specific gene inactivation in *E. coli, Salmonella* and *Shigella* species (Kotloff et al. (1999) *Bull. WHO,* 77:651-666), and for introducing small biological tags (Kewon (2008) *Curr. Opin. Infect. Dis.,* 21:313-318).

To facilitate chromosomal insertion, the *S. sonnei* O-antigen genes were cloned into plasmid pMD35-36, as described above. Initially, 50 bp regions of chromosomal homology to tviD and vexA were used. PCR amplification of this large recombinational construct resulted in a ~13.5 kb fragment, which includes the *S. sonnei* O-antigen biosynthetic genes, the kanamycin-resistance gene cassette flanked by FRT sites, all contained within two regions of chromosomal homology, consisting of 50 bp homology to tviD and vexA. This PCR product was transformed into Ty21a cells containing pKD46. No anticipated chromosomal inserts, detected as kanamycin-resistant colonies, were obtained, even when this experiment was repeated. As an experimental control, attempts were made to insert the smaller 1.5 kb kanamycin-resistance gene cassette, without any *Shigella* sequences included. This also resulted in failure. This result was unexpected, as the smaller 1.5. kb $Kan^R$ insert fragment should have integrated into the chromosome.

Based on a hypothesis that this lack of success might be due to insufficient lamda red recombinant protein expression in *Salmonella Typhi* Ty21a (the published conditions for lambda red expression (i.e., 1 mM arabinose) in *Salmonella* (Kewon (2008) *Curr. Opin. Infect. Dis.,* 21:313-318) and *E. coli* (Kotloff et al. (1999) *Bull. WHO,* 77:651-666) were not successful in Ty21a), higher arabinose concentrations of 2 mM, 10 mM, or 25 mM were attempted and found to be insufficient to express lambda red proteins from pKD46 in Ty21a, as detected by chromosomal integration of the 1.5 kb kanamycin-resistance cassette. This result was very unexpected.

Finally, a 100-fold increase in the recommended 1 mM concentration of arabinose was tried, and it was found that 100 mM was needed to generate sufficient lambda red expression in Ty21a to facilitate chromosomal insertion of the small 1.5 kb kanamycin-resistance gene cassette, using 50 bp regions of chromosomal homology. However, the large 13.5 kb PCR product containing the *S. sonnei* O-antigen biosynthetic genes was not integrated into the chromosome.

Homology Extensions Increased to 150 Bases

In order to facilitate chromosomal integration of the larger insert, the chromosomal homology extensions on the PCR primers were increased from 50 to 150 bases each. Although these increased regions of homology facilitated chromosomal insertion of the 1.5 kb kanamycin-resistance cassette at an enhanced frequency, the large 13.5 kb PCR product failed to integrate into the chromosome after several attempts. This result was also unexpected, since general recombination usually proceeds with 50-100 bp of homology, and lambda Red-mediated recombination is usually more efficient than bacterial general recombination.

Construction of Chromosomal Insertion Plasmid pMD-TV

The use of large 500-1000 bp regions of homology required cloning these regions into the chromosomal insertion plasmid. First, Ty21a genomic DNA was prepared. Next, the vexA gene (~1000 bp) and part of the tviD gene (~500 bp) were PCR-amplified from Ty21a genomic DNA. These two PCR amplicons were cloned into pMD35-36 in separate steps. In addition, the MCS locus was further changed to contain new and different restriction sites. This resulted in the construction of a new chromosomal insertion vector, pMD-TV, containing 500-1000 bp arms of chromosomal homology. These longer arms were engineered to increase the area of homology with the Ty21a chromosome and thus increase the chances for integration of large DNA regions (i.e., greater than 5 kb).

Cloning *S. sonnei* Genes into pMD-TV

Essential genes of the *S. sonnei* O-antigen biosynthetic operon were cloned in two steps into the plasmid pMD-TV, eliminating a nonessential IS630 element.

Optimizing Competent Cells

After the *S. sonnei* genes were cloned into the new pMD-TV plasmid, a 15.5 kb PCR product, which contains the kanamycin-resistance cassette, the *S. sonnei* O-antigen genes, and the arms of Ty21a homology, was transformed into Ty21a expressing the lambda red proteins. Unexpectedly, no transformants were achieved, even after exhaustive plating and a repeat experiment. In order to address the question of whether the transformation efficiency of the large linear DNA fragment was too low, fresh competent Ty21a cells were further optimized by increasing the number of final washes from two to three, increasing the number of cells in each transformation reaction, and also increasing the amount of linear DNA added per reaction to about 1-2 μg. These changes allowed for the successful chromosomal integration into Ty21a of the large 13.5 kb fragment encoding the heterologous *S. sonnei* O-antigen. (Datsenko et al. (2000) *Proc. Natl. Acad. Sci. USA,* 97:6640-6645; Uzzau et al. (2001) *Proc. Natl. Acad. Sci. USA,* 98:15264-15269; Xu et al. (2002) *Infect. Immun.,* 70:4414-4423).

Figure 2:
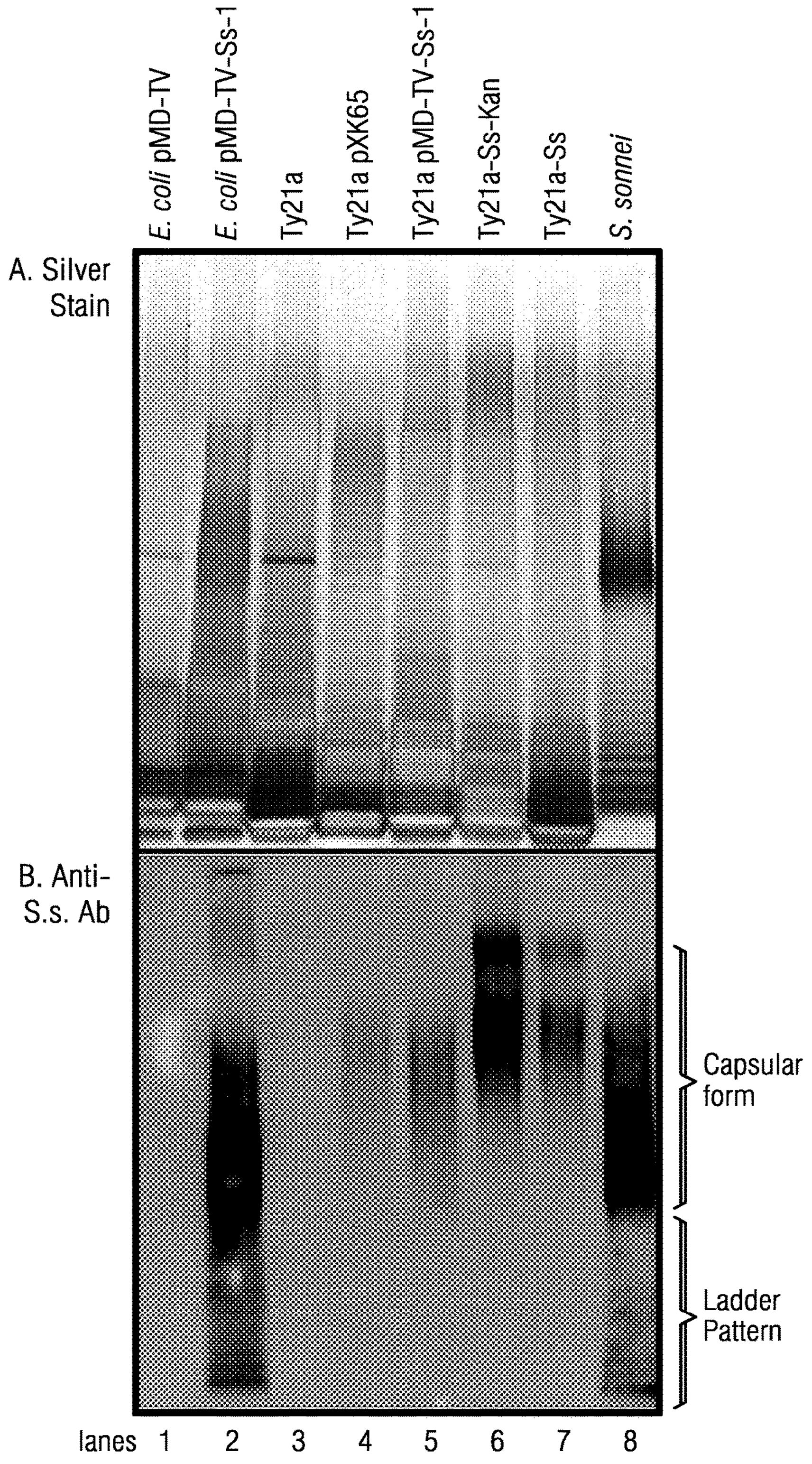
FIG. 2 shows the results of analyses of SDS-PAGE-separated polysaccharide isolated from various *Shigella sonnei, E. coli*, and Ty21a isolates by, in Panel A, silver staining and in Panel B, Western immunoblotting with form 1-specific antibody.

Example 4. O-Antigen Expression Determined by Silver Staining and Immunoblotting. LPS Analysis by Silver-Stain and Western Immunoblotting was Employed to Examine LPS Expression in Parent and Recombinant Strains Expressing Heterologous O-Antigen O-Antigen Expression Analyses Slide agglutination reactions were performed with rabbit polyclonal antisera against *S. sonnei* (phase I) or against *Salmonella Typhi* O-specific 9 factor (DIFCO®). For immunoblotting, *Salmonella, Shigella* and *E. coli* strains with or without various recombinant plasmids were grown overnight with aeration at 37° C. in media containing appropriate antibiotics. LPS was purified using an LPS extraction kit (Bocca Scientific) according to the manufacturer's instructions. Purified LPS was separated by Tris-glycine PAGE. Standard Western blotting procedures were carried out with the above antibodies for identification of specific LPS types. Silver-staining analysis was performed using the SILVERXPRESS® Silver Staining Kit (Invitrogen) according to the manufacturer's instructions. As revealed by silver-staining of isolated polysaccharide separated by SDS-PAGE (FIG. 2, Panel A), *E. coli* DH5α, a rough mutant (lane 1), was observed to express *S. sonnei* O-antigen as both an LPS ladder and a slower-migrating Group 4 capsule (lane 2). Ty21a (lane 3) was found to produce a typical 9,12 LPS short ladder pattern, which is altered both by the addition of an extended form 1 LPS ladder pattern and slower-moving form 1 O-antigen capsule expression (lanes 4, 5, 6, 7). Wild-type *S. sonnei* was observed to express a form 1 LPS ladder pattern, the majority topping out at a chain length of ~20 O-repeats, by silver stain analysis (FIG. 2, Panel A, lane 8).

Western immunoblotting (FIG. 2, Panel B) showed specific antibody reaction with form 1 polysaccharide in all strains expressing *S. sonnei* O-antigen, regardless of whether the form 1 genes were carried by plasmids (i.e., pXK65, pMD-TV-Ss-1) or integrated into the Ty21a chromosome [i.e., Ty21a-Ss (or MD77) Ty21a-Ss-Kan (or MD67)]. Although a form 1 LPS ladder pattern was easily visible in *E. coli* (FIG. 2, Panel B, lane 2) and wild-type *S. sonnei* (lane 8), the majority of form 1 O-antigen in all expressing isolates appeared to be the slower migrating group 4 capsule expression. As noted below, Form 1 O-antigen was highly immunogenic regardless of expression as LPS or in capsular form (FIG. 3).

Example 5. Stability of Heterologous Form 1 O-Antigen Expression in Ty21a

Stability of recombinant clones of Ty21a-Ss expressing *S. sonnei* O-antigen were tested by immunoblotting of colonies plated from an overnight culture (~24 hours), and it was diluted 1:100 and grown for an additional~24 hours. Colonies, transferred to a nitrocellulose membrane, were analyzed by standard Western blotting procedures using the LPS-specific antibodies specified above.

The new recombineered vaccine strain Ty21a-Ss, which is antibiotic-sensitive and contains chromosomally integrated form 1 biosynthetic genes, was grown at high dilution in TSB plus 0.01% galactose and 0.01% glucose without antibiotics for ~24 hours, which represents ~25 generations of growth. This culture was diluted 1:100 and grown for an additional ~24 hours, which represents 50 generations. The resulting cells were plated on TSA containing 0.01% galactose and 0.01% glucose, grown overnight at 37° C., and colony immunoblots were performed to examine form 1 expression, as described above. All of 500 colonies tested retained *S. sonnei* form I O-antigen expression, demonstrating 100% stability of the chromosomally integrated genes.

Example 6. Antibodies to Both *S. Typhi* and *S. sonnei* LPSs are Elicited in Mice Following Immunization with Ty21a-Ss Mice were immunized (3 doses IP spaced 2 weeks apart) with the recombineered vaccine strain Ty21a-Ss, the parent strain Ty21a or control PBS. Eight-week-old female Balb/c mice were immunized with vaccine candidate strains (Ty21a-Ss) or negative controls, Ty21a alone, and PBS. Ty21a-Ss and Ty21a controls were grown overnight in TSB supplemented with 0.01% galactose and 0.01% glucose, washed, and suspended in sterile PBS to a concentration of ~0.8-1.6×$10^8$ CFU per ml. They were tested one week after each dose for the presence of antibodies against *S. sonnei* or Ty21a LPS by ELISA, as described below. As shown in FIG. 3, immunization with Ty21a-Ss resulted in increased anti-LPS antibody titers after each dose, but peaked after 2 doses at very high titers of ~400,000 for anti-form 1 serum IgG, and after 3 doses at similarly high titers for anti-*Salmonella Typhi* LPS antibodies. These results further confirm the stable expression of both heterologous *S. sonnei* O-antigen and homologous Ty21a LPS in Ty21a-Ss. Moreover, the parent strain Ty21a elicited serum IgG antibodies that reacted only with Ty21a LPS, and were at essentially the same titer as that elicited by the recombinant Ty21a-Ss.

Example 7. Protection from Virulent *S. sonnei* Challenge Conferred by Ty21a-Ss

Mice are typically used to demonstrate immune stimulation by a *Salmonella Typhi* vaccine strain and to measure specific protection against parenteral challenge with virulent *Shigella*. Balb/C mice were immunized with Ty21a-Ss, Ty21a alone, or saline by the IP route with three doses of vaccine spaced two weeks apart. Mice were inoculated intraperitoneally with a 0.25-ml dose containing ~2-4×$10^7$ CFU per mouse of either vaccine, control Ty21a cells, or 0.25 ml sterile saline, for three total doses spaced two weeks apart. Mice were tail-bled one week after every injection. Two weeks following the last dose, mice were challenged i.p. with *S. sonnei* 53G at a dose of approximately 100× LD50. Immunized and control mice were challenged intraperitoneally, 2 weeks after final immunization, with 5×$10^6$ CFU/ml of freshly grown, mid-log-phase *S. sonnei* strain 53GI in 0.25 ml (2×$10^6$ CFU per mouse) of 5% hog gastric mucin (Sigma) dissolved in sterile saline (i.e., approximately 100 times the 50% lethal infectious dose [$LD_{50}$]). Survival was monitored for 72 h.

TABFE E

Mouse protection against virulent *S. sonnei* challenge

| Groups of 10 mice immunized with: | Survivors/total |
|---|---|
| Ty21a-Ss (strain MD 77) | 10/10 |
| Ty21a | 0/10 |
| Saline | 0/10 |

Detection of Anti-LPS Antibodies by ELISA

*S. sonnei* 53G Phase 1 was grown overnight at 37° C. with aeration in TBS while *S. Typhi* Ty21a-Ss was grown in TSB supplemented with 0.01% galactose and 0.01% glucose. LPS was purified using a LPS extraction kit (Bocca Scientific) according to the manufacturer's instructions. Microtiter plates were coated with *S. sonnei* (phase I) or *Salmonella Typhi* Ty21a purified LPS in 0.1 M $Na_2CO_3$/$NaHCO_3$ pH 9.5. Coated microtiter plates were blocked with blocking buffer containing 1% BSA (Sigma) in TBST (TBS with 0.5% tween-20) for two hours. Serial dilutions of serum were added to each plate and incubated at 4° C. overnight. After washing six times with TBST, bound antibodies were detected with HRP-conjugated goat anti-mouse IgG (SOUTHERNBIOTECH®). Endpoint titers were defined as the reciprocal of the antibody dilution for the last well in a column with a positive OD for each sample after subtracting the background. Background values were determined with pre-immunization sera, where the OD values of the pre-immunization sera were averaged and then doubled. This value was subtracted from the OD of all the wells containing titrations of every mouse serum sample. Each data point represents the average endpoint titer of two independent ELISAs performed for every mouse serum sample. The individual sample titers and the mean±SEM for each group of ten mice are shown in FIG. 3.

Sequences are available under GENBANK® accession numbers JX436480 for pMD-TV (SEQ ID NO:1) and JX436479 for Ty21a-Ss tviD-vexA region (SEQ ID NO:2). This stringent challenge resulted in 100% mortality in Ty21a alone- or saline-immunized mice. However, mice immunized with the recombineered vaccine strain Ty21a-Ss were 100% protected against the *S. sonnei* challenge.

Thus, disclosed herein are attempts to stabilize the expression of heterologous *S. sonnei* LPS antigens in oral vaccine vector Ty21a to create a candidate that will protect against both typhoid fever and shigellosis due to *S. sonnei*. Previous studies had shown that a cloned large block of *Shigella* LPS biosynthetic genes (i.e., 10-15 kb) was much more stable in the low copy plasmid pGB-2 than in high copy plasmid vectors (Xu et al. (2007) *Vaccine,* 25:6167-6175; Xu et al. (2002) *Infect. Immun.,* 70:4414-4423). When attempting to remove the antibiotic resistance selective marker in pGB-2, which removal would be required for human vaccine use, unexpected and unexplained genetic instability was encountered. For example, $Kan^r$ (kanamycin resistance) pGB-2 carrying the *S. sonnei* form 1 O-antigen biosynthetic genes was 95-98% genetically stable when grown for 60 generations in the absence of antibiotic selective pressure. However, removal of the antibiotic resistance gene function by insertion or small deletion resulted in a plasmid with ~60% genetic stability (unpublished data).

A recent study by Yu, et al. (2011) inserted small ~2 kb gene regions into the *Salmonella* chromosome. Thus, the λ red recombination system was modified to allow the introduction of large blocks of foreign DNA, more than 15 kb, into the chromosome of *Salmonella Typhi*, termed genomic super-recombineering. This task required expanding the size of the necessary homologous recombination regions from ~50 bp as originally proposed (Datsenko et al. (2000) *Proc. Natl. Acad. Sci. USA,* 97:6640-6645) to 500-1000 bp in order to increase the efficiency of recombination. These expanded regions of homology were engineered into plasmid vector pMD-TV, which was specifically created to insert large regions of DNA into a susceptible chromosome at a chosen, targeted integration site (i.e., in this case, the tviE gene region of the non-functional Vi gene locus of Ty21a was chosen). Furthermore, the expression of the λ red recombination proteins in Ty21a and the concentration of PCR-amplified DNA needed for efficient chromosomal insertion of this large amplicon had to be optimized. Utilizing this optimized genomic super-recombineering technique, the *S. sonnei* O-antigen genes were inserted into the Ty21a Vi gene locus. Heterologous *S. sonnei* O-antigen expression in this Ty21a-Ss chromosomal integrant is 100% genetically stable. Additionally, this method allows for the use of antibiotic selection during strain construction and removal of a FRT-bracketed antibiotic resistance gene after all genetic manipulations are completed. Of especial importance, this new vaccine candidate strain elicits robust serum IgG antibody responses against both heterologous *S. sonnei* form I LPS and homologous *Salmonella Typhi* LPS in mice and protects mice 100% against a lethal challenge dose of virulent *S. sonnei.*

This chromosomal super-recombineering method has allowed for the development of a much improved vaccine candidate that is 100% genetically stable. This technique can be applied to many different bacterial genera and can be used to insert different foreign antigens at multiple targeted chromosomal sites, after which the associated antibiotic resistance gene, used for efficient selection, can be removed. The cloning of the *S. dysenteriae* serotype 1 O-antigen essential biosynthetic genes on plasmid pGB-2 has been previously described (Xu et al. (2007) *Vaccine,* 25:6167-6175). The pGB-2 cloning of the *S. flexneri* 2a and 3a LPS regions has been undertaken to construct additional multivalent typhoid-shigellosis vaccine components. It is, thus, contemplated to make similar super-recombineered chromosomal insertions of, for example, minimal-sized LPS genes of *S. flexneri* 2a, *S. flexneri* 3a, and *S. flexneri* 6, each into a separate Ty21a strain. The final multivalent vaccine will consist of 5 different strains comprising a multifunctional vaccine for protection against enteric fevers (aimed at typhoid, but with moderate cross-protection against paratyphoid fevers) and the predominant causes of shigellosis, projected to protect against ~85% of shigellosis worldwide (Noriega et al. (1999) *Infect. Immun.,* 67:782-788). In an additional embodiment, other antigens are incorporated into Ty21a (or another suitable vector strain) for vaccine purposes (e.g. anthrax protective antigen, plague F1 and V antigens, viral antigens to protect against viral diseases, malaria antigens) or genetic constructs expressing anti-tumor proteins or siRNAs directed at inhibiting tumor growth and metastasis for anti-cancer therapeutic purposes.

Recent collaborative studies (Ohtake et al. (2011) *Vaccine,* 29:2761-2771) have led to the development of a formulation and foam-drying method that results in a temperature-stable, dried Ty21a vaccine that obviates the need for refrigeration during distribution/immunization and will extend the shelf life to 5 years or greater at 4° C., enhancing the potential value of this multifunctional enteric vaccine for use in travellers, the military, and in developing world populations.

Example 8. Cloning and Chromosomal Insertion of a Second LPS Locus—of *Shigella dysenteriae* O-Antigen Biosynthetic Genes Cloning *S. dysenteriae* O-Antigen Genes into pMD-TV

*S. dysenteriae* O-antigen genes were PCR-amplified from *S. dysenteriae* serotype 1 strain 1617 genomic DNA (Xu, et al. (2007) *Vaccine* 25:6167-6175). Primers prMD127.dy.F.HindIII gatcgaagcttggcattttttgtcatttttggatgc (SEQ ID NO:27) and prMD128.dy.R.wbbP.BamHI gatcg ggatccatcgatatggctgggtaaggtcatg (SEQ ID NO:28) were used first to amplify the wbbP gene. The resulting PCR product and pMD-TV were digested with HindIII and BamHI, PCR-purified, and ligated. Next, primers prMD129.F.BamHI gatcgggatcctaatgaaaatctga ccgaatg-taacgg (SEQ ID NO:29) and prMD130.R.EcoRI gatcg gaattctcacattaatgctaccaaaaagagtcgc (SEQ ID NO:30) were used to amplify the larger *S. dysenteriae* 1 rfb gene cluster. The resulting PCR product and plasmid pMD-TV-wbbP were digested with BamHI and EcoRI, PCR-purified, and ligated to construct pMD-TV-Sd-4.

Integrating *S. dysenteriae* O-Antigen Genes into the Ty21a Chromosome

The *S. dysenteriae* O-antigen biosynthetic genes that were cloned into plasmid pMD-TV to construct pMD-TV-Sd-4 were used as a template for PCR with the tviD forward primer and vexA reverse primer. The PCR-amplified region was 13,574 bp and contains part of the tviD gene, $Kan^r$ gene cassette flanked by FRT sites, *S. dysenteriae* O-antigen biosynthetic genes and the vexA gene. The PCR amplicon was transformed into Ty21a competent cells expressing λ red proteins from pKD46 and selected for Kan resistance as described (Dharmasena et al.). PCR with primers upstream and downstream of the site of integration, prMD92 and prMD124, resulted in a ~14.5 Kb $Kan^r$ insert band. After removing the $Kan^r$ cassette as previously described (Dharmasena et al.), antibiotic-sensitive chromosomal integrants were further analyzed by PCR for deletion of the $Kan^r$ cassette, and the PCR product (MD 149/Ty21a-Sd~13 Kb band) obtained from primers prMD92 and prMD124 was sequenced. The previously sequenced *S. dysenteriae* wpp gene (GENBANK® accession no. AY763519; SEQ ID NO:4) and that of the *S. dysenteriae* strain 1617 strain were identical except for two bases, where CA is changed to AC at position 619-620 in the strain 1617 wpp gene. No mutations were detected in the chromosomally inserted wpp in Ty21a-Sd strain. When the Ty21a-Sd chromosomal insert Rfb sequence was compared to the GENBANK® accession no. AY585348 (SEQ ID NO:3) for the *S. dysenteriae* 1617 strain Rfb O-antigen gene cluster, only a single A to G transition (N130D) was detected in the gene rmlD (FIG. 4), which did not affect O-antigen expression as determined by slide agglutination and ELISA expression studies.

Replacing the Wpp Native Promoter with lpp

The low copy plasmid pMD-TV is a pSC 101 derivative existing as ~5 copies per cell. Thus, the plasmid pMD-TV-Sd-4 in Ty21a has ~5 copies of S. dysenteriae O-antigen genes per cell, while Ty21a-Sd (MD149) [i.e., the strain with S. dysenteriae O-antigen genes integrated into the Ty21a chromosome] has only one copy of the *S. dysenteriae* O-antigen biosynthetic genes per cell. Note, from previous studies (Dharmasena, et al.), that the *S. sonnei* LPS:S. *Typhi* Ty21a LPS ratio, as assessed by ELISA, was approximately 1 in strains expressing the *S. sonnei* O-antigen genes from the Ty21a chromosome (Ty21a-Ss) compared to the same genes expressed from the pGB-2 plasmid (pMD-TV-Ss) in Ty21a. However, the *S. dysenteriae* LPS: *S. Typhi* Ty21a LPS ratio was considerably less than 1 in the strain expressing *S. dysenteriae* O-antigen genes from the chromosome (Ty21a-Sd, MD 149) than from the plasmid (pMD-TV-Sd-4 in Ty21a), as determined by ELISA. Thus, attempts were made to increase the *S. dysenteriae* LPS expression by replacing the native wpp promoter with the *Escherichia coli lpp promoter, which is a highly transcribed constitutively active promoter.* pMD-TV-lpp was used as a template for PCR with the tviD forward primer and the lpp promoter reverse primer containing a 150 bp wpp homology extension (prMD151.lpp.R

```
aggaatggcgcctgctttttttattatttccttggatgaatcattatagt cagtagcaaaagcatagactgaaatccctttcttggttagtgtttttatt aaatccaatctaaacaaaatcatagcatttgctgtgttccctattattga gatcttcatatgcctctcctttcattattaataccctctagagttc;

SEQ ID NO: 31).
```

Figure 6:
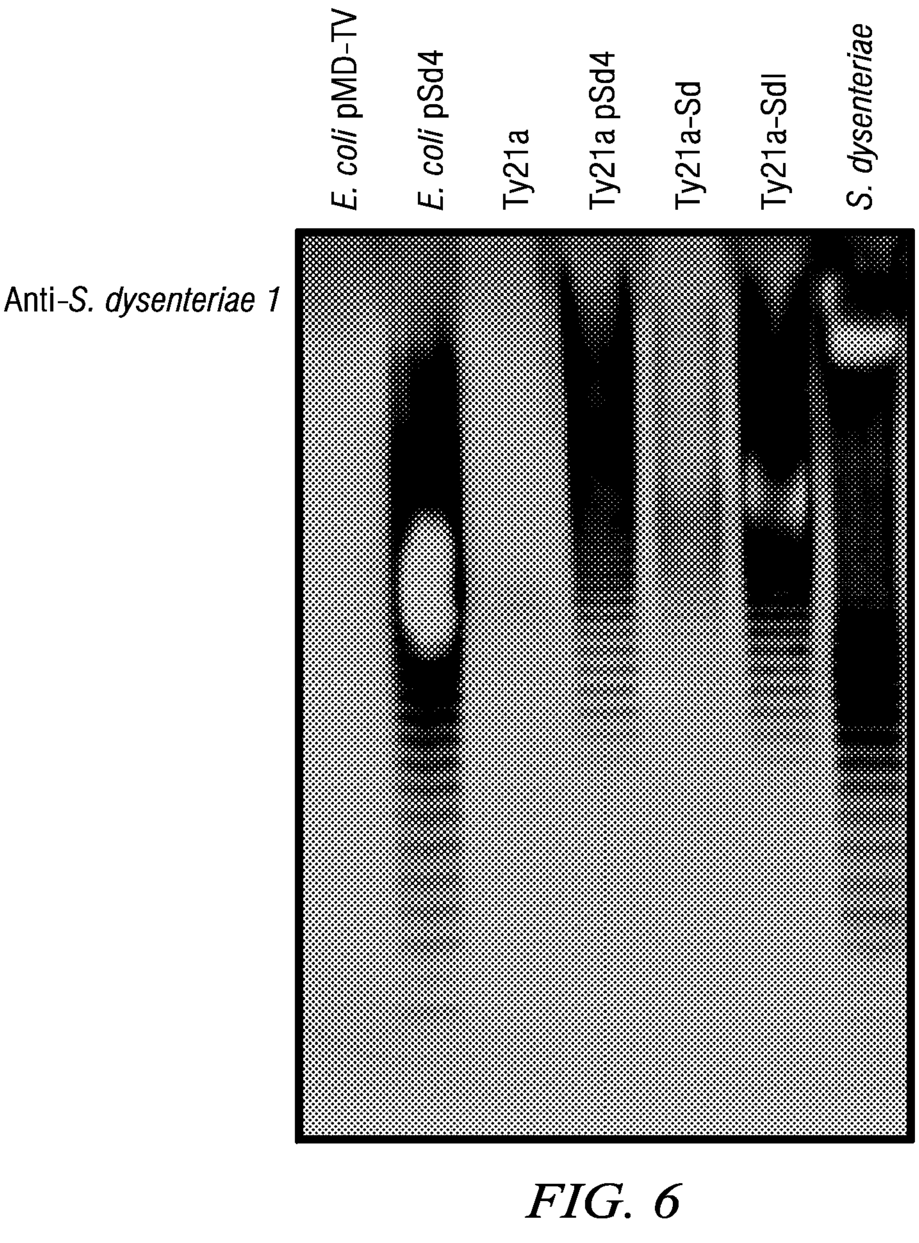
FIG. 6 shows *S. dysenteriae* O-antigen expression as determined via Western blotting.

The PCR-amplified region (which was 13,574 bp) contains part of the tviD gene, $Kan^r$ cassette flanked by FTR sites, a 200 bp lpp promoter and the first 150 bp of the *S. dysenteriae* 1 wpp gene. The PCR products were transformed into Ty21a-Sd (MD149) competent cells expressing λ red proteins from pKD46 and selected initially for $Kan^r$ resistance. Subsequently, the $Kan^r$ cassette was removed and the remaining chromosomal insert was sequenced as described (Dharmasena, et al. 2013 Intl J Med Microbiol 303:105-113) to construct Ty21a-Sdl (MD174). Expression data suggest that Ty21a-Sdl (MD174) expresses a more desirable *S. dysenteriae* LPS: S. *Typhi* Ty21a LPS ratio of approximately 1, than Ty21a-Sd (MD 149) containing the native promoter, as determined by ELISA. Indeed, Western blot with anti-*S. dysenteriae* antibody shows that replacing wpp native promoter with lpp (Ty21a-sdl, MD174) results in higher *S. dysenteriae* LPS expression than that of Ty21a-sd (MD149) and the LPS levels are comparable to plasmid expression (FIG. 6). Also O-antigen expression of both these strains were 100% stable over 75 generations of growth in vitro determined by colony immunoblotting.

Figure 7:
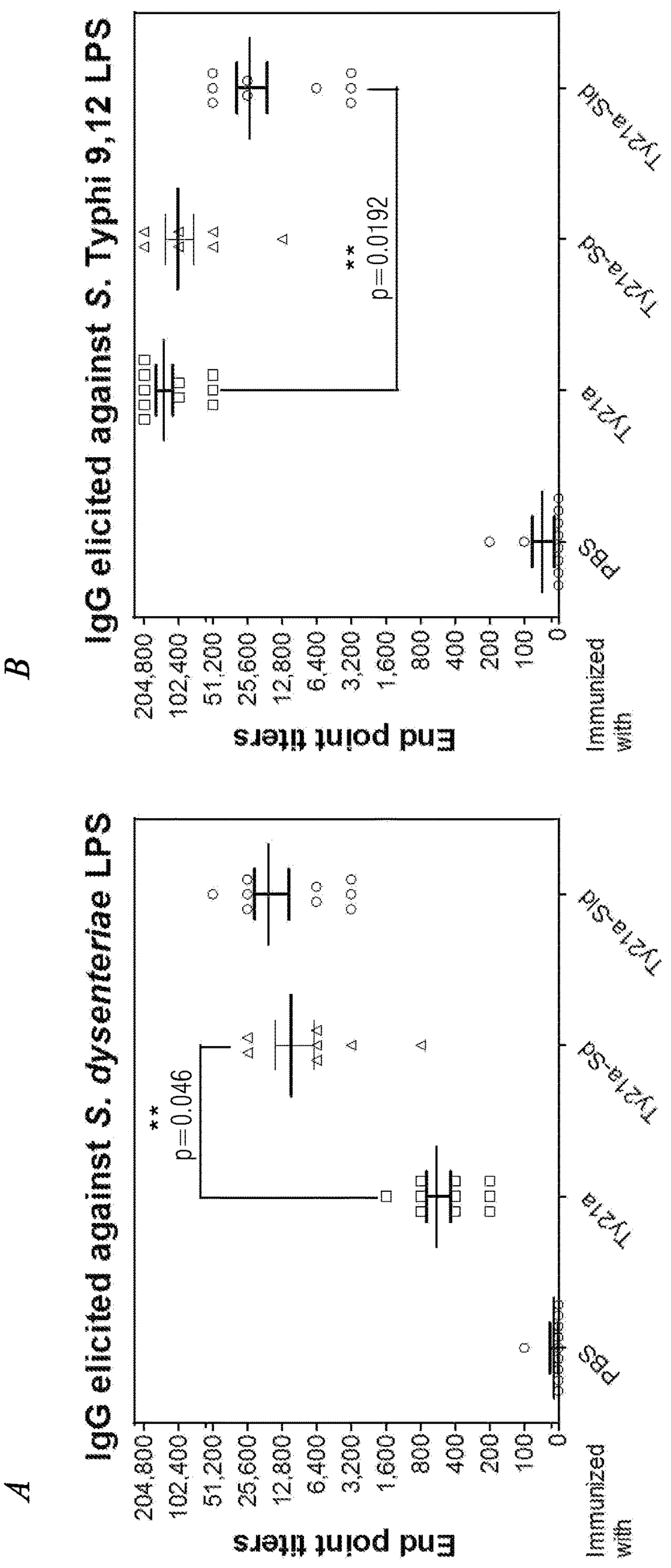
FIG. 7 shows mouse immunogenicity determined by ELISA.

Genetic Stability of Heterologous *S. dysenteriae* 1 O-Antigen Expression in Ty21a The newly recombineered vaccine strains Ty21a-Sd (MD149), SEQ ID NO:32, and Ty21-Sdl (MD174), SEQ ID NO:33, which are antibiotic-sensitive and contain chromosomally integrated Sd1 O-antigen biosynthetic genes, were grown at high dilution in Tryptic Soy broth (TSB) plus 0.01% galactose and 0.01% glucose without antibiotics for ~24 hours. This represents ~25 generations of growth. The resulting cells were plated on TSA containing 0.01% galactose and 0.01% glucose, grown overnight at 37° C., and colony immunoblots were performed to examine *S. dysenteriae* O-antigen expression with rabbit polyclonal antisera against *S. dysenteriae* 1 (Difco). All of 200 colonies tested retained *S. dysenteriae* serotype 1 O-antigen expression, demonstrating 100% stability of the chromosomally integrated genes Mouse Immunogenicity Eight week-old female AJ mice, 10 in each group, were immunized with two vaccine candidate strains (Ty21a-sd and Ty21a-sdl) or negative controls Ty21a alone and PBS. Ty21a-sd, Ty21a-sdl, and Ty21a controls were grown overnight in TSB supplemented with 0.01% galactose and 0.01% glucose, washed, and suspended in sterile PBS to a concentration of ~4-8×$10^7$ CFU per ml. Mice were inoculated intraperitoneally with a 0.5-ml dose containing ~2-4×$10^7$ CFU per mouse of either vaccine, control Ty21a cells, or 0.5 ml sterile saline, for three total doses spaced two weeks apart. Mice were tail-bled one week after the last injection. Immunization with both vaccine strains (Ty21a-sd and Ty21a-sdl) resulted in a moderate antibody titer of around 15,000 against *S. dysenteriae* compared to 400,000 for *S. sonnei*. Moreover, the parent strain Ty21a elicited serum IgG antibodies that cross reacted with *S. dysenteriae* LPS at a low level (~500) (FIG. 7). Although Ty21a-sd elicited high antibody titer against *S. Typhi* LPS (~100,000), which was essentially the same titer as that elicited by the parent strain Ty21a, the *S. Typhi* LPS antibody titer elicited by Ty21a-sdl was ~4 fold less. This is possibly due to higher *S. dysenteriae* LPS expression in Ty21a-sdl compared to Ty21a-sd. However, these results confirm the stable expression of both heterologous *S. dysenteriae* O-antigen and homologous Ty21a LPS in Ty21a-sd and Ty21a-sdl.

Mouse Protection from Virulent *S. dysenteriae* Challenge

Figure 8:
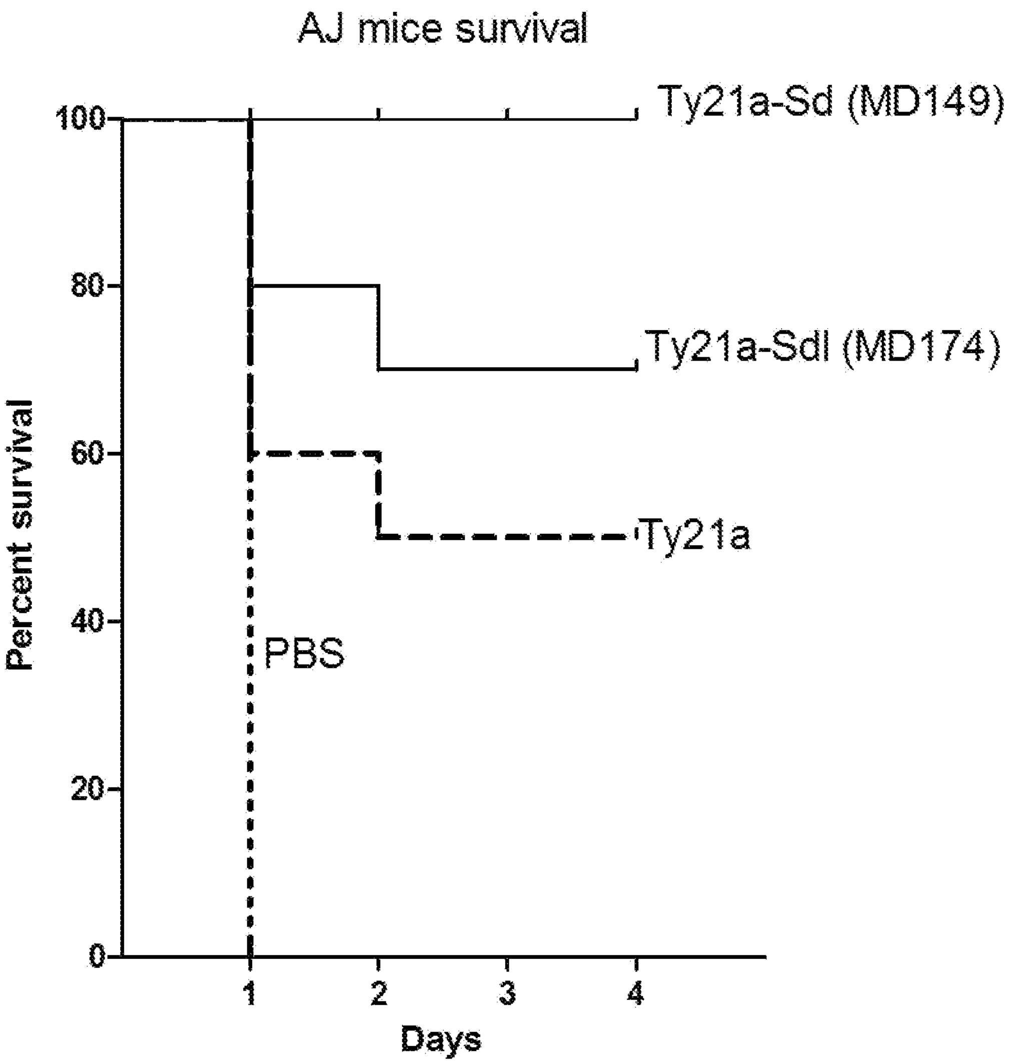
FIG. 8 shows a plot of data for immunized mice challenged IP with *S. dysenteriae* 1 at a dose of approximately $10\times LD_{50}$.

Immunized and control mice were challenged intraperitoneally, 2 weeks after final immunization, with 1.5×$10^6$ CFU/ml of freshly grown, mid-log-phase virulent *S. dysenteriae* 1 strain 1617ΔstxA in 0.5 ml (7.5×$10^5$ CFU per mouse) of 5% hog gastric mucin (Sigma) dissolved in sterile saline (i.e., approximately 10 times the 50% lethal infectious dose [LD50]). Survival was monitored for 72 h (FIG. 8). Although this challenge resulted in 100% mortality in saline-immunized mice, only 50% mortality resulted in Ty21a-alone immunized mice. This may be due to low level of *S. dysenteriae* LPS cross-reacting antibodies elicited by Ty21a, as determined by ELISA, providing some protection. Also, a low level of protection conferred by Ty21 has been observed before (Noriega, et al. 1999 *Infection and immunity* 67:782-788). The mice immunized with the recombineered vaccine strain Ty21a-Sd and Ty21a-Sdl were 100% and 70%, respectively, protected against the *S. dysenteriae* challenge.

Figure 9:
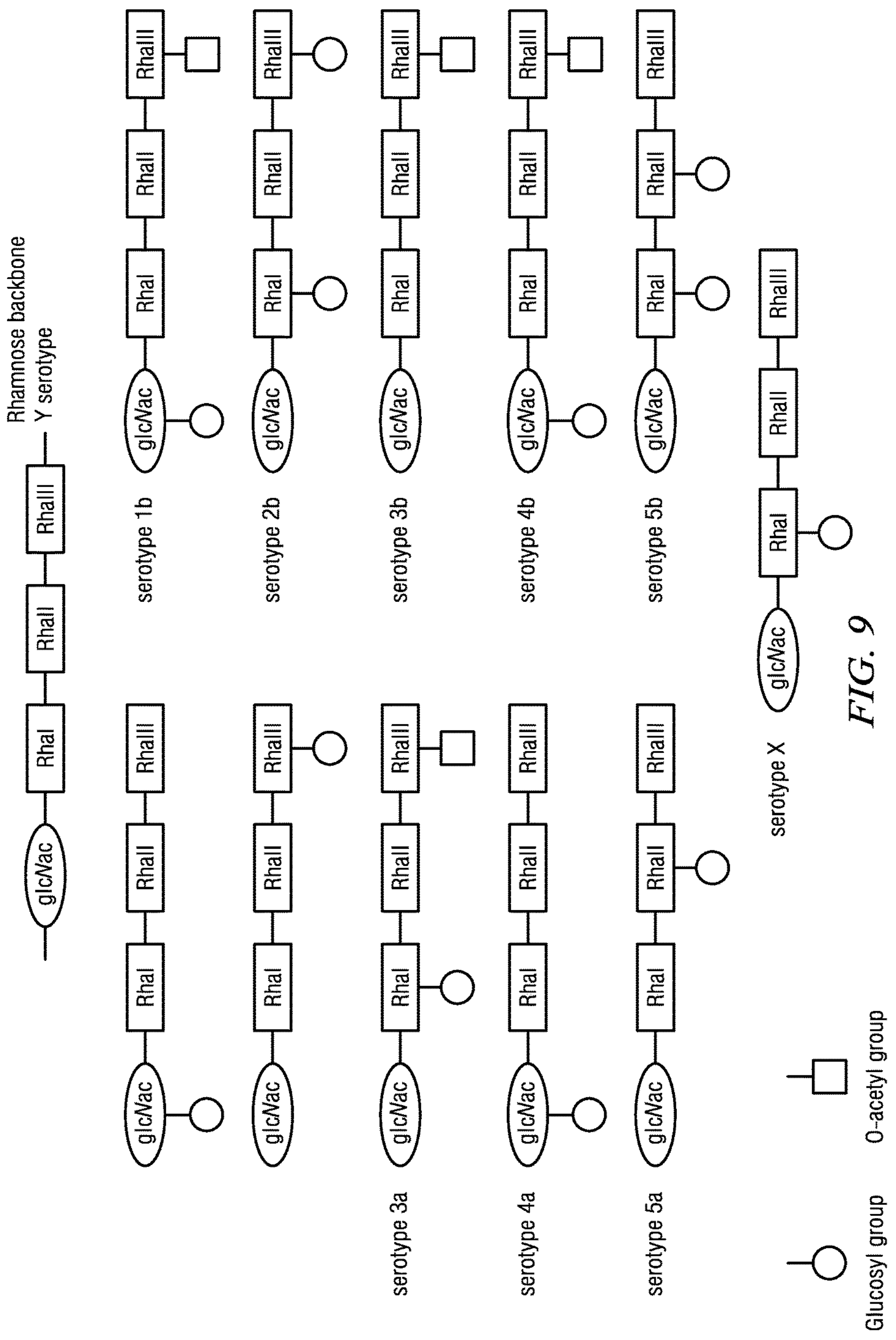
FIG. 9 shows the chemical composition of the different serotypes of *Shigella flexneri* (modified from Allison, et al. 2000 *Trends in Microbiol* 8:17-23).

Example 9. Chromosomal Integration of *Shigella flexneri* 2a and 3a O-Antigen Genes There are 14 *S. flexneri* serotypes on the basis of antigenic determinants on the O-antigen. In all of the *S. flexneri* serotypes, with the exception of serotype 6, all share a common polysaccharide backbone comprising repeating units of the tetrasaccharide N-acetylglucosamine-rhamnose-rhamnose-rhamnose (FIG. 9). The basic O-antigen backbone is called the serotype Y. The genes involved in the biosynthesis of the O-antigen backbone are located in the rfb operon (~10 kb) flanked by gnd and galF genes. Modification of the O-antigen backbone by the addition of glucosyl and/or O-acetyl groups to different sugars in the tetrasaccharide gives rise to different serotypes. The genes involved in the O-antigen modification are encoded on temperate bacteriophages (Allison, et al. 2000 *Trends in Microbiol* 8:17-23). Two genes encoded on lysogenic bacteriophage SfII were found to be essential for 2a serotype conversion. These genes are bgt, which encodes a putative bactoprenol glucosyl transferase, and gtrII, encoding the putative type II antigen determining glucosyl transferase (Mavris, et al. 1997 *Mol Microbiol* 26:939-950).

*S. flexneri* 3b O-antigen contains an O-acetyl modification, and *S. flexneri* 3a O-antigen contains a glucosyl modification in addition to the O-acetyl modification. The gene, oac, encoded on lysogenic bacteriophage Sf6, was found to be essential for the 3b serotype conversion from the Y serotype (Clark, et al. 1991 *Gene* 107:43-52). The glucosylation gene cluster (gtrA, gtrB, and gtrX) encoded by bacteriophage Sfx is involved in O-antigen modification of serotype Y to X and serotype 3b to 3a. The first gene of the glucosylation gene cluster gtrA encodes a small highly hydrophobic protein involved in the translocation of lipid-linked glucose across the cytoplasmic membrane. The gene gtrB encodes an enzyme catalyzing the transfer of the glucose residue from UDP-glucose to a lipid carrier, and gtrX encodes a bacteriophage-specific glucosyltransferase for the final step of attaching the glucosyl molecules onto the correct sugar residue of the O-antigen repeating unit (Guan, et al. 1999 *Mol Microbiol* 26:939-950).

Cloning *S. flexneri* 2a and 3a O-Antigen Genes into pMD-TV

Since cloning ~10 kb rfb operon was challenging, ~6 kb of the rfb operon was cloned into low copy plasmid pMD-TV (Dharmasena, et al. 2013 *Intl J Med Microbiol* 303:105-113), using KpnI and XhoI, followed by remaining 4 kB of the rfb operon using XhoI and BamHI. The *S. flexneri* 4 kb and 6 kb O-antigen gene regions were PCR amplified from *S. flexneri* 2a 2457 genomic DNA using prMD3-2a.rfb.F-prMD16.R and prMD18.rfb.5021.F prMD4-2a.rfb.R primer pairs (Table F, below), respectively.

TABLE F

| | |
|---|---|
| PRMD3-2A.RFB.F | GATCGGGATCCTAATGAAAATCTGACCGGATGTAACGGTTG (SEQ. ID NO: 34) |
| PRMD16.5042.R | GATCACTCGAGCGAGAAATCCTAGCG (SEQ. ID NO: 35) |
| PRMD18.RFB.F | CCCCTCGCTAGGATTTCTCGCTCGAG (SEQ. ID NO: 36) |
| PRMD4-2A.RFB.R | GATCGGGTACCTTGTTTTCTGAGCGAATATATATAAG (SEQ. ID NO: 37) |
| PRMD1-2AGTR-F | GATCGGCGGCCGCGACCCAAAATGGACTATGACAGAAAGATCTGATATTTTTCCTCGCAAAAATGAAAATATCTCTTGTCGTTC (SEQ. ID NO: 38) |
| PRMD2-2AGTR-R | GATCGGGATCCTAAATATTAAATGGAAGCC (SEQ. ID NO: 39) |
| PRMD47.3A.OAC.NOTI | ATAAGAATGCGGCCGCACTGGCTGGACCCAAAATGG (SEQ. ID NO: 40) |
| PRMD30.3A.BAMHI.R | GATCAGGATCCTCAATCCAGGGATAATTTAGGCGAAC (SEQ. ID NO: 41) |
| PRMD120.SFX.BAMHI.F | GATCAGGATCCATCGATTGAGACTTGGATGATAGACTTCATG (SEQ. ID NO: 42) |

TABLE F-continued

| | |
|---|---|
| PRMD121..SFX.BAMH.R | GATCAGGATCCTTATTTTTTTATTAAATCAAGAGTTAACCATGGAGGGAG (SEQ. ID NO: 43) |
| PRMD87.VEXA.R.32BP | TTAGAAAGAATTAGTGCCGCGGGTCAAAAAGC (SEQ. ID NO: 44) |
| PRMD133.TVID.F | CCGTTCCTCATTGATTTGATTGCTAAC (SEQ. ID NO: 45) |
| PRMD123.Y.R | CGGCAACATAAGTAATTTGCTCACG (SEQ. ID NO: 46) |
| PRMD124.F.TVID | CACGCAATATTTCAATGATGGCAAC (SEQ. ID NO: 47) |
| PRMD92.VEXB.R.17800 | GTTGCGGTAATGGTATAACGAAATAACAGATAC (SEQ. ID NO: 48) |
| PRMD118.R.2AY | TATTTATTATGTGACGAACAACAGCAGAACC (SEQ. ID NO: 49) |
| PRMD152.2A.LPP.R | AATTGACTCTGTGGCATCTTTACTTCCGTCATTTATGAATACAATTTCTACTTCATATGGCTTCAACTCTTGGAATTCACGTACCGTTTTATAGAAAACAGGTATCGCTTCTTCTTCATTGAAGACAGGAACGACAAGAGATATTTTCATATGTCCTCTCCTTTCATTATTAATACCCTCTAGAGTTC (SEQ. ID NO: 50) |

The resulting PCR 6 kb product and pMD-TV plasmid were digested with KpnI and XhoI, PCR-purified, and ligated to construct pMD-TV.2a.6, followed by digestion of 4 Kb PCR product and pMD-TV.2a.6 with XhoI and BamHI to construct pMD-TV-Y.

In order to express *S. flexneri* 2a O-antigen, the bacteriophage SfII-encoded bgt-gtrII were cloned into pMD-TV-Y upstream of the *S. flexneri* 2a rfb region. First bgt-gtrII was PCR-amplified from *S. flexneri* 2a 2457 genomic DNA with primers that contained NotI and BamHI (prMD1-2agtr-F and prMD2-2agtr-R, FIG. 9). The resulting PCR product and pMD-TV-Y were digested with NotI and BamHI, PCR-purified, and ligated to construct pMD-TV-2a.

In order to express *S. flexneri* 3a O-antigen, the *S. flexneri* 2a rfb region, bacteriophage Sf6 encoded oac and bacteriophage SfX-encoded gtrX, gtrA and gtrB were cloned, with their cognate promoters, tandemly into the pMD-TV vector. The SF6-encoded oac was PCR-amplified from *S. flexneri* 3a J99 genomic DNA with primers that contained NotI and BamHI sites (prMD47.3a.OAC.NotI and prMD30.3a.BamHI.R, FIG. 9). The resulting PCR product and pMD-TV-Y were digested with NotI and BamHI, PCR-purified, and ligated to construct pMD-TV-3b. Similarly, gtrX, gtrA, and gtrB gene cluster was PCR-amplified from *S. flexneri* 3a J99 genomic DNA with primers that contained BamHI site (prMD120.sfx.bamHI.F and prMD121.sfx.bamH.R, FIG. 9) and cloned into the BamHI site of pMD-TV-3b to construct pMD-TV-3a. All of the constructs were confirmed by PCR and sequencing.

Expression of *S. flexneri* 2a and 3a O-Antigen from the Plasmid

Figure 10:
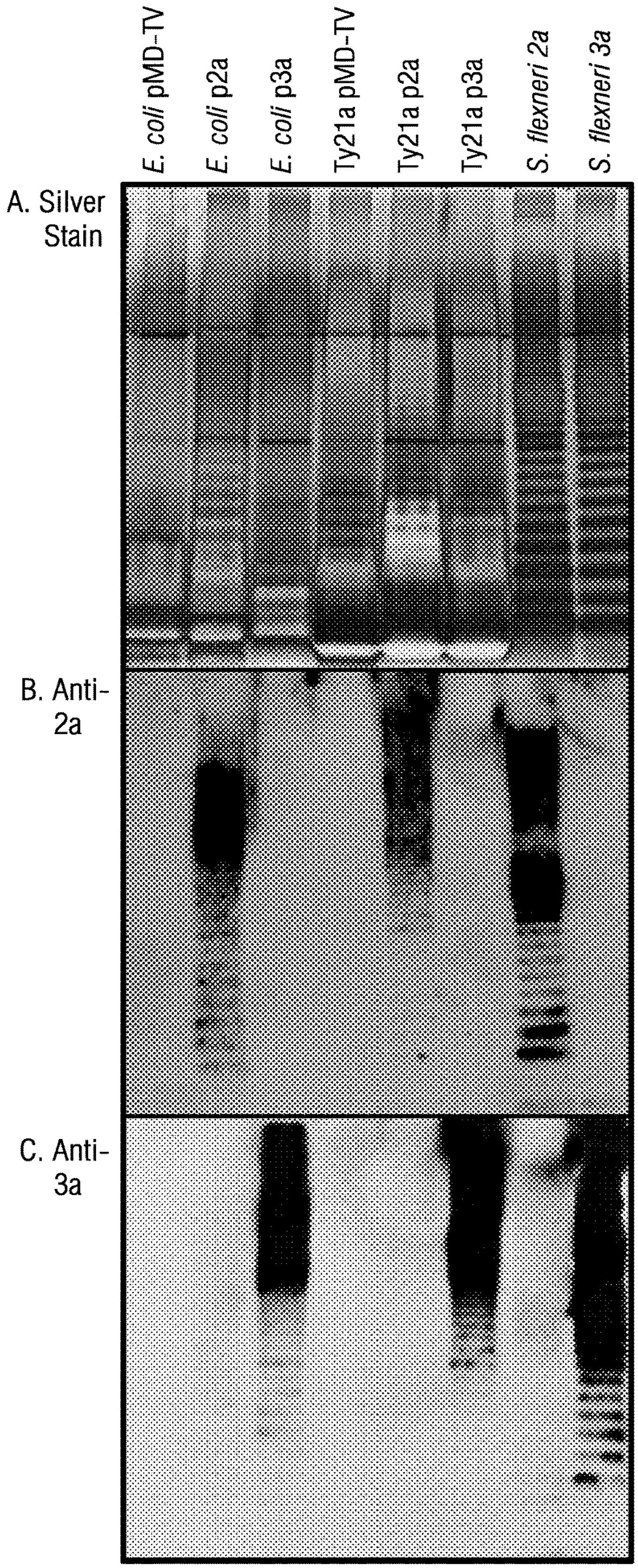
FIG. 10 shows Silver stain (FIG. 10A) and Western blot (FIGS. 10B and 10C) with anti-2a (FIG. 10B) and anti-3a (FIG. 10C) antibodies.

Expression of *S. flexneri* 2a and 3a O-antigen from pMD-TV-2a and pMD-TV-3a, respectively, in *E. coli* and Ty21a, was confirmed by slide agglutination and by Western blotting. pMD-TV-2a in *E. coli* or Ty21a reacts with *S. flexneri* type II specific anti-sera (FIG. 10) and also agglutinated with *S. flexneri* 3,4 epitope specific anti-sera. Thus, pMD-TV-2a contains all of the genes required for stable *S. flexneri* 2a O-antigen expression (Dharmasena, et al. 2012 *Am Soc Microbiol* mtg, San Francisco, Calif.).

pMD-TV-3a in *E. coli* or Ty21a reacts with *S. flexneri* type III specific anti-sera (FIG. 10). pMD-TV-3a strains also agglutinated with *S. flexneri* 6 and 7, 8 epitope specific anti-sera. Thus, pMD-TV-3a contains all of the genes required for stable *S. flexneri* 3a O-antigen expression.

Integrating *S. flexneri* O-Antigen Genes into Ty21a Chromosome

Figure 11:
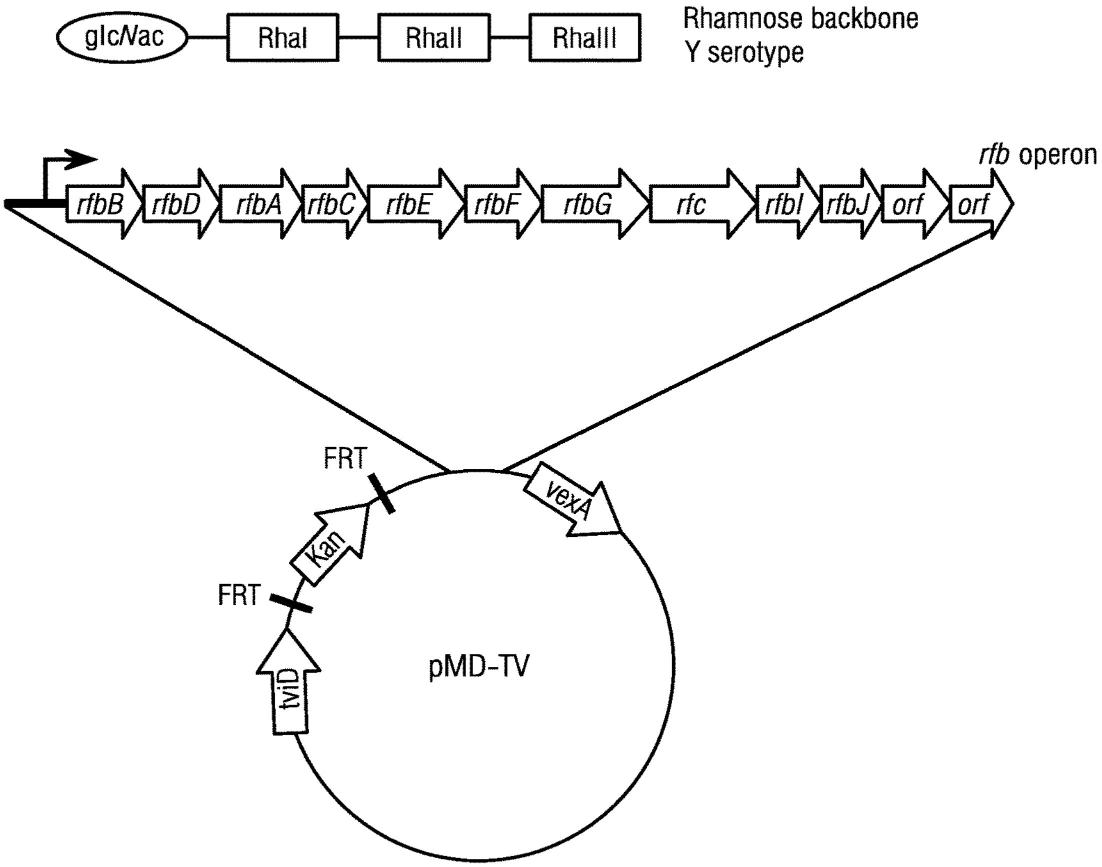
FIG. 11 is a schematic representation of *S. flexneri* basic O-antigen backbone, serotype Y, and the genes involved in the biosynthesis of this O-antigen backbone are located in the rfb operon (~10 kb) were cloned into pMD-TV plasmid.

The *S. flexneri* O-antigen Y serotype backbone genes that were cloned into pMD-TV (pMD-TV-Y) were used as template for PCR with tviD forward (prMD133.tviD.F) primer and vexA reverse (prMD87.vexA.R.32 bp) primer. The PCR-amplified region that contains part of tviD gene, Kan cassette flanked by FTR sites, *S. flexneri* rfb genes and vexA gene was 13,653 bp. These PCR products were transformed into Ty21a competent cells expressing 2 red proteins from pKD46 and selected for Kan resistance as described in (Dharmasena, et al. 2013). PCR with primers upstream and downstream of the site of integration prMD92 and prMD124 resulted in a ~14.5 Kb band. After removing the Kanr cassette as described in (Dharmasena, et al. 2013), antibiotic-sensitive chromosomal integrants were further analyzed by PCR for deletion of the Kan cassette and sequenced the PCR product (strain MD 114/Ty21a-Y~13 Kb band) obtained from primers prMD92 and prMD124. The sequence of this PCR was compared to *S. flexneri* 2a 2457 (GenBank accession no. AE014073.1, complete genome 4,599,354 bp, reference: Wei, et al. 2003 *Infect Immun* 71(5):2775-2786), and only a single A insertion was detected in the intergenic region upstream of gene rfbC (FIG. 11), which did not affect the O-antigen expression determined by Western blot with anti-*S. flexneri* 1-6 antibody.

Figure 12:
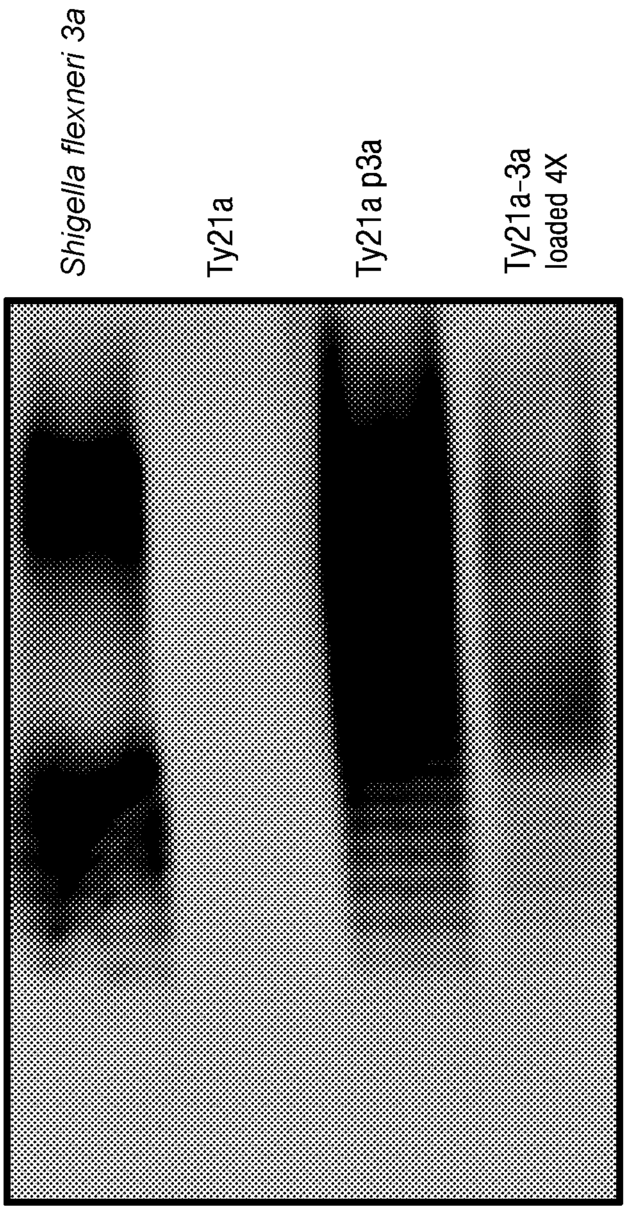
FIG. 12 shows a Western blot with anti-*S. flexneri* 3a antibody.

In order to integrate *S. flexneri* 2a modifying enzymes bgt and gtrII upstream of rfb operon in Ty21a-Y, pMD-TV-2a was used as template for PCR with tviD forward primer (prMD133.tviD.F) and rfb operon reverse primer (prMD118.R.2aY). The PCR-amplified region that contains part of tviD gene, Kan cassette flanked by FTR sites, *S. flexneri* 2a modifying enzymes bgt and gtrII, and first ~500 bp of the rfb operon was 5,132 bp. These PCR products were transformed into Ty21a-Y competent cells expressing 2 red proteins and selected for Kan resistance as before. PCR with primers upstream and downstream of the site of integration prMD92 and prMD124 resulted in a ~17 Kb band. After removing the Kan$^r$ cassette, antibiotic-sensitive chromosomal integrants were further analyzed by PCR for deletion of the Kan cassette and sequenced the PCR product (strain MD 194/Ty21a-2a ~15.5 Kb band) obtained from primers prMD92 and prMD124. The sequence of this PCR was compared to SFII coded bgt-gtrII region and rfb region of *S. flexneri* 2a 2457, and no additional mutations were found. Also, *S. flexneri* 2a expression was determined by Western blot with *S. flexneri* type II specific anti-sera showed only weak expression compared to the plasmid expression (FIG. 12). This may be due to multiple copies of the plasmid (~5 per cell) expressing more *S. flexneri* 2a O-antigen compared to only one copy of *S. flexneri* 2a O-antigen biosynthetic genes integrated into the Ty21a chromosome in Ty21-2a strain (FIG. 12).

Similarly, *S. flexneri* 3a modifying enzymes gtrX, gtrA, and gtrB gene cluster and oac were integrated upstream of the rfb operon in the Ty21a-Y strain as described before using pMD-TV-3a as template for PCR. The PCR product that was transformed into Ty21a-Y competent cells expressing λ red was 6448 bp. After integration, PCR with primers upstream and downstream of the site of integration prMD92 and prMD124 resulted in a ~18.5 Kb band and after removing the Kan$^r$cassette (strain MD 194/Ty21a-3a) resulted in a ~17 Kb band. The sequence of this PCR was compared to bacteriophage Sf6-encoded oac and bacteriophage SfX-encoded gtrX, gtrA, and gtrB and *S. flexneri* 2a 2457, and no additional mutations were found. Also, *S. flexneri* 3a expression was determined by Western blot with *S. flexneri* type III specific anti-sera showed only weak expression compared to the plasmid expression as *S. flexneri* 2a (FIG. 12).

Replacing Bgt Native Promoter with lpp

Figure 13:
FIG. 13 shows a Western blot with anti-*S. flexneri* 2a antibody.

Attempts were made to increase the *S. flexneri* 2a LPS expression by replacing the native bgt promoter with the lpp promoter, which is a highly transcribed constitutively active promoter. Ty21a-sdl (*S. dysenteriae* O-antigen biosynthesis genes expressed from lpp promoter) was used as template for PCR with tviD forward primer and lpp promoter reverse primer with 150 bp bgt homology extension (Table F). The PCR-amplified region contains part of tviD gene, Kan cassette flanked by FTR sites, 200 bp lpp promoter, and first 150 bp bgt gene. The PCR products were transformed into Ty21a-2a (MD194) competent cells expressing λ red proteins and selected for Kan resistance, removed the Kan cassette, and sequenced as described before to construct Ty21a-2al (MD212). Western blot with *S. flexneri* type II specific anti-sera shows that Ty21a-2al (MD212) expresses higher *S. flexneri* 2a LPS than that of Ty21a-2a (MD194), but still less than plasmid expression (Ty21a pMD-TV-2a) (FIG. 13).

Additional efforts are being made to carry out animal experiments employing new constructs.

REFERENCES

1. Kotloff, K. L., Winickoff, J. P., Ivanoff, B., Clemens, J. D., Swerdlow, D. L., Sansonetti, P. J., Adak, G. K., and Levine, M. M. (1999) *Bulletin of the World Health Organization* 77, 651-666
2. Kweon, M. N. (2008) *Current opinion in infectious diseases* 21, 313-318
3. Mead, P. S., Slutsker, L., Dietz, V., McCaig, L. F., Bresee, J. S., Shapiro, C., Griffin, P. M., and Tauxe, R. V. (1999) *Emerging infectious diseases* 5, 607-625
4. Putthasri, W., Lertiendumrong, J., Chompook, P., Tangcharoensathien, V., and Coker, R. (2009) *Emerging infectious diseases* 15, 423-432
5. WHO. (2005). in *Guidelines for the control of shigellosis, including epidemics due to Shigella dysenteriae type* 1, World Health Organization, Geneva, Switzerland
6. Kaminski, R. W., and Oaks, E. V. (2009) *Expert review of vaccines* 8, 1693-1704
7. Ferreccio, C., Prado, V., Ojeda, A., Cayyazo, M., Abrego, P., Guers, L., and Levine, M. M. (1991) *American journal of epidemiology* 134, 614-627
8. DuPont, H. L., Hornick, R. B., Snyder, M. J., Libonati, J. P., Formal, S. B., and Gangarosa, E. J. (1972) *The Journal of infectious diseases* 125, 5-11
9. DuPont, H. L., Hornick, R. B., Snyder, M. J., Libonati, J. P., Formal, S. B., and Gangarosa, E. J. (1972) *The Journal of infectious diseases* 125, 12-16
10. Noriega, F. R., Liao, F. M., Maneval, D. R., Ren, S., Formal, S. B., and Levine, M. M. (1999) *Infection and immunity* 67, 782-788
11. Xu de, Q., Cisar, J. O., Osorio, M., Wai, T. T., and Kopecko, D. J. (2007) *Vaccine* 25, 6167-6175
12. Xu, D. Q., Cisar, J. O., Ambulos Jr, N., Jr., Burr, D. H., and Kopecko, D. J. (2002) *Infection and immunity* 70, 4414-4423

13. Osorio, M., Wu, Y., Singh, S., Merkel, T. J., Bhattacharyya, S., Blake, M. S., and Kopecko, D. J. (2009) *Infection and immunity* 77, 1475-1482
14. Kopecko, D. J., Sieber, H., Ures, J. A., Furer, A., Schlup, J., Knof, U., Collioud, A., Xu, D., Colburn, K., and Dietrich, G. (2009) *International journal of medical microbiology: IJMM* 299, 233-246
15. D'Amelio, R., Tagliabue, A., Nencioni, L., Di Addario, A., Villa, L., Manganaro, M., Boraschi, D., Le Moli, S., Nisini, R., and Matricardi, P. M. (1988) *Infection and immunity* 56, 2731-2735
16. Seid, R. C., Jr., Kopecko, D. J., Sadoff, J. C., Schneider, H., Baron, L. S., and Formal, S. B. (1984) *The Journal of biological chemistry* 259, 9028-9034
17. Formal, S. B., Baron, L. S., Kopecko, D. J., Washington, O., Powell, C., and Life, C. A. (1981) *Infection and immunity* 34, 746-750
18. Black, R. E., Levine, M. M., Clements, M. L., Losonsky, G., Herrington, D., Berman, S., and Formal, S. B. (1987) *The Journal of infectious diseases* 155, 1260-1265
19. Herrington, D. A., Van de Verg, L., Formal, S. B., Hale, T. L., Tall, B. D., Cryz, S. J., Tramont, E. C., and Levine, M. M. (1990) *Vaccine* 8, 353-357
20. Van de Verg, L., Herrington, D. A., Murphy, J. R., Wasserman, S. S., Formal, S. B., and Levine, M. M. (1990) *Infection and immunity* 58, 2002-2004
21. Datsenko, K. A., and Wanner, B. L. (2000) *Proceedings of the National Academy of Sciences of the United States of America* 97, 6640-6645
22. Cherepanov, P. P., and Wackernagel, W. (1995) *Gene* 158, 9-14
23. Murphy, K. C. (1998) *Journal of bacteriology* 180, 2063-2071
24. Sawitzke, J. A., Thomason, L. C., Costantino, N., Bubunenko, M., Datta, S., and Court, D. L. (2007) *Methods in enzymology* 421, 171-199
25. Uzzau, S., Figueroa-Bossi, N., Rubino, S., and Bossi, L. (2001) *Proceedings of the National Academy of Sciences of the United States of America* 98, 15264-15269
26. Yu, B., Yang, M., Wong, H. Y., Watt, R. M., Song, E., Zheng, B. J., Yuen, K. Y., and Huang, J. D. (2011) *Applied microbiology and biotechnology* 91, 177-188
27. Ohtake, S., Martin, R., Saxena, A., Pham, B., Chiueh, G., Osorio, M., Kopecko, D., Xu, D., Lechuga-Ballesteros, D., and Truong-Le, V. (2011) *Vaccine* 29, 2761-2771
28. Germanier, R., and Fuer, E. (1975) *The Journal of infectious diseases* 131, 553-558
29. Kopecko, D. J., Washington, O., and Formal, S. B. (1980) *Infection and immunity* 29, 207-214
30. Churchward, G., Belin, D., and Nagamine, Y. (1984) *Gene* 31, 165-171

The invention claimed is:

1. A *Salmonella Typhi* Ty21a comprising a *Shigella sonnei* form 1 O-antigen biosynthetic gene region inserted into the *Salmonella Typhi* Ty21a chromosome, wherein:

a) heterologous *Shigella sonnei* form 1 O-antigen is stably expressed together with or without homologous *Salmonella Typhi* O-antigen;

b) immune protection is elicited against virulent *Shigella sonnei* challenge; and c) immune protection is elicited against virulent *Salmonella Typhi* challenge when heterologous *Shigella sonnei* form 1 O-antigen is stably expressed together with homologous *Salmonella Typhi* O-antigen; and d) the region comprises a DNA sequence, wherein the DNA sequence comprises:

1) the DNA sequence as set out in SEQ ID NO:2, or 2) a DNA sequence that shares at least about 90% sequence identity with the DNA sequence set out in SEQ ID NO:2.

2. The *Salmonella Typhi* Ty21a of claim 1, further comprising an O-antigen biosynthetic gene region from a bacterial strain selected from the group consisting of: *Shigella* species, *Escherichia coli* serotypes, *Salmonella enterica* serovars, *Vibrio cholerae* serotypes, *Enterobacter* species, *Yersinia* species, *Plesiomonas* species, and *Pseudomonas* species.

3. A *Salmonella Typhi* Ty21a comprising a *Shigella dysenteriae* 1 O-antigen biosynthetic gene region inserted into the *Salmonella Typhi* Ty21a chromosome, wherein:

a) heterologous *Shigella dysenteriae* serotype 1 O-antigen is stably expressed together with or without homologous *Salmonella Typhi* O-antigen;

b) immune protection is elicited against virulent *Shigella dysenteriae* challenge; and c) immune protection is elicited against virulent *Salmonella Typhi* challenge when heterologous *Shigella dysenteriae* serotype 1 O-antigen is stably expressed together with homologous *Salmonella Typhi* O-antigen; and d) the region comprises a DNA sequence, wherein the DNA sequence comprises:

1) the DNA sequence as set out in SEQ ID NO:33, or 2) a DNA sequence that shares at least about 90% sequence identity with the DNA sequence set out in SEQ ID NO:33.

4. The *Salmonella Typhi* Ty21a of claim 3, further comprising an O-antigen biosynthetic gene region from a bacterial strain selected from the group consisting of: *Shigella* species, *Escherichia coli* serotypes, *Salmonella enterica* serovars, *Vibrio cholerae* serotypes, *Enterobacter* species, *Yersinia* species, *Plesiomonas* species, and *Pseudomonas* species.

5. A plasmid construct having i) a DNA sequence as set out in SEQ ID NO: 1 or ii) a DNA sequence that shares at least about 90% sequence identity with the DNA sequence set out in SEQ ID NO:1.

6. The plasmid construct of claim 5, further comprising a *Shigella sonnei* O-antigen biosynthetic gene region or a *Shigella dysenteriae* 1 O-antigen biosynthetic gene region.

7. A method of recombineering a large antigenic gene region into a bacterial chromosome, comprising:

i) cloning the region into a vector containing:

ia) a genetically selectable marker flanked 5' and 3' by an FRT site, respectively;

ib) a multiple cloning site downstream of the 3' FRT site; and ic) two sites of chromosome homology, one of the two located upstream of the 5' FRT site, and one of the two located downstream of the multiple cloning site;

ii) integrating the region into the bacterial chromosome using X, red recombination;

iii) selecting for the genetically selectable marker; and iv) removing the selectable marker, thus recombineering the large antigenic gene region into the chromosome.

8. The method of claim 7, wherein the large antigenic gene region is about 5 to about 20 kb long.

9. The method of claim 7, wherein the vector is selected from the group consisting of a plasmid, phage, phasmid, and cosmid construct.

10. The method of claim 9, wherein the plasmid construct has i) a DNA sequence as set out in SEQ ID NO: 1 or ii) a DNA sequence that shares at least about 90% sequence identity with the DNA sequence set out in SEQ ID NO:1.

11. The method of claim 7, wherein the bacterial chromosome is from *Salmonella Typhi* Ty21a.

12. The method of claim 7, wherein the genetically selectable marker is an antibiotic resistance marker.

13. The method of claim 12, wherein the antibiotic resistance marker is kanamycin.

14. The method of claim 7, wherein the large antigenic gene region is selected from the group consisting of a *Shigella sonnei* O-antigen biosynthetic gene region, a *Shigella dysenteriae* 1 O-antigen biosynthetic gene region, a *Shigella flexneri* 2a 0-antigen biosynthetic gene region, and a *Shigella flexneri* 3a O-antigen biosynthetic gene region.

15. The method of claim 7, wherein the large antigenic gene region is engineered between the two sites of chromosome homology, each site comprising between about 500 to about 1000 bp regions of bacterial chromosome homology before step ii.

16. The method of claim 13, wherein the kanamycin resistance gene is removed via recombination induced following transformation of chromosomal integrants of step ii with pCP20.

17. A vaccine comprising a pharmaceutically acceptable solid carrier and *Salmonella Typhi* Ty21a comprising a

*Shigella flexneri* 2a O-antigen biosynthetic gene region inserted into the *Salmonella Typhi* Ty21a chromosome, wherein:

a) heterologous *Shigella flexneri* 2a O-antigen is stably expressed together with or without homologous *Salmonella Typhi* O-antigen;

b) immune protection is elicited against virulent *Shigella flexneri* 2a challenge; and c) immune protection is elicited against virulent *Salmonella Typhi* challenge when heterologous *Shigella flexneri* 2a O-antigen is stably expressed together with homologous *Salmonella Typhi* O-antigen.

18. A vaccine comprising a pharmaceutically acceptable solid carrier and *Salmonella Typhi* Ty21a comprising a *Shigella flexneri* 3a O-antigen biosynthetic gene region inserted into the *Salmonella Typhi* Ty21a chromosome, wherein:

a) heterologous *Shigella flexneri* 3a O-antigen is stably expressed together with or without homologous *Salmonella Typhi* O-antigen;

b) immune protection is elicited against virulent *Shigella flexneri* 3a challenge; and c) immune protection is elicited against virulent *Salmonella Typhi* challenge when heterologous *Shigella flexneri* 3a O-antigen is stably expressed together with homologous *Salmonella Typhi* O-antigen.

19. A vaccine comprising the *Salmonella Typhi* Ty21a of claim 1 in combination with a physiologically acceptable carrier.

20. A method of treating at least one bacterial infection comprising administering a prophylactically or therapeutically effective amount of the *Salmonella Typhi* Ty21a of claim 1 to a subject, thus treating the at least one bacterial infection.

21. The *Salmonella Typhi* Ty21a of claim 1, wherein the *Shigella sonnei* form 1 O-antigen biosynthetic gene region is partially or wholly chemically synthesized.

22. The plasmid construct of claim 5, wherein the DNA sequence is partially or wholly chemically synthesized.

* * * * *

UNITED STATES PATENT AND TRADEMARK OFFICE

CERTIFICATE OF CORRECTION

PATENT NO. : 9,750,793 B2
APPLICATION NO. : 14/428870
DATED : September 5, 2017
INVENTOR(S) : Madushini Nirosha Dharmasena et al.

It is certified that error appears in the above-identified patent and that said Letters Patent is hereby corrected as shown below:

In the Claims

In Column 145, Line 2 Claim 7, “X,” should be --λ--.

Signed and Sealed this
Twenty-fifth Day of December, 2018

Andrei Iancu
*Director of the United States Patent and Trademark Office*

SEQUENCE LISTING

```
<160> NUMBER OF SEQ ID NOS: 50

<210> SEQ ID NO 1
<211> LENGTH: 6155
<212> TYPE: DNA
<213> ORGANISM: Shigella sonnei
<220> FEATURE:
<221> NAME/KEY: misc_feature
<223> OTHER INFORMATION: Plasmid pMD-TV (JX436480)

<400> SEQUENCE: 1

gtcgacgggc ggccgcaagc ttggatccac cggtctcgag gggcgcgccg gtaccgaatt     60

ctaattaatg ggcatcattt ttcagctatt tcatttataa aataagttat gaaaaaaatc    120

atcatattac taacgacatt tttcctgctt tcgggatgca ctattcccag ggcggtattt    180

aaatccagcc ttattaatca ggacgatcct cgttataatc tggtcgaagt cacgccgaca    240

ttaaaactaa gcgctcccga tactgtgccg aaaactattg tcgatccggt ttttgccgca    300

aataactggc actggacatc tttggctaaa ggcgatgtgc tgcatatcac tattttatcc    360

tcgggcgggg ctggatattt atccaataac gcgagcggcg accgtgcgga ttttgaaaat    420

attcttgtga ctgacagtaa taccgttcag gtgccttatg ccgggacaat cccggtttct    480

ggattggatg tgacgcaact ggctgatgag atcaaaaagc gactttcgcg cgttgtcctg    540

aatcctcagg tgattgtgac acttaccgcc cgcaccggag ccatggtgac ggtcgagggc    600

agcgggaaaa cgggtcgata ccctctcgaa cagagtatga atcgtctgag tcatcttttg    660

gcaacggcag tggcagtaga aaataccagc acagatatga tggaagttca cgtgacgcgc    720

cagcagcatt atttcactgc gcgactgtca gatatttatc agtatcccgg attggatatt    780

gccttacagc cggatgaccg tatcactctg cgtcaagtga ccgagtatgt taatgtgctc    840

ggcgcagcag gtgttcaggg gaaacatgct ctggttcagc gtcattccag cgtcgtggat    900

gctttggcgc tcgcgaaagg attaaatgac aatcttgccg atccgcaagc gatttttctg    960

tacaagcata acgaagcgga acaggcgaaa cagcagatgc gtaagctgaa tatctatcat   1020
```

-continued

```
gtcgatatga gccaacctaa ctcggtgttt ttagcgcagg ccatacgagt ggacaacggc   1080
gatgttatct atatctcgaa cgcctctttg actgatttcg ctaaggtgaa agccgcattc   1140
gatagctttt tgacccgcgg cactaattct ttctaaccga cagtaagacg ggtaagcctg   1200
ttgatgatac cgctgcctta ctgggtgcat tagccagtct gaatgacctg tcacgggata   1260
atccgaagtg gtcagactgg aaaatcagag ggcaggaact gctgaacagc aaaaagtcag   1320
atagcaccac atagcagacc cgccataaaa cgccctgaga agcccgtgac gggcttttct   1380
tgtattatgg gtagtttcct tgcatgaatc cataaaaggc gcctgtagtg ccatttaccc   1440
ccattcactg ccagagccgt gagcgcagcg aactgaatgt cacgaaaaag acagcgactc   1500
aggtgcctga tggtcggaga caaaaggaat attcagcgat ttgcccgagc ttgcgagggt   1560
gctacttaag cctttagggt tttaaggtct gttttgtaga ggagcaaaca gcgtttgcga   1620
catccttttg taatactgcg gaactgacta aagtagtgag ttatacacag ggctgggatc   1680
tattcttttt atcttttttt attctttctt tattctataa attataacca cttgaatata   1740
aacaaaaaaa acacacaaag gtctagcgga atttacagag ggtctagcag aatttacaag   1800
ttttccagca aaggtctagc agaatttaca gatacccaca actcaaagga aaaggactag   1860
taattatcat tgactagccc atctcaattg gtatagtgat taaaatcacc tagaccaatt   1920
gagatgtatg tctgaattag ttgttttcaa agcaaatgaa ctagcgatta gtcgctatga   1980
cttaacggag catgaaacca agctaatttt atgctgtgtg gcactactca accccacgat   2040
tgaaaaccct acaaggaaag aacggacggt atcgttcact tataaccaat acgctcagat   2100
gatgaacatc agtagggaaa atgcttatgg tgtattagct aaagcaacca gagagctgat   2160
gacgagaact gtggaaatca ggaatccttt ggttaaaggc tttgagattt tccagtggac   2220
aaactatgcc aagttctcaa gcgaaaaatt agaattagtt tttagtgaag agatattgcc   2280
ttatcttttc cagttaaaaa aattcataaa atataatctg gaacatgtta agtcttttga   2340
aaacaaatac tctatgagga tttatgagtg gttattaaaa gaactaacac aaaagaaaac   2400
tcacaaggca aatatagaga ttagccttga tgaatttaag ttcatgttaa tgcttgaaaa   2460
taactaccat gagtttaaaa ggcttaacca atgggttttg aaaccaataa gtaaagattt   2520
aaacacttac agcaatatga aattggtggt tgataagcga ggccgcccga ctgatacgtt   2580
gattttccaa gttgaactag atagacaaat ggatctcgta accgaacttg agaacaacca   2640
gataaaaatg aatggtgaca aaataccaac aaccattaca tcagattcct acctacataa   2700
cggactaaga aaaacactac acgatgcttt aactgcaaaa attcagctca ccagttttga   2760
ggcaaaattt ttgagtgaca tgcaaagtaa gtatgatctc aatggttcgt tctcatggct   2820
cacgcaaaaa caacgaacca cactagagaa catactggct aaatacggaa ggatctgagg   2880
ttcttatggc tcttgtatct atcagtgaag catcaagact aacaaacaaa agtagaacaa   2940
ctgttcaccg ttacatatca aagggaaaac tgtccatatg cacagatgaa aacggtgtaa   3000
aaaagataga tacatcagag cttttacgag tttttggtgc attcaaagct gttcaccatg   3060
aacagatcga caatgtaaca gatgaacagc atgtaacacc taatagaaca ggtgaaacca   3120
gtaaaacaaa gcaactagaa catgaaattg aacacctgag acaacttgtt acagctcaac   3180
agtcacacat agacagcctg aaacaggcga tgctgcttat cgaatcaaag ctgccgacaa   3240
cacgggagcc agtgacgcct cccgtgggga aaaaatcatg gcaattctgg aagaaatagc   3300
gctttcagcc ggcaaacctg aagccggatc tgcgattctg ataacaaact agcaacacca   3360
```

-continued gaacagcccg tttgcgggca gcaaaacccg tgggaattaa ttcccctgct cgcgcaggct 3420
gggtgccaag ctctcgggta acatcaaggc ccgatccttg gagcccttgc cctcccgcac 3480
gatgatcgtg ccgtgatcga aatccagatc cttgacccgc agttgcaaac cctcactgat 3540
ccgcatgccc gttccataca gaagctgggc gaacaaacga tgctcgcctt ccagaaaacc 3600
gaggatgcga accacttcat ccggggtcag caccaccggc aagcgccgcg acggccgagg 3660
tcttccgatc tcctgaagcc agggcagatc cgtgcacagc accttgccgt agaagaacag 3720
caaggccgcc aatgcctgac gatgcgtgga gaccgaaacc ttgcgctcgt tcgccagcca 3780
ggacagaaat gcctcgactt cgctgctgcc caaggttgcc gggtgacgca caccgtggaa 3840
acggatgaag gcacgaaccc agtggacata agcctgttcg gttcgtaagc tgtaatgcaa 3900
gtagcgtgct agcccgttcc tcattgattt gattgctaac gtcatgagca ttactctatc 3960
attccagaat gcctcaatga acaagttgtt tgagaaagag tgtcgcaatg ttgcaaccag 4020
agcccttaaa tatgtacgcc agaagaaaac tgaagggcgt ctggatgaag cattgtctgt 4080
attgattagc ctgaaacgaa ttgagcctga tgtttctcgt ctgatgcgtg aatataagca 4140
aattatcaga ttatttaatg agtcacggaa ggatggcggt agcactatca cgtcttatga 4200
acatctagac tatgcgaaaa aattactcgt ttttgatagc gaaaatgcct atgccttgaa 4260
atatgccgca ttaaatgcaa tgcatttacg cgactacacg caggctttgc agtattggca 4320
gcgactggag aaagtgaatg gaccaacgga gccggtgaca aggcagatct cgacctgcat 4380
aaccgcatta caaaaaaata catcagggaa gtcgtaaccc ggggtgtagg ctggagctgc 4440
ttcgaagttc ctatactttc tagagaatag gaacttcgga ataggaactt caagatcccc 4500
tcacgctgcc gcaagcactc agggcgcaag ggctgctaaa ggaagcggaa cacgtagaaa 4560
gccagtccgc agaaacggtg ctgaccccgg atgaatgtca gctactgggc tatctggaca 4620
agggaaaacg caagcgcaaa gagaaagcag gtagcttgca gtgggcttac atggcgatag 4680
ctagactggg cggttttatg gacagcaagc gaaccggaat tgccagctgg ggcgccctct 4740
ggtaaggttg ggaagccctg caaagtaaac tggatggctt tcttgccgcc aaggatctga 4800
tggcgcaggg gatcaagatc tgatcaagag acaggatgag gatcgtttcg catgattgaa 4860
caagatggat tgcacgcagg ttctccggcc gcttgggtgg agaggctatt cggctatgac 4920
tgggcacaac agacaatcgg ctgctctgat gccgccgtgt tccggctgtc agcgcagggg 4980
cgcccggttc tttttgtcaa gaccgacctg tccggtgccc tgaatgaact gcaggacgag 5040
gcagcgcggc tatcgtggct ggccacgacg ggcgttcctt gcgcagctgt gctcgacgtt 5100
gtcactgaag cgggaaggga ctggctgcta ttgggcgaag tgccggggca ggatctcctg 5160
tcatctcacc ttgctcctgc cgagaaagta tccatcatgg ctgatgcaat gcggcggctg 5220
catacgcttg atccggctac ctgcccattc gaccaccaag cgaaacatcg catcgagcga 5280
gcacgtactc ggatggaagc cggtcttgtc gatcaggatg atctggacga agagcatcag 5340
gggctcgcgc cagccgaact gttcgccagg ctcaaggcgc gcatgcccga cggcgaggat 5400
ctcgtcgtga cccatggcga tgcctgcttg ccgaatatca tggtggaaaa tggccgcttt 5460
tctggattca tcgactgtgg ccggctgggt gtggcggacc gctatcagga catagcgttg 5520
gctacccgtg atattgctga agagcttggc ggcgaatggg ctgaccgctt cctcgtgctt 5580
tacggtatcg ccgctcccga ttcgcagcgc atcgccttct atcgccttct tgacgagttc 5640
ttctgagcgg gactctgggg ttcgaaatga ccgaccaagc gacgcccaac ctgccatcac 5700
gagatttcga ttccaccgcc gccttctatg aaaggttggg cttcggaatc gttttccggg 5760

-continued acgccggctg gatgatcctc cagcgcgggg atctcatgct ggagttcttc gcccacccca 5820
gcttcaaaag cgctctgaag ttcctatact ttctagagaa taggaacttc ggaataggaa 5880
ctaaggagga tattcatata tgcattaatg tctaacaatt cgttcaagcc gacgccgctt 5940
cgcggcgcgg cttaactcaa gcgttagatg cactaagcac ataattgctc acagccaaac 6000
tatcaggtca agtctgcttt tattattttt aagcgtgcat aataagccct acacaaattg 6060
ggagatatat catgaaaggc tggctttttc ttgttatcgc aatagttggc gaagtaatcg 6120
caacatccgc attaaaatct agcgagggct ttact 6155

<210> SEQ ID NO 2
<211> LENGTH: 15107
<212> TYPE: DNA
<213> ORGANISM: Shigella sonnei
<220> FEATURE:
<221> NAME/KEY: misc_feature
<223> OTHER INFORMATION: Ty21a-Ss tviD-vexA region (JX436479)
<220> FEATURE:
<221> NAME/KEY: mutation
<222> LOCATION: (11968)..(11968)
<223> OTHER INFORMATION: Only mutation that was detected when compared to GENBANK S. sonnei O-antigen gene cluster AF294823

<400> SEQUENCE: 2
cacgcaatat ttcaatgatg gcaacgcatt ctctgaagct ttccatgccg gcattcaatc 60
gcagcgccta aatgatacgt ttatggaaac ggcgttatct ttggcaatca aattcagtga 120
tgaattgatt ttcatgcatg cgctcgagca gctactccgc catgagtcag aatttgcgct 180
gacggtattg tcgacgattc atgataccgg tctcgttatc cgcacagctt tctgcatcaa 240
gaatatgagc tatcatcaag cgcttcgcac ctcgtataaa gataaaatcc acgacgtttt 300
tgaggcatgg aacaataccg cgctgtcgct acattcggtt gatgattttg tctcactgag 360
tacttcgcta gcctatagct actctgcatt tatggtttat ccccattcac gtatttctcg 420
ctttaataat gaagttaaaa tggcatggcg cgataaatta agagaaatgt atgagcgtga 480
ggattatgaa aatatcctgg caggggcgaa aatagtgtgg ccacttctga agtttgatcc 540
cgttggcacc gtatattgtg caagaacgct ggtgaatctt ggtgcctgga aagacgcgtg 600
cacgttggcc cacatgacct tgattcgtaa ctcgaacatt accagcctgc agtcgattat 660
gttacgcagc atacgtcata ttaacaacat tccgttcctc attgatttga ttgctaacgt 720
catgagcatt actctatcat tccagaatgc ctcaatgaac aagttgtttg agaaagagtg 780
tcgcaatgtt gcaaccagag cccttaaata tgtacgccag aagaaaactg aagggcgtct 840
ggatgaagca ttgtctgtat tgattagcct gaaacgaatt gagcctgatg tttctcgtct 900
gatgcgtgaa tataagcaaa ttatcagatt atttaatgag tcacggaagg atggcggtag 960
cactatcacg tcttatgaac atctagacta tgcgaaaaaa ttactcgttt ttgatagcga 1020
aaatgcctat gccttgaaat atgccgcatt aaatgcaatg catttacgcg actacacgca 1080
ggctttgcag tattggcagc gactggagaa agtgaatgga ccaacggagc cggtgacaag 1140
gcagatctcg acctgcataa ccgcattaca aaaaaataca tcagggaagt cgtaacccgg 1200
ggtgtaggct ggagctgctt cgaagttcct atactttcta gagaatagga acttcggaat 1260
aggaactaag gaggatattc atatatgcat taatgtctaa caattcgttc aagccgacgc 1320
cgcttcgcgg cgcggcttaa ctcaagcgtt agatgcacta agcacataat tgctcacagc 1380
caaactatca ggtcaagtct gcttttatta tttttaagcg tgcataataa gccctacaca 1440

```
aattgggaga tatatcatga aaggctggct ttttcttgtt atcgcaatag ttggcgaagt   1500
aatcgcaaca tccgcattaa aatctagcga gggctttact aagcttgatc aaatagctca   1560
tattcagcga gatttaacaa ctgcggaaca agccggaatc attgattatc gctctagcaa   1620
aggcggcttc gataatgcgc aaagtagcta taagttcttg ctcggcgaaa aactgttatc   1680
agcagagcta aaagcaacta aagatgcgcc aattatttac ccatttagat attacgaagt   1740
gaaacgtcaa attgatgagt tagaaggaat gttacgcgat aacattcagg cgcaagcata   1800
tcgatatcaa atgaagccat ctgagccagt tataaaagac aaacccaaca aagcattaat   1860
tttgattctt ggtgcattac caggggcaat gtttgctata gttggtacat tagtttatgc   1920
gacattaaaa gataaaacca agttagatta aactgggtta cgtattgttg tgtcaatgcg   1980
aaatagatgt tctatgtgca ctttatgatg gataagaaaa tgaaattcga tactttgaat   2040
gcgaaaattg ggattatagg ccttggttat gttggattgc ctcttgctgt tgagtttgga   2100
aagaaagtaa cgacgattgg atttgatatt aataagtctc gtattgatga attacgaaat   2160
ggtcacgata gtacattaga gtgctcaaat ttagagttgt tagaagcaac taaattgacg   2220
tacgcctgtt cattagatgc actaaaagag tgtaatgtat ttattgtaac tgttccaact   2280
ccaattgata aacataaaca gccagatcta acacctctaa ttaaagcatc tgaaacattg   2340
ggtaagataa taaagaaagg cgatgttatt atttatgagt caacagttta ccctggagcg   2400
acagaagaag attgtatacc agttgtagag aaagtatcag gtcttaagtt taatattgat   2460
ttttttgccg gttattcacc tgagcgtatt aatcctgggg ataaagagca tcgtgtaact   2520
aatatcctta aggtgaccag tggatctaca ccggatgttg ctgagtatgt agatcagcta   2580
tataaattaa taattactgt cggtacgcat aaagcatcat cgataaaagt agcagaggct   2640
gcaaaagtaa ttgaaaacac gcagcgagat gtcaatattg cattgattaa tgagttatct   2700
attatattta ataagttagg gattgatacc ttagaggttc ttgaggctgc aggtacgaag   2760
tggaattttt taccttttag gcccggttta gtaggtggcc actgtatagg tgtagatcct   2820
tattatctta cacataaagc gcaaagtgtc ggctatcatc cggagatgat tttagccgga   2880
cgtcgtttaa atgatagtat ggggcagtat gtcgtttccc agttagtcaa aaaaatgttg   2940
aaacaacgga ttcaagttga aggggcgaat gtgttagtga tggggcttac atttaaagag   3000
aattgcccag atctacgaaa cactaaagtg attgatatta tttcagagtt aaaagaatac   3060
aatatcaata tagatattat agatccatgg tgttctaccg atgaggcaca acatgaatat   3120
ggattaactt tatgtgaaga tcctaaagtt aatcattatg atgcaataat tatcgctgtt   3180
gcacacaatg agtttcgcga gatgggagag agcgctattc gtgcattagg taaagacgag   3240
cacgttttgt tcgatttaaa atatgtgctt gataaaaaaa gtatcgatat gcgcttgtaa   3300
gagtgattaa aaaaatcaaa tcctctttga tatgatacac ctcagcattt tatgctaggt   3360
ttagcacttg attaatatac atggatattt atatgtctcg ctatgaagag attacacagc   3420
agttaatttt ttcaccgaaa acttggttaa ttactggtgt cgctggcttt ataggatcaa   3480
atcttttaga aaagttactt aaattaaacc aggttgttat tgggttagat aacttttcca   3540
cgggacatca atataatctt gatgaagtta aaacattagt ttccactgaa cagtggagtc   3600
gattttgctt tatagaaggt gatattcgag atctcactac ctgtgagcaa gttatgaaag   3660
gtgttgatca tgtcttacat caggctgcgc taggttctgt acctcgttca attgttgatc   3720
ctataacaac caatgcaact aatattactg gatttttgaa tatcttacat gcggctaaaa   3780
atgcacaagt acaaagtttt acttatgctg catcaagctc aacttatgga gatcatcccg   3840
```

-continued

```
cactaccaaa agtagaggaa aacattggta atccactttc tccttatgca gttactaaat   3900
atgttaacga gatttatgct caggtatatg ctcgaacata tggttttaaa actattggat   3960
tacgttattt taatgtattt ggtcgtcgtc aagatcctaa tggagcttat gctgcagtaa   4020
ttccaaaatg gacagcagca atgcttaaag gtgatgacgt atatattaat ggcgatggtg   4080
aaacgagtcg tgatttttgt tatatagata atgttataca aatgaatata ttatctgcat   4140
tagcgaagga cagtgctaaa gataatatat ataatgttgc agttggtgat agaacaacgt   4200
taaatgaatt atctggttac atttatgatg agcttaattt aattcaccat atcgataaat   4260
tgagcattaa gtatagagag tttagatctg gagatgttag gcattctcag gctgatgtta   4320
ctaaggctat agatttacta aagtatagac caaatataaa aatcagagag ggattacgac   4380
tttcaatgcc gtggtatgtg agatttttaa aaggctaaat tatattaaca tgaataaata   4440
atctatttca cctctgttat taatgcaggg gtgaaaatcc atgtatttat tctaaatggt   4500
cagtgtatgt ttagaaaaat gattgatgca ggtggtacat ttttacttaa agcaatattt   4560
caaataggag tttttgttta tttcacacat gtgtcagata ttactacatt tggtattatt   4620
agttatgtgt ttactgttta ttggtttgtg cttaacttct ctgattatgg atttagaaca   4680
aaattagtga aagatatttc tgataatagt tattctgcat cagaattatt atcaagaagt   4740
gatggagtta aaacatatgt ttttttcttc atttttataa tcttcatgtt ttattcttat   4800
gtttctgatt caatttcatt aactctgctt gtttatattt catctgcata ttttgtttgt   4860
atttcaagtg gtagatttag cttgctacag gctgttggtc ggtttagatg tgaattatat   4920
ataaatatct actcaacaat tatatatatt gggtgtaatt tatttttatc tctgtttatc   4980
gaacctctat attatagtgc gatatcaata ttcatatact caatttcgct tttggttttc   5040
tcatcacata aatgcaatgt gccatgtttt catataaaaa gaccaagtat tttagtttat   5100
aaagattttt tggatgcaac tccgttcgct attctggtgt tactaaatgt tgttttatct   5160
agtattgacc tttttatatt aaaagaatat ttctcttata atagtgttgc tatatatcag   5220
gtggtaacta gggttaatac cggtctaata atagtgttta atgttattta tactgtttta   5280
ttgccttcat tttcttatta tctgaaaaat tctgaatggg gtaatataag gaaattacaa   5340
cgatatatat cactgttagt cttattacta tgtttatgct attatttttt tggcatctat   5400
ttcgtaggga tattgtttgg tgatgagtat aaggtaatat cttctgcaac atttttgata   5460
atgtttatgg ctcttattaa atataatttt tggctaataa atgaacttta tcttgtgtgt   5520
agtggaaatc aaagcgagcg agttaaatcg tattgtattg gtgtggtcat ttcaatggcg   5580
gttttctttt attttatacc tcggtatgga tggagtgggg cggtttttgg aagtgccatt   5640
gcaacattag taattggaat attttatatt atttctgtga aaaaagattg tgggaaaatt   5700
cttcatgata agtattcact aatgatgatc tttgtcccaa ttttctttta ttttattatt   5760
aatggtcagc agcggttgtt atattaatat gttgtggttt tatatcgttc cattaatatg   5820
tttagactcg attggaagcc taataaaggt taagtatgtt aatataccta tatcctgtac   5880
ttttgttatt taatatcctt ccggtttttt tttatggaca aatgaactct gatttagagc   5940
gttttttttgg agttcctatt ggctatattc cagatctaat attttatttc tttgttgttt   6000
taacatctat aataacgttg aggtttcacg tttctctgtg gacaaagaaa ttattatttt   6060
taggcatcat attcctgatt tatatcagca ttcagatgtt gttgttatca gcggatatat   6120
caggtgtcgt aattttatta tcgttttttt ctaattttat agctttggtt cttttggtgt   6180
```

```
cattttgcat tggtaaagat gagctttatt taactcattc ggttagaaat ataaatgttg   6240
taatgtgttt tggtattatc tgtggagttg taaaattatt tattggttat tctgaagata   6300
gtaattttat agtttattta aatagaaatg ccaccgcaat tatagtagtg tgcttttatt   6360
gtgtatattc atacttttat cgtggtcgaa agtcttggta tgtctcatct gtattgtact   6420
ctctgttctt tctttttctg gatagccgag caggaataat atcatttgct atatcgttgt   6480
tttttgtttt tcttcagtta acaaagaagg aaaagttatt aatatcattg tttttttgttc   6540
ctcttctaac tttaggtatt tcttttactg atataggcac tcgtcttgaa cgaatgctgt   6600
cttcgtcaca ggttatattc tctggtggta acactcttac aaaaagtcag aatgattatc   6660
gtcgagttga gttagtattt attggggttg atgttttaaa agaaaattat ttaattggca   6720
ctggattagg tgttgcaaat tatgtaaagg ctatagataa aaagttttta ggaagtacca   6780
actttgggtt ggcgcataat ttttatttat cttattcggc tcagttaggg attattggtt   6840
ttattttgct tatttctgta ttttatataa tgctgtctcc aatttttaaa tgcggagggt   6900
atattggtaa aggatgcgtt tttgctttgg ctttctatgt ctttttttaat gagtatatat   6960
tgacgccagc gatatatatt tatatttcta tttttttatc ggtggttttt atacgtaatt   7020
ctaaatagct gcgcggaata gtagatcact ttgagggaac ttagcccgga ttgtgcgatc   7080
tgatcaatcg ccaaatcaaa acaaatcacc aaccggactg agcaggatcc aagcgcagct   7140
atttaggatg agaatatgtt gttagaatat gttgaaagaa aaatttcctt agccttgagt   7200
aagtatccta aggtaaggga tgttattaag ttcttttatt tatatatcgc atcattattc   7260
ggaattattt tgaataaaaa taagacggtt attcaatcaa aaatatacga gatttcaatt   7320
gatgattctg aagaatcatt ttttggctat tatgaccata gtccaatgag ctctaatggg   7380
cggtacgtat tgttccactc tagtgcgttt agcactaaac gacatccaaa gaaagttaag   7440
tatatatcta tttgcgtaaa agaccttctt aataacaaag tttataagct atatgatacg   7500
cgagcattta attggcagca gggaagccga ttaatgtgga ttgatgatga caatataatt   7560
tttaatgact atgaaaataa tggatacatt agtgttgtct attctttgtc tttgatgaag   7620
gttataaaaa aaataaacta tccgatttat gatgtgaata attacaaggc tgtgacgtta   7680
gatttctcat ggctggctaa atatgatagc gattatggtt attataataa aaaatcattt   7740
tctacagata tttcaatcat taatttgaat acggggggaa tagaattatt tttatcctta   7800
gacgaaatgc taaagagaac taattttaaa tgtaatattg atgttgaaca tgtggtcaat   7860
cattttatgt ttgctcccga tggacgttcc gttatgttca tacatcgata ctatacacct   7920
aaaggaaagc gtgaaaggtt aatacattgg aatttaataa atgataatgt tcgagtccta   7980
ataaatgaat cgattattag tcattgttgt tggaatggga atgatgaaat tataggtttt   8040
tttggtgcag aaatagattc gctaaattat tatagattgt caattgaatc ctgtaataca   8100
gagaaattgt tttttgatgc aagaaaatat tctgatggac atcctactat agttcataat   8160
agatatatta tatctgatac ttacccagat aaaaaatagaa ttaaaaagtt gtttgtttat   8220
gaccttgtca aaaatgatta tcgcgagctt ggattatttt atgagtcaat gagttttttt   8280
tcttattctc gatgtgactt acatccaagg atctcggttg ataatagatt tttgtttgtt   8340
gattcagttc actcagggaa aagaaaacta tattttatga ggagtggtat ttgtgagtga   8400
tgttctagta tctttaatta tagtttgctt taatgcagag aagtatattg aaaaatctct   8460
tttggcattt attaatcaag atgttggatt agataaattt gaattgatta ttgtagatgg   8520
ggattcatct gataatacaa tatctattgt tcaggatgtt ttttctaaac atagcaacat   8580
```

-continued

```
taagcataaa attatcaata ataaaaaaag aactcttgct acgggttgga atattggggt   8640
gctagaagct aatggtaagt ttgtgtgtag agttgatgca catagtgata ttccaaataa   8700
ctatatatct aaattattag atgattattt taatattatg cagtttgatg atagcgttgt   8760
tggtgttgga ggtgtattaa ctaattctta taaaactaag tttggttcaa ttgtagcgga   8820
tttttatgca tcgaaatttg gtgttggtaa ttctccattt aggtgcgtag acaaaaataa   8880
tcgactaaaa aaaacagata cagctgtctt tgctttatat aataaagatg tgtttttga    8940
tgttggactt tttaatgaag tattagatag aaatcaagat attgattttc ataagagagt   9000
tttaagcaat aatttgtcat tatatacaga taatagttta tttgttgagt attatgttag   9060
agataatttt aaagatttca taaagaaagg ttttcttgat ggtttttggg ttgttatgtc   9120
tggagcatat tattttagac atatagtgcc acttttttt gttttgtatt taattgtatc    9180
tttttctctt ttctttgcta ctggtgatta tatatattta tctttttat tttttattt     9240
tcttatttct attttgtttt caattcgaga tgggcgaagt tttataggta gagtatttct   9300
tccttttata tttttgtctt atcatatttc ttatggatgt ggatcgttat tatcttttt    9360
gaaaaggtat tttaaatgaa aaattttatt ccttttgcgt tacctgaaat tggcgaagaa   9420
gaaattgcag aggtaattga ctctttacgt tcaggttgga ttacgacagg tcctaaggct   9480
aagcaatttg aacaagaatt ttctaattac ctaggagcga acgttcaatc attagctgtt   9540
aactctgcta cgtcgggctt acatttggct cttgaagctg ttggcgtaaa gccgggagac   9600
caagttattg tcccatcata tacattcact gctactgccg aaattgtcag gtaccttggt   9660
gctgatcctg taattgttga tgtagatcgt aaaacattta atatatcagt tgatgccatt   9720
gagaaggcta ttactaatga aacaaaggcg attattccag tacacttcgc tggattagct   9780
tgtgacatgg attcaatctt atcaattgct aaaaaatatg acctaaaggt tgtcgaggat   9840
gccgctcatg catttcctac aacatataaa ggaagtaaga taggaacgct tgattcagat   9900
gctacggttt ttagcttcta cgccaataaa actatgacaa ccggtgaagg cggaatggtt   9960
gtttcaaaaa ataaagatat aattgagcgt tgtaaggtaa tgcgtttaca tggaatcagt  10020
cgtgacgctt ttgaccggta ccagtctaaa actccttctt ggttttatga ggttgtagct  10080
ccagggttta aatacaatat gcctgatatc tgtgcggcaa tcggtattca tcaacttaga  10140
aagatcgatg attttcagaa aaaacgtcaa cgaatggcaa aaatttacga tgatgcgtta  10200
aaagaattgc cacttgaatt gcctgaatgg cctactaatg ctagtgatat tcatgcttgg  10260
catctatatc ctatccgctt aaaaactgat tcggctatta atcgcgatga ttttattaag  10320
aagttatcag atcttggaat tggttgttct gtccatttta taccgttgca taagcaaccg  10380
gtttggcgtg atacatataa tttgaacgcc agtgactttc cagtttctga ggagtgttat  10440
ttaaatgaaa tatctattcc tctttatact aaaatgacgg atcaagatca gttgttcgtt  10500
atcaaatcga ttagacaatt atttatgtaa tggtatttta tattaaatga aacgtatttt  10560
tgatgttatc gtggcaggct taggcctgct tttctatttt cctgttttta tcattgtgtc  10620
aatgttaatt gttgctgatt ctaaaggggg ggtttttttt aggcagtata gagttgggag  10680
atttgggaaa gattttagga tacataaatt tagaacgatg tttatcgatt cagaaaaaaa  10740
aggacggata acagttggtc aagatgctcg ggtaaccaga gttggatggt atttacggaa  10800
gtacaaaatc gatgagcttc ctcaattgat agatgttctt tctggaacaa tgagtttggt  10860
tggcccaaga ccggaagtga gggagtttat tgatgagtat cctgatgata taagggaaaa  10920
```

-continued agttttatcg gttaggccag ggataactga cttagcatct atagaaatgg tagatgaaaa 10980
tgagattttg tctagttatg atgacccacg tagggcttat atagatataa ttcttccaat 11040
caagcaaaga tattatttag attatgttgc taacaattca gtaaagtatg attgtgtgat 11100
aatttggaaa actattatta agattttgtc gcgataataa ggtagtgtag gatgattgat 11160
agaatattgg agctgccaag aattgttaag agaggtatca tcatctgcat tgatgtagtt 11220
atggtgatat tctcattttg gttgtcttat tggttgaggc ttgatgagca aacggctttt 11280
cttagtgcac cgatgtggtt tgctgcagct attcttacca tatttaccgt gtttatattt 11340
atcaggattg ggctttatcg ggcagtctta cggtatgtta gtgcaaagat aatgttgcta 11400
ataccagttg gtattctggc ctcaacgtta tctcttgtcg ttatatcata ttcgctatcc 11460
ataatgttgc cgcgcactgt tgtcggaatt tattttttgg ttttactttt actgacatca 11520
ggctctagat tgctttttag aatgatactt aactatggag ttaagggtag tgcgcctgtt 11580
ttgatttatg gcgctggtga atctggccga caattattgc cagcattaat gcaggcaaaa 11640
gaatattttc ctgtggcatt tgtggatgat aatcctcgct tgcataaggc tgtcattcat 11700
ggtgtaacag tttatccctc ggataaactg agttaccttg tagatcgcta tggtataaag 11760
aaaattcttt tggcgatgcc gagcgtcagt aagtcacaaa ggcagaaagt gattactcgt 11820
ttagagcatc taccgtgtga agttctctct attccgggta tggtcgattt agtcgaaggt 11880
cgagcacaaa tcagtaatct aaaaaaagta tcgattgatg acttactagg tcgtgatccg 11940
gttgctcctg atgccaaatt gatggccaaa aacattactg gcaaagccgt tatggtcact 12000
ggggcgggag gctcgatcgg ctctgagctt tgtcgtcaaa ttgttcgata taagccggcc 12060
aaattggttc tatttgaact gtctgaatat gccctctacg ctattgagaa agagctctcg 12120
gcgctgtgcg acaaagaagt tttgaatgtt ccagtgatcc ctctgttggg ctcggtgcag 12180
cgtcagaatc gcttacagat ggtgatgaag tcctttggta ttcaaacggt ttatcatgcg 12240
gccgcttata aacatgtgcc tctggttgag cataatgtgg tggaaggggt acgtaataac 12300
gtgtttggta ccttgtactg cgctgagtca gcgatcgaaa gtggcgttga aacttttgtg 12360
ttgatttcca ccgataaagc ggtgcgcccg accaacacta tggggacaac taagcgtctg 12420
gccgaattgg tattgcaggc tttgtctgca cggcaaagcc aaactcgctt ttgtatggtg 12480
cgatttggta atgtactcgg ttcttcgggc tctgtcgtgc cgttgtttga aaaacagatt 12540
gcccaaggtg ggccagttac cttgactcat cgtgacatta ttcgctattt catgacaatt 12600
ccggaagcat cacagttggt gattcaagcg ggggcgatgg ggcatggcgg cgatgtcttt 12660
gtcttagaca tgggcgatcc ggtcaagatt tatgacttag ccaaacgcat gatccggtta 12720
agtggcttga gtgtacggga tgataaaaat ccagatggcg atattgccat tgaagttacg 12780
ggattacgtc caggggagaa actgtatgaa gaattactga ttggtgattc agttcaaggt 12840
acctctcatc cacgaattat gacggccaac gaagtgatgc taccgtggca ggatctatcg 12900
ctcttactta aagagctgga tcaagcttgt catgactttg atcatgagcg aattcgcagt 12960
ttgttgttac aagcaccagc ggcattcaat ccaactgatg atatttgcga tctagtttgg 13020
cagcagaaaa aatcgctgtt atcacaagcg agcaatgtca ttcgcctgtg attgcttagg 13080
tttaaccttc cacaccaatt cttcacctct cttacaaatc cccgctaggc ggtacatcgt 13140
gaccgccttt agcctgatgc ctgctcttta acaaacagga catcagtgta tgtttaaacc 13200
ttttagcgcc gaatttttcg gcactttctg gctggttctg ggtggctgtg gtagcgcctt 13260
gatctctgct gctttcccac agttaggtat aggctttttg ggcgtggcgt tggcgtttgg 13320

```
tctgacagta gtcaccatgg cttatgcggt cgggcacatc tctggtgcgc attttaaccc  13380

cgcggtgacc ttgggtctgt gggccggtgg acgcttccca gcagcgcgcg tgttacctta  13440

cattatcgct caggttatcg gcggtattgc cgctgcggca gtgctgtatg gtatcgccag  13500

cggtaaggct gggtttgatg cgacaaccag cggttttgcg gctaatggtt atggcctcca  13560

ttcacctggc ggctatgcgt taagcgcctg tatgctgagc gagtttgtcc tcagtgcgtt  13620

ttttgtccgg agcgacagaa aaacgcgctc ctgcgggctt tgcgccactg gcgattggtc  13680

tggtaatcac cccgtaaatt aactcgagta attaatgggc atcatttttc agctatttca  13740

tttataaaat aagttatgaa aaaaatcatc atattactaa cgacattttt cctgctttcg  13800

ggatgcacta ttcccagggc ggtatttaaa tccagcctta ttaatcagga cgatcctcgt  13860

tataatctgg tcgaagtcac gccgacatta aaactaagcg ctcccgatac tgtgccgaaa  13920

actattgtcg atccggtttt tgccgcaaat aactggcact ggacatcttt ggctaaaggc  13980

gatgtgctgc atatcactat tttatcctcg ggcggggctg gatatttatc caataacgcg  14040

agcggcgacc gtgcggattt tgaaaatatt cttgtgactg acagtaatac cgttcaggtg  14100

ccttatgccg ggacaatccc ggtttctgga ttggatgtga cgcaactggc tgatgagatc  14160

aaaaagcgac tttcgcgcgt tgtcctgaat cctcaggtga ttgtgacact taccgcccgc  14220

accggagcca tggtgacggt cgagggcagc gggaaaacgg gtcgataccc tctcgaacag  14280

agtatgaatc gtctgagtca tcttttggca acggcagtgg cagtagaaaa taccagcaca  14340

gatatgatgg aagttcacgt gacgcgccag cagcattatt tcactgcgcg actgtcagat  14400

atttatcagt atcccggatt ggatattgcc ttacagccgg atgaccgtat cactctgcgt  14460

caagtgaccg agtatgttaa tgtgctcggc gcagcaggtg ttcaggggaa acatgctctg  14520

gttcagcgtc attccagcgt cgtggatgct ttggcgctcg cgaaaggatt aaatgacaat  14580

cttgccgatc cgcaagcgat ttttctgtac aagcataacg aagcggaaca ggcgaaacag  14640

cagatgcgta agctgaatat ctatcatgtc gatatgagcc aacctaactc ggtgttttta  14700

gcgcaggcca tacgagtgga caacggcgat gttatctata tctcgaacgc ctctttgact  14760

gatttcgcta aggtgaaagc cgcattcgat agctttttga cccgcggcac taattctttc  14820

taatgtcgcc atatgaatat tttgaaaaat aattcttatt attttatgaa actcattacc  14880

gtctgtgagt taattatttt attgatgtca cgcgatatca aaacacgcta taacggtaat  14940

ttactaaact atatgatggt gctggccgta ccactggtat ggatatccat taccgttatt  15000

tcttttcaat atttaaatcg ctcggtgcca atatccactg acgatatcag ttttgttatt  15060

gcagggatat taccgtatct gttatttcgt tataccatta ccgcaac                15107
```

<210> SEQ ID NO 3
<211> LENGTH: 9297
<212> TYPE: DNA
<213> ORGANISM: Shigella dysenteriae
<220> FEATURE:
<221> NAME/KEY: misc_feature
<223> OTHER INFORMATION: O-antigen (AY585348)

<400> SEQUENCE: 3

```
ctctctgaat actcggtcat ccagaccaaa gaaccactgg accgtgaagg taaagtcagc     60

cgcattgttg aattcatcga aaaaccggat cagccgcaga cgctggactc agacatcatg    120

gccgttggtc gctatgtgct ttctgccgat atttggccgg aactagaacg cactcagcta    180

ggtgcatggg gacgtattca gctgactgat gccattgccg aactggcgaa aaaacagtcc    240
```

-continued

```
gttgatgcca tgctgatgac tggagacagc tacgactgcg gaaaaaaaat gggctatatg    300
caggcgtttg tgaagtatgg gctgcgcaac ctcaaagaag ggcgaagtt ccgtaaaggg    360
attgagaagc tgttaagcga ataatgaaaa tctgaccgaa tgtaacggtt gataagaaaa    420
ttataacggc agtgaagatt cgtggcgaaa gtaatttgtt gcgaatattc ctgccgttgt    480
tttatataaa caatcagaat aacaaagagt tagcaatagg attttcgtca aagttttcca    540
ggattttcct tgtttccaga gcggattggt aagacaatta gtgtttgaat ttttcgggtt    600
tagcgcgagt gggtaacgct cgtcacatcg tggacatgta tgcagtgctc tggtagctgt    660
aaagccaggg gcggtagcgt gcattaatac ctctattaat caaactgaga gccgcttatt    720
tcacagcatg ctctgaagta atatggaata ataaagtgaa gatacttgtt actggtggcg    780
caggatttat tggttctgct gtagttcgtc acattataaa taatacgcag gatagtgttg    840
ttaatgtcga taaattaacg tacgccggaa acctggagtc acttgctgat gtttctgact    900
ctaaacgcta tgtttttgaa catgcggata tttgcgatgc tgctgcaatg gcgcggattt    960
ttgctcagca tcagccggat gcagtgatgc acctggctgc tgaaagccat gtggatcgtt   1020
caattacagg ccctgcggca tttattgaaa ccaatattgt tggtacttat gtccttttgg   1080
aagcggctcg caattactgg tctgctcttg atggcgacaa gaaaaatagc ttccgttttc   1140
atcatatttc tactgacgaa gtctatggtg atttgcctca tcctgacgaa gtaaataata   1200
aagaacaatt acccctcttt actgagacga cagcttacgc gcctagtagt ccttattccg   1260
catcaaaagc atccagcgat catttagtcc gtgcgtggaa acgtacctat ggtttaccga   1320
ccattgtgac taactgttcg aataactacg gtccttatca ctttccggaa aaattgattc   1380
cactagtaat tcttaatgct ctggaaggta aggcattacc tatttatggc aaaggggatc   1440
aaattcgtga ctggctgtat gttgaagatc atgcgcgtgc gttatatatc gtcgtaaccg   1500
aaggtaaagc gggtgaaact tataacattg gtggacacaa cgaaaagaaa aacatcgatg   1560
tagtgctcac tatttgtgat ttgttggatg agattgtacc gaaagagaaa tcttaccgcg   1620
agcaaattac ttatgttgcc gatcgcccgg gacacgatcg ccgttatgcg attgatgcag   1680
agaagattag ccgcgaattg ggctggaaac cgcaggaaac gtttgagagc gggattcgta   1740
aaacggtggg atggtacctc tccaatacaa aatgggttga taatgtaaaa agtggtgcct   1800
atcaatcgtg gattgaacag aactatgagg gccgccagta atgaatatcc tcctttttcgg   1860
caaaacaggg caggtaggtt gggaactaca gcgtgctctg gcacctctgg gtaatttgat   1920
tgctcttgat gttcactcca ctgattactg tggtgatttt agtaatcctg aaggtgtagc   1980
tgaaaccgta agaagcattc ggcctgatat tattgtcaac gcagccgctc acaccgcagt   2040
agacaaagca gaatcagaac cggagtttgc acaattactt aacgcgacga gtgtcgaagc   2100
gatcgcgaaa gcagccaatg aagtcggcgc ctgggttatt cactactcta ctgactacgt   2160
atttccgggg accggtgaaa taccatggca ggaggcggat gcaaccgcac cgctaaatgt   2220
ttacggtgaa accaagttag ctggagaaaa agcattacaa gagcattgtg cgaagcacct   2280
aattttccgt acaagctggg tctatgcagg taaaggaaat aacttcgcca aaacgatgtt   2340
gcgtctggga aaagagcgtg aagaattagc cgttattaat gatcagtttg gtgcgccaac   2400
aggtgctgaa ctgctggctg attgtacggc acatgcaatt cgtgtggcag tgaataaacc   2460
agaagtcgca ggcttgtacc atctggtagc cactggtacc acaacctggc acgattatgc   2520
tgcgctggtt tttgaagagg cacgaaaagc aggtattccc cttgcactca acaagctcaa   2580
```

-continued

```
cgcagtacca acaacagctt atcctacacc agctcgtcgt ccacataact ctcgccttaa   2640
tacagaaaaa tttcagcaaa attttgcgct tgttttgcct gactggcagg ttggcgtgaa   2700
acgaatgctc aacgaattat ttacgactac agcaatttaa tagtttttgc atcttgttcg   2760
tgatgatgga gcaagatgaa ttaaaaggaa tgatgtaatg aaaacgcgta aaggtattat   2820
tttagcgggt ggctctggta ctcgtcttta tcctgtgact atggctgtca gtaaacagct   2880
attacctatt tatgataagc cgatgatcta ttacccgctc tctacactga tgttggcggg   2940
tattcgcgat attctgatta ttagtacgcc acaggatact cctcgttttc aacaactcct   3000
gggtgatggt agccagtggg ggttaaatct tcagtacaaa gtgcaaccga gtccagatgg   3060
tcttgcgcag gcatttatca tcggtgaaga gtttatcggt ggtgatgatt gtgctctggt   3120
tctcggtgat aatatcttct acggtcatga tctgccgaag ttaatggatg tcgctgtcaa   3180
caaagaaagt ggtgcaacgg tatttgccta tcacgttaat gatcctgaac gctacggtgt   3240
tgttgagttt gataaaaacg gtacggcaat cagcctggaa gaaaaaccgc tacaaccaaa   3300
aagtaattat gcggtaaccg ggctttattt ctatgataac gacgttgtcg aaatggcgaa   3360
aaaccttaag ccttctgccc gtggtgaact ggaaattacc gatattaacc gtatttatat   3420
ggagcagggg cgtttatccg ttgccatgat gggacgtggt tatgcatggc tggacacggg   3480
gacacatcaa agtcttattg aagcaagcaa cttcattgca acaattgaag agcgccaagg   3540
gttaaaggta tcttgcctgg aagagattgc ttatcgtaaa ggctttattg acgcagagca   3600
ggttaatgta ttagccgaac cgctaaagaa aaatgcttat ggtcagtatc tgttgaaaat   3660
gattaaaggt tattaaaaat gaatgtaatt aaaactgaaa ttccagatgt attaattttc   3720
gagccgaaag tttttggtga tgaacgtggt ttttttatgg aaagctttaa ccagaaagtt   3780
ttcgaagagg ctgtagggcg gaaggttgaa tttgttcagg ataaccattc taaatcaact   3840
aagggtgtgt tacgcggact gcactatcag ttggaacctt atgctcaagg taaattagtt   3900
cgttgtgttg tcggtgaagt ttttgatgta gcagttgata ttcgtaaatc gtcacctaca   3960
tttgggaaat ggattggggt gaatttgtct gctgagaata agcgtcagtt gtggatacct   4020
gaaggatttg cgcatggatt tttggtgctg agtgaaacgg ctgagtttgt ttataaaaca   4080
acaaactatt acaatccaag ttttgaaaaa agtatttcat actcagatcc taccattaaa   4140
attcagtggc ccaatttaca ggatatgcat tttaaattat caaataagga tttgaatgct   4200
aagaactttt ttaatgacaa tagtttaatg caatgaagaa aaatatattg ctcttgttct   4260
tagtacatgg ggcaaattat ttgttcccgt ttatagttct tccatatcaa actcgaatat   4320
taagcatcga gacattcgca gatgtagcaa aaattcaagc cgctgtgatg cttttatctt   4380
taatcgtaaa ttatggatat aacttatcaa gtacaagagc tatagctagg gccgtatctc   4440
aagcagaaat aaataagatc tatagtgaga ctcttattgt aaaattatta ttggcaacca   4500
tttgtcttgc acttggttgc gtacatttga tgtatgtcaa agagtactca ttgatatatc   4560
cttttataat cagttcgata tatctttatg gtagtgcatt atttgctact tggttattcc   4620
aaggacttga gaaaatgaaa gcggtcgtta tagcaacaac aatcgctaaa ctgactggtg   4680
tgatacttac ttttatttta gttaagtctc caaatgatat agttgcagct ctttttacac   4740
aaaacattgg gatgtttata agtggtataa tatctattta tttggtaagg aaaaacaaat   4800
atgcaaccgt aatatgtttt cgacttaaaa atattattgt aagcttaaaa gaagcgtggc   4860
cgtttttttt atcattagct gcaacaagtg tatatacata ttttaatgtg attttattat   4920
ctttttatgc tggcgactat gttgtggcaa attttaatgc tgctgataaa ttaagaatgg   4980
```

-continued

```
ctgctcaagg gttacttatt ccaataggac aggctgtttt cccacgatta tctaaactag   5040

agggctatga atatagttct aaacttaaaa tttatgcaat aaggtatgct atttttggtg   5100

tttgcattag tgcgggactt gtatttttag gtcccatgtt aactactatt tatttaggca   5160

aagaatattc gttgtcagga gaatatcttc aaagtatgtt tttactacct gccactattt   5220

caatatcgac tatactgagt caatggatgt tgatacctca aggcaaagaa aaaatattaa   5280

gcagaatcta tattctaggc gccattgtcc atttattata tgcatttcct ttagtttact   5340

attatggggc ttggggcatg gtaatatcaa ttttatttac tgaagtctta attgtattat   5400

ttatgcttaa ggctgtgaaa tgacttactt tactggtttt attttaatat tgtttgctat   5460

tataattaaa agattaactc caagtcaaag caagaaaaat attgtcttaa tagctaatgc   5520

gttttgggga atattgttgg taggttatgc tttcaatgaa caatatttcg taccattaag   5580

tgcaacaacc ttgtttttta tacttgcatt cttatttttc tttagtatga cttatatttt   5640

aattgctagg agtggaaggg ttgtttttttc tttcggtact ggttttatag aaagcaaata   5700

tatttactgg tttgctggga tgattaatat tattagtatc tgctttggca ttatcctttt   5760

atataataat catttttctt taaaagtaat gagagaagga attttagatg gttctattag   5820

tgggtttgga ttggggataa gtttgccact ttccttctgc tgtatgtatt tagcaagaca   5880

tgagaataaa aaaaattatt tctattgttt tacactactt tcattcttgc ttgcggtgtt   5940

atcaacttca aagatcttct taatattatt ccttgtatat attgttggaa taaatagtta   6000

tgtaagcaaa aagaaattgc ttatttatgg agtgtttgta tttggactgt tcgctttatc   6060

aagtattatc ttgggtaagt tctcttcaga ccctgaaggc aagattattt cagcaatatt   6120

tgatacgtta agggtttatc ttttctcggg attggcagcc tttaatcttt atgttgaaaa   6180

gaatgccacg ctccccgaaa atttactttt gtatccattt aaggaggttt gggggacgac   6240

aaaagatatt cccaaaactg atattttgcc ttggatcaac attggtgtat gggacacgaa   6300

tgtatataca gcttttgcac catggtatca gtcattggga ttatatgcag ctataattat   6360

tggtattctc ttagggtttt attacgggat atggtttagc tttcgtcaaa atttagctgt   6420

gggtttttat caaacatttt tgtgttttcc tcttttaatg ttgtttttcc aggagcatta   6480

tttgttgtca tggaaaatgc attttattta ttttttatgt gcaattttat tagcgatgag   6540

aaaagcatta gagtatgaat aaatattgta tcttagtact atttaatcca gatataagtg   6600

tttttattga taatgtcaaa aagattttat ctttggatgt aagtttattt gtatatgaca   6660

attcagcaaa taaacatgca ttccttgctc tatcctcaca agagcaaaca aagataaatt   6720

acttttcgat atgtgaaaat atcggattgt cgaaagctta taatgagaca ctaaggcata   6780

ttcttgaatt taataagaat gtgaaaaata aaagcattaa tgatagtgtg ctttttctcg   6840

accaagactc tgaagttgat ttaaattcca tcaatatttt gtttgaaact atatcagcag   6900

cagagtctaa tgtgatgata gtcgcgggga atcccataag gagagatgga ctaccgtata   6960

tagattaccc ccacactgta aacaatgtaa aatttgtaat tagtagttat gctgtgtatc   7020

gcttagacgc atttagaaac atcggcttgt ttcaagaaga ttttttttata gatcatatcg   7080

atagtgattt ttgttcaagg ctgataaaaa gcaattacca aattctcctt agaaaagatg   7140

ccttttttta tcaaccaata ggaataaaac cattcaatct ctgtggtaga tatttattcc   7200

ctatcccatc acaacaccga acatattttc aaattagaaa tgcttttttta agttacaggc   7260

gcaatggtgt tacatttaat tttttattta gggaaattgt aaatagattg attatgagta   7320
```

-continued

```
tattctcagg ccttaacgag aaagacttat tgaaacgatt gcatttatat ttaaaaggaa   7380

taaaagatgg tcttaaaatg taattcttgg ctagaagtgg gggcgttgtg attaaaaaaa   7440

aagtggcggc gataattata acatataatc cagatctaac aattctgcga gaaagttata   7500

cgagtctata taagcaagtc gataaaataa ttcttattga taacaactct acaaactatc   7560

aagaacttaa gaagttattc gaaaaaaaag aaaaaataaa aatagtgccc ttgagtgata   7620

atataggact agcagcagct caaaatttag gtttgaactt agctattaaa aataactata   7680

cttatgctat tttattcgat caggatagcg tcttacaaga caatggaatt aacagtttct   7740

tttttgaatt tgagaaatta gttagtgaag aaaaattaaa tatagttgcc attgggccaa   7800

gtttttttga cgaaaagaca ggaagacgct ttcggcctac aaaatttatc ggtccctttt   7860

tatatccctt tcgtaaaata accacaaaaa atcctctaac agaagttgac ttcttgattg   7920

cttctggttg tttcataaaa ttggagtgta ttaaatcagc cggaatgatg actgaatcgt   7980

tattcatcga ttatattgat gttgaatggt catatcgtat gcgttcgtat ggctataagc   8040

tatatattca taatgatatt cacatgagtc atttagtggg agaatctcga gttaatttag   8100

gattgaaaac tatttcttta catgggccgc taagacgata ttacttattt aggaattata   8160

tttcaatttt aaaagtgaga tatataccgt taggatataa aatacgtgag ggttttttta   8220

atatcggaag atttttggta agtatgatta taactaaaaa tagaaaaact ttaattttat   8280

acactataaa agcaattaag gacggaataa ataatgaaat ggggaaatat aaaggctaac   8340

aacatattat gaaaaaaata atacataacc aagtgttgcc gaaaatgtct gggattcagc   8400

aaatctcttt tgatattttg tcaggtctta aagacaagga tgtacaaaaa tttatattat   8460

gcggtttacc agatggcagt tcagataatg aatttaaaaa gaaatttact gatataggtg   8520

ttagggttat tacgatacct acattaaaac gaaatatcgg gtggcatgac tttcgatgtt   8580

tcattgattt atacaatttt tttaaaaaag aaaaatttga tatagttcat acaaactcaa   8640

ctaagccagg aataatagct agaatagccg ctagattagc cgggacaaaa ctcattattc   8700

acacagtaca tggaatcgca tttcatagaa aagaaaatac tgtaaggaaa attttgcgac   8760

tctttttggt agcattaatg tgacagtgaa cgagaattat ttaaaatatt atccattcgt   8820

taaaagtcat attatatata atggagttga tttcaacgtt ctttgctgca ataaaaagga   8880

ttatgatttt ttacatattg catttatggc tagacttgat aaacaaaaaa accattggag   8940

tttataagag ccgttaatat tattaagaaa aaattaccaa atgagcgttt gaaatttaca   9000

ttagctggct gtggtgagtt agaaaatgaa tgtaaaaaat taatagaata ttttcatctt   9060

acagatgtta ttgatatgcc tggatggata gtagataaaa acacgtttta taactctgtc   9120

gatattattt gccagccatc caattgggtg gcttttggct tagtatttgt tgaggccgcc   9180

ttttttgaaa ttccatctgt ttcaaggaat atcgaaggga ttcctgaggt tattttagat   9240

aatgaaactg ggcttttgta tgagggcgga gaagccgagt tgagtgaaaa gctgata      9297
```

<210> SEQ ID NO 4
<211> LENGTH: 1507
<212> TYPE: DNA
<213> ORGANISM: Shigella dysenteriae
<220> FEATURE:
<221> NAME/KEY: misc_feature
<223> OTHER INFORMATION: wpp (AY763519)

<400> SEQUENCE: 4

```
tcagcgtttt tcagaggact acatgtcatg gcttgttatc gtttataata aaaaaacaaa     60
```

-continued

```
tgtggattaa tatatggaag ggatttggtt tttctcgata aatttaactt tggagtgtca    120

gggttgagtg gtaatttatg gttgatggag aagtgggagt taaaaaatat atttaacttc    180

ttgttgaaag gtaaaataat ggcagtgcct gcgatcttgt tttctttgat aaaatatgaa    240

agaagatgcg ctttaacaaa gaaaaataaa ggtaagggta ataaataatg aagatctcaa    300

taatagggaa cacagcaaat gctatgattt tgtttagatt ggatttaata aaaacactaa    360

ccaagaaagg gatttcagtc tatgcttttg ctactgacta taatgattca tccaaggaaa    420

taataaaaaa agcaggcgcc attcctgttg attataattt aagtcgcagt ggtattaacc    480

ttgctggtga tttatggaat acttacttat taagtaaaaa actaaagaag ataaaaccag    540

atgctatttt atcttttttt tcaaagccct ctatctttgg atcgttggct ggtatttttt    600

caggcgttaa aaataataca gctatgcttg aggggttagg ttttttattt acagagcagc    660

cacatggaac tccgttaaaa acaaagttac ttaaaaatat ccaggttctc ctgtataaaa    720

taatatttcc acatatcaac tcattaatac tccttaacaa ggatgattat catgatttga    780

tagataaata caaaataaaa ttaaaatctt gccatattct tggtggcatt ggtttagata    840

tgaataatta ctgtaaaagc acgccaccaa caaatgaaat atcattcatt tttatagctc    900

gtttgctagc agaaaaagga gtcaatgagt ttgttgctgc cgcaaaaaaa ataaaaaaaa    960

cacatcccaa tgttgaattt attatacttg gcgctataga taaggaaaac cccggagggt   1020

tatctgaatc tgacgtagat actttaatta aatcaggagt tatttcttat cccggatttg   1080

tttctaatgt ggctgattgg attgaaaaat caagcgtatt tgttcttcct tcctattatc   1140

gagagggagt tcctcgtagt acacaagaag cgatggctat ggggaggccg attttaacta   1200

ctaatttacc aggctgcaaa gaaacaatta ttgatggtgt gaatggatat gttgtaaaaa   1260

aatggtcaca tgaagatctt gcagaaaaaa tgctgaagtt aattaataat cctgaaaaaa   1320

taatcagtat gggagaagaa agttataagt tagcaagaga aagattcgat gcaaatgtaa   1380

ataatgtaaa gttattaaaa atactaggga ttcctgatta ataaacgaaa agcggctctg   1440

attcattcgg aactaagaac ctatctcaat aggagctaaa ttcatgacct tacccagcca   1500

tatcgat                                                               1507
```

<210> SEQ ID NO 5
<211> LENGTH: 37
<212> TYPE: DNA
<213> ORGANISM: Shigella sonnei
<220> FEATURE:
<221> NAME/KEY: misc_feature
<222> LOCATION: (7)..(12)
<223> OTHER INFORMATION: Restriction site: primer prMD31.pGB.2.F.Nsi

<400> SEQUENCE: 5

```
tcatatatgc attaatgtct aacaattcgt tcaagcc                              37
```

<210> SEQ ID NO 6
<211> LENGTH: 36
<212> TYPE: DNA
<213> ORGANISM: Shigella sonnei
<220> FEATURE:
<221> NAME/KEY: misc_feature
<222> LOCATION: (7)..(12)
<223> OTHER INFORMATION: Restriction site: primer prMD32.pGB2.R.NheI

<400> SEQUENCE: 6

```
ctacacgcta gcacgctact tgcattacag cttacg                               36
```

<210> SEQ ID NO 7
<211> LENGTH: 33
<212> TYPE: DNA
<213> ORGANISM: Shigella sonnei
<220> FEATURE:
<221> NAME/KEY: misc_feature
<222> LOCATION: (7)..(12)
<223> OTHER INFORMATION: Restriction site: primer prMD33.KD.F.NheI

<400> SEQUENCE: 7
tagcgtgcta gcgtgtaggc tggagctgct tcg 33

<210> SEQ ID NO 8
<211> LENGTH: 42
<212> TYPE: DNA
<213> ORGANISM: Shigella sonnei
<220> FEATURE:
<221> NAME/KEY: misc_feature
<222> LOCATION: (7)..(12)
<223> OTHER INFORMATION: Restriction site: primer prMD34.KD.R.NsiI

<400> SEQUENCE: 8
acattaatgc atatatgaat atcctcctta gttcctattc cg 42

<210> SEQ ID NO 9
<211> LENGTH: 41
<212> TYPE: DNA
<213> ORGANISM: Shigella sonnei
<220> FEATURE:
<221> NAME/KEY: misc_feature
<223> OTHER INFORMATION: prMD35.pGB.MCS.F.p

<400> SEQUENCE: 9
tcgaggggcg cgccggtacc gaattcccga cagtaagacg g 41

<210> SEQ ID NO 10
<211> LENGTH: 40
<212> TYPE: DNA
<213> ORGANISM: Shigella sonnei
<220> FEATURE:
<221> NAME/KEY: misc_feature
<223> OTHER INFORMATION: prMD36.pGB.MCS.R.p

<400> SEQUENCE: 10
gcccggggat ccgcggccgc gtcgacctgc agccaagctt 40

<210> SEQ ID NO 11
<211> LENGTH: 34
<212> TYPE: DNA
<213> ORGANISM: Shigella sonnei
<220> FEATURE:
<221> NAME/KEY: misc_feature
<222> LOCATION: (6)..(11)
<223> OTHER INFORMATION: Restriction site: primer prMD58.tviD.F

<400> SEQUENCE: 11
gatcggctag cccgttcctc attgatttga ttgc 34

<210> SEQ ID NO 12
<211> LENGTH: 43
<212> TYPE: DNA
<213> ORGANISM: Shigella sonnei
<220> FEATURE:
<221> NAME/KEY: misc_feature
<222> LOCATION: (6)..(11)
<223> OTHER INFORMATION: Restriction site: primer prMD59.tviD.R

<400> SEQUENCE: 12

```
gatcgcccgg gttacgactt ccctgatgta ttttttgta atg                        43
```

<210> SEQ ID NO 13
<211> LENGTH: 42
<212> TYPE: DNA
<213> ORGANISM: Shigella sonnei
<220> FEATURE:
<221> NAME/KEY: misc_feature
<222> LOCATION: (6)..(11)
<223> OTHER INFORMATION: Restriction site: primer prMD60.vexA.F

<400> SEQUENCE: 13

```
gatcgctcga gtaattaatg ggcatcattt ttcagctatt tc                        42
```

<210> SEQ ID NO 14
<211> LENGTH: 34
<212> TYPE: DNA
<213> ORGANISM: Shigella sonnei
<220> FEATURE:
<221> NAME/KEY: misc_feature
<222> LOCATION: (6)..(11)
<223> OTHER INFORMATION: Restriction site: primer
      prMD83.vexA.R.xhoI.1000

<400> SEQUENCE: 14

```
gatcgctcga gttagaaaga attagtgccg cggg                                 34
```

<210> SEQ ID NO 15
<211> LENGTH: 60
<212> TYPE: DNA
<213> ORGANISM: Shigella sonnei
<220> FEATURE:
<221> NAME/KEY: misc_feature
<223> OTHER INFORMATION: prMD75.mcs.F.p

<400> SEQUENCE: 15

```
cggtctcgag gggcgcgccg gtaccgaatt ctaattaatg ggcatcattt ttcagctatt     60
```

<210> SEQ ID NO 16
<211> LENGTH: 58
<212> TYPE: DNA
<213> ORGANISM: Shigella sonnei
<220> FEATURE:
<221> NAME/KEY: misc_feature
<223> OTHER INFORMATION: prMD76.mcs.R.p

<400> SEQUENCE: 16

```
gtggatccaa gcttgcggcc gcccgtcgac agtaaagccc tcgctagatt ttaatgcg       58
```

<210> SEQ ID NO 17
<211> LENGTH: 22
<212> TYPE: DNA
<213> ORGANISM: Shigella sonnei
<220> FEATURE:
<221> NAME/KEY: misc_feature
<223> OTHER INFORMATION: prMD77.sites.remove.F.p

<400> SEQUENCE: 17

```
ccgacagtaa gacgggtaag cc                                              22
```

<210> SEQ ID NO 18
<211> LENGTH: 23
<212> TYPE: DNA
<213> ORGANISM: Shigella sonnei
<220> FEATURE:
<221> NAME/KEY: misc_feature
<223> OTHER INFORMATION: prMD78.sites.remove.R.p

<400> SEQUENCE: 18
ttagaaagaa ttagtgccgc ggg 23

<210> SEQ ID NO 19
<211> LENGTH: 34
<212> TYPE: DNA
<213> ORGANISM: Shigella sonnei
<220> FEATURE:
<221> NAME/KEY: misc_feature
<223> OTHER INFORMATION: prMD43.ss.F.HindIII

<400> SEQUENCE: 19
gatcaaagct tgatcaaata gctcatattc agcg 34

<210> SEQ ID NO 20
<211> LENGTH: 29
<212> TYPE: DNA
<213> ORGANISM: Shigella sonnei
<220> FEATURE:
<221> NAME/KEY: misc_feature
<223> OTHER INFORMATION: prMD44.ss.BamHI.R

<400> SEQUENCE: 20
gatcaggatc ctgctcagtc cggttggtg 29

<210> SEQ ID NO 21
<211> LENGTH: 33
<212> TYPE: DNA
<213> ORGANISM: Shigella sonnei
<220> FEATURE:
<221> NAME/KEY: misc_feature
<223> OTHER INFORMATION: prMD41.ss.F.BamHI

<400> SEQUENCE: 21
gtagcggatc caagcgcagc tatttaggat gag 33

<210> SEQ ID NO 22
<211> LENGTH: 36
<212> TYPE: DNA
<213> ORGANISM: Shigella sonnei
<220> FEATURE:
<221> NAME/KEY: misc_feature
<223> OTHER INFORMATION: prMD42.ss.R.XhoI

<400> SEQUENCE: 22
gatcgctcga gttaatttac ggggtgatta ccagac 36

<210> SEQ ID NO 23
<211> LENGTH: 17986
<212> TYPE: DNA
<213> ORGANISM: Shigella sonnei

<400> SEQUENCE: 23
ggtaatggct ccaacttatt gatagtgttt tatgttcaga taatgcccga tgactttgtc 60
atgcagctcc accgattttg agaacgacag cgacttccgt cccagccgtg ccaggtgctg 120
cctcagattc aggttatgcc gctcaattcg ctgcgtatat cgcttgctga ttacgtgcag 180
ctttcccttc aggcgggatt catacagcgg ccagccatcc gtcatccata tcaccacgtc 240
aaagggtgac agcaggctca taagacgccc cagcgtcgcc atagtgcgtt caccgaatac 300
gtgcgcaaca accgtcttcc ggagactgtc atacgcgtaa aacagccagc gctggcgcga 360
tttagccccg acatagcccc actgttcgtc catttccgcg cagacgatga cgtcactgcc 420
cggctgtatg cgcgaggtta ccgactgcgg cctgagtttt ttaagtgacg taaaatcgtg 480

-continued

```
ttgaggccaa cgcccataat gcgtgcagtt gcccggcatc caacgccatt catggccata    540
tcaatgattt tctggtgcgt accgggttgg gaagcggtgt aagtgaactg cagttgccat    600
gttttacggc agtgagagca gagatagcgc tgatgtccgg cagtgctttt gccgttacgc    660
accaccccgt cagtagctga acaggaggga cagctgatag aaacagaagc cactggagca    720
cctcaaaaac accatcatac actaaatcag taagttggca gcatcaccga ctacggggtt    780
agcagcagtg tatgccttta ccgcaaaaga gcagtggacg gctaaaacct atattcaagc    840
accacgtatt gctgaattag gcagctatct taaatttcac caagcgtatg cccgaatatt    900
aaatcaaccg ttagatacga atgcgttggc taatggattg ttttccgatt tgattttgat    960
tgctgaatcg ccagacacca aagttaaatt tctagagagt actgagtatt ataaaaagga   1020
aacaaataat ttatctactg accaagataa gaaaatttgg ttagctgagc aagcgaataa   1080
aggtcttgtg attacgccac caaaggaaaa gggaaataca agttactaca taatacaagc   1140
atcggcagac tcagcgcaag aggcatataa actactgcag ggatatctaa agaatgttaa   1200
taatcaagct gtaacattaa gtcttgatga gtttggtcaa aatgttaata ctcttttggt   1260
taatctaaat aaagaaatta ttgacataga tttccagaga aaatcagaaa agcttgatca   1320
aatagctcat attcagcgag atttaacaac tgcggaacaa gccggaatca ttgattatcg   1380
ctctagcaaa ggcggcttcg ataatgcgca aagtagctat aagttcttgc tcggcgaaaa   1440
actgttatca gcagagctaa aagcaactaa agatgcgcca attatttacc catttagata   1500
ttacgaagtg aaacgtcaaa ttgatgagtt agaaggaatg ttacgcgata acattcaggc   1560
gcaagcatat cgatatcaaa tgaagccatc tgagccagtt ataaaagaca aacccaacaa   1620
agcattaatt ttgattcttg gtgcattacc aggggcaatg tttgctatag ttggtacatt   1680
agtttatgcg acattaaaag ataaaaccaa gttagattaa actgggttac gtattgttgt   1740
gtcaatgcga aatagatgtt ctatgtgcac tttatgatgg ataagaaaat gaaattcgat   1800
actttgaatg cgaaaattgg gattataggc cttggttatg ttggattgcc tcttgctgtt   1860
gagtttggaa agaaagtaac gacgattgga tttgatatta ataagtctcg tattgatgaa   1920
ttacgaaatg gtcacgatag tacattagag tgctcaaatt tagagttgtt agaagcaact   1980
aaattgacgt acgcctgttc attagatgca ctaaaagagt gtaatgtatt tattgtaact   2040
gttccaactc caattgataa acataaacag ccagatctaa cacctctaat taaagcatct   2100
gaaacattgg gtaagataat aaagaaaggc gatgttatta tttatgagtc aacagtttac   2160
cctggagcga cagaagaaga ttgtatacca gttgtagaga aagtatcagg tcttaagttt   2220
aatattgatt tttttgccgg ttattcacct gagcgtatta atcctgggga taaagagcat   2280
cgtgtaacta atatccttaa ggtgaccagt ggatctacac cggatgttgc tgagtatgta   2340
gatcagctat ataaattaat aattactgtc ggtacgcata aagcatcatc gataaaagta   2400
gcagaggctg caaaagtaat tgaaaacacg cagcgagatg tcaatattgc attgattaat   2460
gagttatcta ttatatttaa taagttaggg attgatacct tagaggttct tgaggctgca   2520
ggtacgaagt ggaatttttt accttttagg cccggtttag taggtggcca ctgtataggt   2580
gtagatcctt attatcttac acataaagcg caaagtgtcg gctatcatcc ggagatgatt   2640
ttagccggac gtcgtttaaa tgatagtatg ggcagtatg tcgtttccca gttagtcaaa    2700
aaaatgttga aacaacggat tcaagttgaa ggggcgaatg tgttagtgat ggggcttaca   2760
tttaaagaga attgcccaga tctacgaaac actaaagtga ttgatattat ttcagagtta   2820
```

-continued

```
aaagaataca atatcaatat agatattata gatccatggt gttctaccga tgaggcacaa   2880
catgaatatg gattaacttt atgtgaagat cctaaagtta atcattatga tgcaataatt   2940
atcgctgttg cacacaatga gtttcgcgag atgggagaga gcgctattcg tgcattaggt   3000
aaagacgagc acgttttgtt cgatttaaaa tatgtgcttg ataaaaaaag tatcgatatg   3060
cgcttgtaag agtgattaaa aaaatcaaat cctctttgat atgatacacc tcagcatttt   3120
atgctaggtt tagcacttga ttaatataca tggatattta tatgtctcgc tatgaagaga   3180
ttacacagca gttaattttt tcaccgaaaa cttggttaat tactggtgtc gctggcttta   3240
taggatcaaa tcttttagaa aagttactta aattaaacca ggttgttatt gggttagata   3300
acttttccac gggacatcaa tataatcttg atgaagttaa aacattagtt tccactgaac   3360
agtggagtcg attttgcttt atagaaggtg atattcgaga tctcactacc tgtgagcaag   3420
ttatgaaagg tgttgatcat gtcttacatc aggctgcgct aggttctgta cctcgttcaa   3480
ttgttgatcc tataacaacc aatgcaacta atattactgg atttttgaat atcttacatg   3540
cggctaaaaa tgcacaagta caaagtttta cttatgctgc atcaagctca acttatggag   3600
atcatcccgc actaccaaaa gtagaggaaa acattggtaa tccactttct ccttatgcag   3660
ttactaaata tgttaacgag atttatgctc aggtatatgc tcgaacatat ggttttaaaa   3720
ctattggatt acgttatttt aatgtatttg gtcgtcgtca agatcctaat ggagcttatg   3780
ctgcagtaat tccaaaatgg acagcagcaa tgcttaaagg tgatgacgta tatattaatg   3840
gcgatggtga aacgagtcgt gatttttgtt atatagataa tgttatacaa atgaatatat   3900
tatctgcatt agcgaaggac agtgctaaag ataatatata taatgttgca gttggtgata   3960
gaacaacgtt aaatgaatta tctggttaca tttatgatga gcttaattta attcaccata   4020
tcgataaatt gagcattaag tatagagagt ttagatctgg agatgttagg cattctcagg   4080
ctgatgttac taaggctata gatttactaa agtatagacc aaatataaaa atcagagagg   4140
gattacgact ttcaatgccg tggtatgtga gatttttaaa aggctaaatt atattaacat   4200
gaataaataa tctatttcac ctctgttatt aatgcagggg tgaaaatcca tgtatttatt   4260
ctaaatggtc agtgtatgtt tagaaaaatg attgatgcag gtggtacatt tttacttaaa   4320
gcaatatttc aaataggagt ttttgtttat ttcacacatg tgtcagatat tactacattt   4380
ggtattatta gttatgtgtt tactgtttat tggtttgtgc ttaacttctc tgattatgga   4440
tttagaacaa aattagtgaa agatatttct gataatagtt attctgcatc agaattatta   4500
tcaagaagtg atggagttaa aacatatgtt tttttcttca tttttataat cttcatgttt   4560
tattcttatg tttctgattc aatttcatta actctgcttg tttatatttc atctgcatat   4620
tttgtttgta tttcaagtgg tagatttagc ttgctacagg ctgttggtcg gtttagatgt   4680
gaattatata taaatatcta ctcaacaatt atatatattg ggtgtaattt atttttatct   4740
ctgtttatcg aacctctata ttatagtgcg atatcaatat tcatatactc aatttcgctt   4800
ttggttttct catcacataa atgcaatgtg ccatgttttc atataaaaag accaagtatt   4860
ttagtttata aagatttttt ggatgcaact ccgttcgcta ttctggtgtt actaaatgtt   4920
gttttatcta gtattgacct ttttatatta aaagaatatt tctcttataa tagtgttgct   4980
atatatcagg tggtaactag ggttaatacc ggtctaataa tagtgtttaa tgttatttat   5040
actgttttat tgccttcatt ttcttattat ctgaaaaatt ctgaatgggg taatataagg   5100
aaattacaac gatatatatc actgttagtc ttattactat gtttatgcta ttattttttt   5160
ggcatctatt tcgtagggat attgtttggt gatgagtata aggtaatatc ttctgcaaca   5220
```

tttttgataa tgtttatggc tcttattaaa tataattttt ggctaataaa tgaactttat 5280
cttgtgtgta gtggaaatca aagcgagcga gttaaatcgt attgtattgg tgtggtcatt 5340
tcaatggcgg ttttctttta ttttatacct cggtatggat ggagtggggc ggtttttgga 5400
agtgccattg caacattagt aattggaata ttttatatta tttctgtgaa aaaagattgt 5460
gggaaaattc ttcatgataa gtattcacta atgatgatct ttgtcccaat tttcttttat 5520
tttattatta atggtcagca gcggttgtta tattaatatg ttgtggtttt atatcgttcc 5580
attaatatgt ttagactcga ttggaagcct aataaaggtt aagtatgtta atatacctat 5640
atcctgtact tttgttattt aatatccttc cggttttttt ttatggacaa atgaactctg 5700
atttagagcg tttttttgga gttcctattg gctatattcc agatctaata ttttatttct 5760
ttgttgtttt aacatctata ataacgttga ggtttcacgt ttctctgtgg acaaagaaat 5820
tattattttt aggcatcata ttcctgattt atatcagcat tcagatgttg ttgttatcag 5880
cggatatatc aggtgtcgta attttattat cgtttttttc taattttata gctttggttc 5940
ttttggtgtc attttgcatt ggtaaagatg agctttattt aactcattcg gttagaaata 6000
taaatgttgt aatgtgtttt ggtattatct gtggagttgt aaaattattt attggttatt 6060
ctgaagatag taattttata gtttatttaa atagaaatgc caccgcaatt atagtagtgt 6120
gcttttattg tgtatattca tacttttatc gtggtcgaaa gtcttggtat gtctcatctg 6180
tattgtactc tctgttcttt ctttttctgg atagccgagc aggaataata tcatttgcta 6240
tatcgttgtt ttttgttttt cttcagttaa caaagaagga aaagttatta atatcattgt 6300
tttttgttcc tcttctaact ttaggtattt cttttactga tataggcact cgtcttgaac 6360
gaatgctgtc ttcgtcacag gttatattct ctggtggtaa cactcttaca aaaagtcaga 6420
atgattatcg tcgagttgag ttagtattta ttggggttga tgttttaaaa gaaaattatt 6480
taattggcac tggattaggt gttgcaaatt atgtaaaggc tatagataaa aagtttttag 6540
gaagtaccaa ctttgggttg gcgcataatt tttatttatc ttattcggct cagttaggga 6600
ttattggttt tattttgctt atttctgtat tttatataat gctgtctcca atttttaaat 6660
gcggagggta tattggtaaa ggatgcgttt ttgctttggc tttctatgtc ttttttaatg 6720
agtatatatt gacgccagcg atatatattt atatttctat ttttttatcg gtggttttta 6780
tacgtaattc taaatagctg cgcggaatag tagatcactt tgagggaact tagcccggat 6840
tgtgcgatct gatcaatcgc caaatcaaaa caaatcacca accggactga gcaatgccga 6900
tcatagcacc aatttcccgt gacgaacgac gcctgatgca gaaagccatc cataaaacac 6960
acgataaaaa ttatgcccgc agactgactg ccatgctgat gctgcaccgg ggcgaccgtg 7020
tcagcgacgt tgccagaacg ctctgctgcg cccgttcctc tgttggacgc tggattaact 7080
ggttcacgca gtcgggtgtt gagggactga aatcattacc tgccgggcgt gcccgtcgct 7140
ggccgtttga gcatatctgc acactgttac gtgagctggt aaaacattct cccggcgact 7200
ttggctacca gcgttcacgc tggagtacag aactgctggc aataaaaatc aatgagataa 7260
ccggttgcca gttaaatgcc ggaaccgttc gccgctggtt gccgtctgcg gggattgtgt 7320
ggcgaagggc tgcgccaact ctgcgtatcc gtgacccgca taaagatgaa aagatggcag 7380
caatccataa agcactggac gaatgcagcg cagagcatcc ggtcttttat gaagatgaag 7440
tggatatcca tcttaatccc aaaatcggtg cggactggca actgcgcgga cagcaaaaac 7500
gggtggtcac gccgggacag aatgaaaaat attatctggc cggagcgctg cacagcggga 7560

-continued

```
caggtaaagt cagctgtgtg ggcggcaaca gcaaaagttc ggcgctgttc atcagcctgc   7620
tgaagcggct taaagcgaca taccgtcggg cgaaaaccat cacgctgatc gtggacaact   7680
acattatcca caaaagccgg gaaacacaga gctggctgaa ggagaacccg aagttcaggg   7740
tcatttatca gccggtttac tcgccatgga tgaatcatgt tgaacggcta tggcaggcac   7800
ttcacgacac aataacgcgt aatcatcagt gcagctcaat gtggcaactg ttgaaaaaag   7860
ttcgccattt tatggaaacc gtcagcccat tccccggagg caaacatggg ctggcaaaag   7920
tgtagcggta ttaagcgcag ctatttagga tgagaatatg ttgttagaat atgttgaaag   7980
aaaaatttcc ttagccttga gtaagtatcc taaggtaagg gatgttatta agttctttta   8040
tttatatatc gcatcattat tcggaattat tttgaataaa aataagacgg ttattcaatc   8100
aaaaatatac gagatttcaa ttgatgattc tgaagaatca ttttttggct attatgacca   8160
tagtccaatg agctctaatg ggcggtacgt attgttccac tctagtgcgt ttagcactaa   8220
acgacatcca aagaaagtta agtatatatc tatttgcgta aaagaccttc ttaataacaa   8280
agtttataag ctatatgata cgcgagcatt taattggcag cagggaagcc gattaatgtg   8340
gattgatgat gacaatataa tttttaatga ctatgaaaat aatggataca ttagtgttgt   8400
ctattctttg tctttgatga aggttataaa aaaaataaac tatccgattt atgatgtgaa   8460
taattacaag gctgtgacgt tagatttctc atggctggct aaatatgata gcgattatgg   8520
ttattataat aaaaaatcat tttctacaga tatttcaatc attaatttga atacgggggg   8580
aatagaatta tttttatcct tagacgaaat gctaaagaga actaatttta aatgtaatat   8640
tgatgttgaa catgtggtca atcattttat gtttgctccc gatggacgtt ccgttatgtt   8700
catacatcga tactatacac ctaaaggaaa gcgtgaaagg ttaatacatt ggaatttaat   8760
aaatgataat gttcgagtcc taataaatga atcgattatt agtcattgtt gttggaatgg   8820
gaatgatgaa attataggtt tttttggtgc agaaatagat tcgctaaatt attatagatt   8880
gtcaattgaa tcctgtaata cagagaaatt gtttttttgat gcaagaaaat attctgatgg   8940
acatcctact atagttcata atagatatat tatatctgat acttacccag ataaaaatag   9000
aattaaaaag ttgtttgttt atgaccttgt caaaaatgat tatcgcgagc ttggattatt   9060
ttatgagtca atgagttttt tttcttattc tcgatgtgac ttacatccaa ggatctcggt   9120
tgataataga tttttgtttg ttgattcagt tcactcaggg aaaagaaaac tatattttat   9180
gaggagtggt atttgtgagt gatgttctag tatctttaat tatagtttgc tttaatgcag   9240
agaagtatat tgaaaaatct cttttggcat ttattaatca agatgttgga ttagataaat   9300
ttgaattgat tattgtagat ggggattcat ctgataatac aatatctatt gttcaggatg   9360
ttttttctaa acatagcaac attaagcata aaattatcaa taataaaaaa agaactcttg   9420
ctacgggttg gaatattggg gtgctagaag ctaatggtaa gtttgtgtgt agagttgatg   9480
cacatagtga tattccaaat aactatatat ctaaattatt agatgattat tttaatatta   9540
tgcagtttga tgatagcgtt gttggtgttg gaggtgtatt aactaattct tataaaacta   9600
agtttggttc aattgtagcg gatttttatg catcgaaatt tggtgttggt aattctccat   9660
ttaggtgcgt agacaaaaat aatcgactaa aaaaaacaga tacagctgtc tttgctttat   9720
ataataaaga tgtgtttttt gatgttggac tttttaatga agtattagat agaaatcaag   9780
atattgattt tcataagaga gttttaagca ataatttgtc attatataca gataatagtt   9840
tatttgttga gtattatgtt agagataatt ttaaagattt cataaagaaa ggttttcttg   9900
atggtttttg ggttgttatg tctggagcat attattttag acatatagtg ccactttttt   9960
```

```
ttgttttgta tttaattgta tctttttctc ttttctttgc tactggtgat tatatatatt  10020
tatctttttt attttttat tttcttattt ctattttgtt ttcaattcga gatgggcgaa  10080
gttttatagg tagagtattt cttcctttta tatttttgtc ttatcatatt tcttatggat  10140
gtggatcgtt attatctttt ttgaaaaggt attttaaatg aaaaatttta ttccttttgc  10200
gttacctgaa attggcgaag aagaaattgc agaggtaatt gactctttac gttcaggttg  10260
gattacgaca ggtcctaagg ctaagcaatt tgaacaagaa ttttctaatt acctaggagc  10320
gaacgttcaa tcattagctg ttaactctgc tacgtcgggc ttacatttgg ctcttgaagc  10380
tgttggcgta aagccgggag accaagttat tgtcccatca tatacattca ctgctactgc  10440
cgaaattgtc aggtaccttg gtgctgatcc tgtaattgtt gatgtagatc gtaaaacatt  10500
taatatatca gttgatgcca ttgagaaggc tattactaat gaaacaaagg cgattattcc  10560
agtacacttc gctggattag cttgtgacat ggattcaatc ttatcaattg ctaaaaaata  10620
tgacctaaag gttgtcgagg atgccgctca tgcatttcct acaacatata aaggaagtaa  10680
gataggaacg cttgattcag atgctacggt ttttagcttc tacgccaata aaactatgac  10740
aaccggtgaa ggcggaatgg ttgtttcaaa aaataaagat ataattgagc gttgtaaggt  10800
aatgcgttta catggaatca gtcgtgacgc ttttgaccgg taccagtcta aaactccttc  10860
ttggttttat gaggttgtag ctccagggtt taaatacaat atgcctgata tctgtgcggc  10920
aatcggtatt catcaactta gaaagatcga tgattttcag aaaaaacgtc aacgaatggc  10980
aaaaatttac gatgatgcgt taaaagaatt gccacttgaa ttgcctgaat ggcctactaa  11040
tgctagtgat attcatgctt ggcatctata tcctatccgc ttaaaaactg attcggctat  11100
taatcgcgat gattttatta agaagttatc agatcttgga attggttgtt ctgtccattt  11160
tataccgttg cataagcaac cggtttggcg tgatacatat aatttgaacg ccagtgactt  11220
tccagtttct gaggagtgtt atttaaatga aatatctatt cctctttata ctaaaatgac  11280
ggatcaagat cagttgttcg ttatcaaatc gattagacaa ttatttatgt aatggtattt  11340
tatattaaat gaaacgtatt tttgatgtta tcgtggcagg cttaggcctg ctttttctat  11400
ttcctgtttt tatcattgtg tcaatgttaa ttgttgctga ttctaaaggg ggggtttttt  11460
ttaggcagta tagagttggg agatttggga aagattttag gatacataaa tttagaacga  11520
tgtttatcga ttcagaaaaa aaaggacgga taacagttgg tcaagatgct cgggtaacca  11580
gagttggatg gtatttacgg aagtacaaaa tcgatgagct tcctcaattg atagatgttc  11640
tttctggaac aatgagtttg gttggcccaa gaccggaagt gagggagttt attgatgagt  11700
atcctgatga tataagggaa aaagttttat cggttaggcc agggataact gacttagcat  11760
ctatagaaat ggtagatgaa aatgagattt tgtctagtta tgatgaccca cgtagggctt  11820
atatagatat aattcttcca atcaagcaaa gatattattt agattatgtt gctaacaatt  11880
cagtaaagta tgattgtgtg ataatttgga aaactattat taagattttg tcgcgataat  11940
aaggtagtgt aggatgattg atagaatatt ggagctgcca agaattgtta agagaggtat  12000
catcatctgc attgatgtag ttatggtgat attctcattt tggttgtctt attggttgag  12060
gcttgatgag caaacggctt ttcttagtgc accgatgtgg tttgctgcag ctattcttac  12120
catatttacc gtgtttatat ttatcaggat tgggctttat cgggcagtct tacggtatgt  12180
tagtgcaaag ataatgttgc taataccagt tggtattctg gcctcaacgt tatctcttgt  12240
cgttatatca tattcgctat ccataatgtt gccgcgcact gttgtcggaa tttatttttt  12300
```

```
ggttttactt ttactgacat caggctctag attgcttttt agaatgatac ttaactatgg  12360
agttaagggt agtgcgcctg ttttgattta tggcgctggt gaatctggcc gacaattatt  12420
gccagcatta atgcaggcaa aagaatattt tcctgtggca tttgtggatg ataatcctcg  12480
cttgcataag gctgtcattc atggtgtaac agtttatccc tcggataaac tgagttacct  12540
tgtagatcgc tatggtataa agaaaattct tttggcgatg ccgagcgtca gtaagtcaca  12600
aaggcagaaa gtgattactc gtttagagca tctaccgtgt gaagttctct ctattccggg  12660
tatggtcgat ttagtcgaag gtcgagcaca aatcagtaat ctaaaaaaag tatcgattga  12720
tgacttacta ggtcgtgatc cggttgctcc tgatgccaaa ttgatggccg aaaacattac  12780
tggcaaagcc gttatggtca ctggggcggg aggctcgatc ggctctgagc tttgtcgtca  12840
aattgttcga tataagccgg ccaaattggt tctatttgaa ctgtctgaat atgccctcta  12900
cgctattgag aaagagctct cggcgctgtg cgacaaagaa gttttgaatg ttccagtgat  12960
ccctctgttg ggctcggtgc agcgtcagaa tcgcttacag atggtgatga agtcctttgg  13020
tattcaaacg gtttatcatg cggccgctta taaacatgtg cctctggttg agcataatgt  13080
ggtggaaggg gtacgtaata acgtgtttgg taccttgtac tgcgctgagt cagcgatcga  13140
aagtggcgtt gaaacttttg tgttgatttc caccgataaa gcggtgcgcc cgaccaacac  13200
tatggggaca actaagcgtc tggccgaatt ggtattgcag gctttgtctg cacggcaaag  13260
ccaaactcgc ttttgtatgg tgcgatttgg taatgtactc ggttcttcgg gctctgtcgt  13320
gccgttgttt gaaaaacaga ttgcccaagg tgggccagtt accttgactc atcgtgacat  13380
tattcgctat ttcatgacaa ttccggaagc atcacagttg gtgattcaag cgggggcgat  13440
ggggcatggc ggcgatgtct ttgtcttaga catgggcgat ccggtcaaga tttatgactt  13500
agccaaacgc atgatccggt taagtggctt gagtgtacgg gatgataaaa atccagatgg  13560
cgatattgcc attgaagtta cgggattacg tccaggggag aaactgtatg aagaattact  13620
gattggtgat tcagttcaag gtacctctca tccacgaatt atgacggcca acgaagtgat  13680
gctaccgtgg caggatctat cgctcttact taaagagctg gatcaagctt gtcatgactt  13740
tgatcatgag cgaattcgca gtttgttgtt acaagcacca gcggcattca atccaactga  13800
tgatatttgc gatctagttt ggcagcagaa aaaatcgctg ttatcacaag cgagcaatgt  13860
cattcgcctg tgattgctta ggtttaacct tccacaccaa ttcttcacct ctcttacaaa  13920
tccccgctag gcggtacatc gtgaccgcct ttagcctgat gcctgctctt taacaaacag  13980
gacatcagtg tatgtttaaa ccttttagcg ccgaattttt cggcactttc tggctggttc  14040
tgggtggctg tggtagcgcc ttgatctctg ctgctttccc acagttaggt ataggctttt  14100
tgggcgtggc gttggcgttt ggtctgacag tagtcaccat ggcttatgcg gtcgggcaca  14160
tctctggtgc gcattttaac cccgcggtga ccttgggtct gtgggccggt ggacgcttcc  14220
cagcagcgcg cgtgttacct tacattatcg ctcaggttat cggcggtatt gccgctgcgg  14280
cagtgctgta tggtatcgcc agcggtaagg ctgggtttga tgcgacaacc agcggttttg  14340
cggctaatgg ttatggcctc cattcacctg gcggctatgc gttaagcgcc tgtatgctga  14400
gcgagtttgt cctcagtgcg ttttttgtcc ggagcgacag aaaaacgcgc tcctgcgggc  14460
tttgcgccac tggcgattgg tctggtaatc accccgtaaa ttaaccagcg tcaaaagtag  14520
aattttctcg taccataaac gcaggagatt ctttatgcaa acatcaaaat ttaccgacaa  14580
gcaaatcatg gcgatcctca aatgaacccc cccgggaatc ctggagacta aacttcctga  14640
gaaagaggta aacaggatga ctaaaaatac tcgtttttcc cccgaagtcc gtcaacgggc  14700
```

agtccgtatg gttctggaaa gtcagggcga atatgactca caatgggcga caatttgttc 14760
cattgctcca aagattggct gtacgccgga gactctgcgt gtccgggttc gccagtatga 14820
gcgggatacc gggggcggtg atggagggct caccaccgct gaacgtcagc gtctgaaaga 14880
gctggagcgt gaaaatcgtg aactgcgccg cagtaacgat atccttcgcc aagcttccgc 14940
ttattttgcg aaggcggagt tcgaccgcct ctggaaaaaa tgatgccact gctggataag 15000
ctgcgtgagc agtacggggt cggaccgcta tgcagcgaac tgcatattgc cccgtcaacg 15060
tattagggat ttgaagccca accgtacgaa aacgtacgct aagttcattt cttgaacaac 15120
ctggctgact ctatgtattt gtacagcgtt ggcctcgata tccccatcaa cacacaaatc 15180
tgcgcaactg tatgtttttt ctcgttatag agttgaacag caagggcctg tttatcctta 15240
ctcagtgttt tcggcctgcc gcccttacgt cctctggctc gtgctgcttg aagcccgacc 15300
tgagttctct ctcttgtcag gttgcgttca tcgataggaa ttaaaacccc aaaaagatta 15360
aaaaaacacc acaaaacgga tgtttcttca acaccacttt tgctccatat gaacggaacc 15420
gacgattaaa ctggatggct ctgattgatt cagggtatga atggcggttt tttgctccgt 15480
ttccctcaaa atggacgcaa cttcccctct gcggctctca gccgcaccac cgcatccggg 15540
ccaagcagct catgcatcag gacctgctct gccagacggt agccccgctt cagccccgta 15600
aaacgcatct gactcccgca cagcacgcac ttcagcgggt caaccttcag taacctctga 15660
tacatccctc tccaggtgat ttgcatcgcc gtttttctca ctgtctccgt tatgatgtac 15720
accacttctt ccagtaaccg ccgtttcgcc ggactcaaaa aaccgtagta cctcaccata 15780
cggaacccct tatccgccac atgccaggag aacctttcca tgaactcatc tccactcatc 15840
aacaggtatt cttcccgttt tgttcggtga ctgttgtaac gcagaccgat ttcatcctga 15900
ccggcataat gctccagacg actcatcggc actggtggct ttttcaggta agagccaaag 15960
tacaccgcca catgggtggc attatccatc acccgggata cgttgacatt ccagccacgg 16020
cggtaatgcg tgtccaggaa gcgattccat tcccgtttac tgcttccttc tgctgccagc 16080
gcatccggca tcaccaggtc agggtatttc cgtgacagca accgtgttat ccggtagcgc 16140
cacatgctca tcaccttacg ggcgtaaaaa tgaagatttt tccaggtgtg gcccgacgtc 16200
acaccaccgg cagttgtcga taaatggata tgcggatgcc actgctggtc acgcccccat 16260
gtgtggatca ccgtgaatat ccccgactcc acatctgcct gatggcagat ttccagtatc 16320
acatccgctg caatgcggct catctctgtc agtaaccacc ggttgtggaa caccagggac 16380
cagtactggc agggaagtgt gaacacaata tgctgccacg ggcagtcggg gaccaggctc 16440
agcagatact gtatccactg tgcgccagcc ttcaccccgc agtgcgggca ggagcggctt 16500
ttacaccgga agcagacctt ttttgtatgg caacagtccg gtgatgaaca gcaccactgt 16560 gtataccccca tcagtgtggt cccgcacgcc atgattttgg tcaccgactc aatcaccacc 16620
ggacgtactg ccccttccgg ctgcttctcc agccagttaa gccagcggtt tccctgctga 16680
aagatatcgg caaaacgggg aagcatcaga agggcggggc gactccgtcc ggccagtgaa 16740
ccgtgccaca ctccgggcag tacataccgc cggcgctgat accggaaaga atggtcgcaa 16800
attcccgctc cgtgcagcgg gcgatttccg gataccccttc gtcatcaaca cgtacaaacc 16860
agaagaccag ctttttgttt cccgcatcca caaagaacgg aatattcagg tctgcgcagc 16920
attcaacggc atcgtcaaaa ctatcaaagc gcagaacttc tgcgtcttct tcgtcaaaaa 16980
aatcatcttc gtgaagcttc acgacatagc ggggaagttt gcttctttga gaggcgggtt 17040
tacgtttacg gggtttagct gaacgggcca tataaccacc acctgaaaga caatgacatt 17100
gcctgttttt ataacggtaa ttgcagacca tgacaagccg cagccgtcag gctgcctact 17160
cgggggttca tcgcagcagc tacagatact ggaaaaaccg tcctgaaaaa ccagacggca 17220
gacgggctgt attacgcagt caggtacttg agctacatgg catcagccac ggttcggccg 17280
gagcaagaag catcgccaca atggcaaccc ggagaggcta ccagatggga cgctggcttg 17340
ctggcaggct catgaaagag ctggggctgg tcagctgtca gcagccgact caccggtata 17400
aacgtggtgg tcatgaacat gttgctatcc ctaactacct tgaaaggcag ttcgccgtga 17460
ccgagccaaa tcaggtgtgg tgcggtgatg tgacctatat ctggacgggt aagcgctggg 17520
cgtacctcgc cgttgttctc gacctgttcg caagaaaacc agtgggctgg gccatgtcgt 17580
tctcgccgga cagcaggctc accatgaaag cgctggaaat ggcatgggaa acccgtggta 17640
agcccggcgg ggtgatgttc cacagcgatc agggcagtca ttatacgagc aggcagttcc 17700
ggcagttatt gtggcgatac cagatcagac agagtatgag ccggcgcgga aactgctggg 17760
ataacagccc aatggaacgc ttcttcagga gtctgaagaa cgaatggatg ccgatggtgg 17820
gttacgtaag cttcagagag gcagctcacg ccataacgga ctatatcgtt ggatattaca 17880
gcgcactaag accgcacgaa tataacggtg ggttaccccc aaacgaatcg gaaaatcgat 17940
actggaaaaa ctctaactcg gtggccagtt tttgttgacc acttca 17986

<210> SEQ ID NO 24
<211> LENGTH: 18282
<212> TYPE: DNA
<213> ORGANISM: Shigella sonnei
<220> FEATURE:
<221> NAME/KEY: misc_feature
<223> OTHER INFORMATION: Sequence of pMD-TV-Ss-1 plasmid (Manuscript
Table 1 and Figure 1 B-C) 18,282 bp

<400> SEQUENCE: 24
aagcttgatc aaatagctca tattcagcga gatttaacaa ctgcggaaca agccggaatc 60
attgattatc gctctagcaa aggcggcttc gataatgcgc aaagtagcta taagttcttg 120
ctcggcgaaa aactgttatc agcagagcta aaagcaacta aagatgcgcc aattatttac 180
ccatttagat attacgaagt gaaacgtcaa attgatgagt tagaaggaat gttacgcgat 240
aacattcagg cgcaagcata tcgatatcaa atgaagccat ctgagccagt tataaaagac 300
aaacccaaca aagcattaat tttgattctt ggtgcattac caggggcaat gtttgctata 360
gttggtacat tagtttatgc gacattaaaa gataaaacca agttagatta aactgggtta 420
cgtattgttg tgtcaatgcg aaatagatgt tctatgtgca ctttatgatg gataagaaaa 480
tgaaattcga tactttgaat gcgaaaattg ggattatagg ccttggttat gttggattgc 540
ctcttgctgt tgagtttgga aagaaagtaa cgacgattgg atttgatatt aataagtctc 600
gtattgatga attacgaaat ggtcacgata gtacattaga gtgctcaaat ttagagttgt 660
tagaagcaac taaattgacg tacgcctgtt cattagatgc actaaaagag tgtaatgtat 720
ttattgtaac tgttccaact ccaattgata aacataaaca gccagatcta acacctctaa 780
ttaaagcatc tgaaacattg ggtaagataa taaagaaagg cgatgttatt atttatgagt 840
caacagttta ccctggagcg acagaagaag attgtatacc agttgtagag aaagtatcag 900
gtcttaagtt taatattgat ttttttgccg gttattcacc tgagcgtatt aatcctgggg 960
ataaagagca tcgtgtaact aatatcctta aggtgaccag tggatctaca ccggatgttg 1020
ctgagtatgt agatcagcta tataaattaa taattactgt cggtacgcat aaagcatcat 1080

```
cgataaaagt agcagaggct gcaaaagtaa ttgaaaacac gcagcgagat gtcaatattg   1140
cattgattaa tgagttatct attatattta ataagttagg gattgatacc ttagaggttc   1200
ttgaggctgc aggtacgaag tggaattttt tacctttttag gcccggttta gtaggtggcc  1260
actgtatagg tgtagatcct tattatctta cacataaagc gcaaagtgtc ggctatcatc   1320
cggagatgat tttagccgga cgtcgtttaa atgatagtat ggggcagtat gtcgtttccc   1380
agttagtcaa aaaaatgttg aaacaacgga ttcaagttga aggggcgaat gtgttagtga   1440
tggggcttac atttaaagag aattgcccag atctacgaaa cactaaagtg attgatatta   1500
tttcagagtt aaaagaatac aatatcaata tagatattat agatccatgg tgttctaccg   1560
atgaggcaca acatgaatat ggattaactt tatgtgaaga tcctaaagtt aatcattatg   1620
atgcaataat tatcgctgtt gcacacaatg agtttcgcga gatgggagag agcgctattc   1680
gtgcattagg taaagacgag cacgttttgt tcgatttaaa atatgtgctt gataaaaaaa   1740
gtatcgatat gcgcttgtaa gagtgattaa aaaaatcaaa tcctctttga tatgatacac   1800
ctcagcattt tatgctaggt ttagcacttg attaatatac atggatattt atatgtctcg   1860
ctatgaagag attacacagc agttaatttt ttcaccgaaa acttggttaa ttactggtgt   1920
cgctggcttt ataggatcaa atcttttaga aaagttactt aaattaaacc aggttgttat   1980
tgggttagat aacttttcca cgggacatca atataatctt gatgaagtta aaacattagt   2040
ttccactgaa cagtggagtc gattttgctt tatagaaggt gatattcgag atctcactac   2100
ctgtgagcaa gttatgaaag gtgttgatca tgtcttacat caggctgcgc taggttctgt   2160
acctcgttca attgttgatc ctataacaac caatgcaact aatattactg gatttttgaa   2220
tatcttacat gcggctaaaa atgcacaagt acaaagtttt acttatgctg catcaagctc   2280
aacttatgga gatcatcccg cactaccaaa agtagaggaa aacattggta atccactttc   2340
tccttatgca gttactaaat atgttaacga gatttatgct caggtatatg ctcgaacata   2400
tggttttaaa actattggat tacgttattt taatgtattt ggtcgtcgtc aagatcctaa   2460
tggagcttat gctgcagtaa ttccaaaatg gacagcagca atgcttaaag gtgatgacgt   2520
atatattaat ggcgatggtg aaacgagtcg tgatttttgt tatatagata atgttataca   2580
aatgaatata ttatctgcat tagcgaagga cagtgctaaa gataatatat ataatgttgc   2640
agttggtgat agaacaacgt taaatgaatt atctggttac atttatgatg agcttaattt   2700
aattcaccat atcgataaat tgagcattaa gtatagagag tttagatctg gagatgttag   2760
gcattctcag gctgatgtta ctaaggctat agatttacta aagtatagac caaatataaa   2820
aatcagagag ggattacgac tttcaatgcc gtggtatgtg agatttttaa aaggctaaat   2880
tatattaaca tgaataaata atctatttca cctctgttat taatgcaggg gtgaaaatcc   2940
atgtatttat tctaaatggt cagtgtatgt ttagaaaaat gattgatgca ggtggtacat   2000
ttttacttaa agcaatattt caaataggag tttttgttta tttcacacat gtgtcagata   3060
ttactacatt tggtattatt agttatgtgt ttactgttta ttggtttgtg cttaacttct   3120
ctgattatgg atttagaaca aaattagtga aagatatttc tgataatagt tattctgcat   3180
cagaattatt atcaagaagt gatggagtta aaacatatgt ttttttcttc atttttataa   3240
tcttcatgtt ttattcttat gtttctgatt caatttcatt aactctgctt gtttatattt   3300
catctgcata ttttgtttgt atttcaagtg gtagatttag cttgctacag gctgttggtc   3360
ggtttagatg tgaattatat ataaatatct actcaacaat tatatatatt gggtgtaatt   3420
```

-continued

```
tatttttatc tctgtttatc gaacctctat attatagtgc gatatcaata ttcatatact   3480
caatttcgct tttggttttc tcatcacata aatgcaatgt gccatgtttt catataaaaa   3540
gaccaagtat tttagtttat aaagattttt tggatgcaac tccgttcgct attctggtgt   3600
tactaaatgt tgttttatct agtattgacc tttttatatt aaaagaatat ttctcttata   3660
atagtgttgc tatatatcag gtggtaacta gggttaatac cggtctaata atagtgttta   3720
atgttattta tactgtttta ttgccttcat tttcttatta tctgaaaaat tctgaatggg   3780
gtaatataag gaaattacaa cgatatatat cactgttagt cttattacta tgtttatgct   3840
attatttttt tggcatctat ttcgtaggga tattgtttgg tgatgagtat aaggtaatat   3900
cttctgcaac atttttgata atgtttatgg ctcttattaa atataatttt tggctaataa   3960
atgaacttta tcttgtgtgt agtggaaatc aaagcgagcg agttaaatcg tattgtattg   4020
gtgtggtcat ttcaatggcg gttttctttt attttatacc tcggtatgga tggagtgggg   4080
cggtttttgg aagtgccatt gcaacattag taattggaat attttatatt atttctgtga   4140
aaaaagattg tgggaaaatt cttcatgata agtattcact aatgatgatc tttgtcccaa   4200
ttttctttta ttttattatt aatggtcagc agcggttgtt atattaatat gttgtggttt   4260
tatatcgttc cattaatatg tttagactcg attggaagcc taataaaggt taagtatgtt   4320
aatataccta tatcctgtac ttttgttatt taatatcctt ccggtttttt tttatggaca   4380
aatgaactct gatttagagc gttttttggg agttcctatt ggctatattc cagatctaat   4440
attttatttc tttgttgttt taacatctat aataacgttg aggtttcacg tttctctgtg   4500
gacaaagaaa ttattatttt taggcatcat attcctgatt tatatcagca ttcagatgtt   4560
gttgttatca gcggatatat caggtgtcgt aattttatta tcgttttttt ctaattttat   4620
agctttggtt cttttggtgt cattttgcat tggtaaagat gagctttatt taactcattc   4680
ggttagaaat ataaatgttg taatgtgttt tggtattatc tgtggagttg taaaattatt   4740
tattggttat tctgaagata gtaattttat agtttattta aatagaaatg ccaccgcaat   4800
tatagtagtg tgcttttatt gtgtatattc atacttttat cgtggtcgaa agtcttggta   4860
tgtctcatct gtattgtact ctctgttctt tctttttctg gatagccgag caggaataat   4920
atcatttgct atatcgttgt tttttgtttt tcttcagtta acaaagaagg aaaagttatt   4980
aatatcattg ttttttgttc ctcttctaac tttaggtatt tcttttactg atataggcac   5040
tcgtcttgaa cgaatgctgt cttcgtcaca ggttatattc tctggtggta acactcttac   5100
aaaaagtcag aatgattatc gtcgagttga gttagtattt attggggttg atgttttaaa   5160
agaaaattat ttaattggca ctggattagg tgttgcaaat tatgtaaagg ctatagataa   5220
aaagttttta ggaagtacca actttgggtt ggcgcataat ttttatttat cttattcggc   5280
tcagttaggg attattggtt ttattttgct tatttctgta ttttatataa tgctgtctcc   5340
aatttttaaa tgcggagggt atattggtaa aggatgcgtt tttgctttgg ctttctatgt   5400
ctttttttaat gagtatatat tgacgccagc gatatatatt tatatttcta ttttttttatc   5460
ggtggttttt atacgtaatt ctaaatagct gcgcggaata gtagatcact ttgagggaac   5520
ttagcccgga ttgtgcgatc tgatcaatcg ccaaatcaaa acaaatcacc aaccggactg   5580
agcaggatcc aagcgcagct atttaggatg agaatatgtt gttagaatat gttgaaagaa   5640
aaatttcctt agccttgagt aagtatccta aggtaaggga tgttattaag ttcttttatt   5700
tatatatcgc atcattattc ggaattattt tgaataaaaa taagacggtt attcaatcaa   5760
aaatatacga gatttcaatt gatgattctg aagaatcatt ttttggctat tatgaccata   5820
```

```
gtccaatgag ctctaatggg cggtacgtat tgttccactc tagtgcgttt agcactaaac   5880
gacatccaaa gaaagttaag tatatatcta tttgcgtaaa agaccttctt aataacaaag   5940
tttataagct atatgatacg cgagcattta attggcagca gggaagccga ttaatgtgga   6000
ttgatgatga caatataatt tttaatgact atgaaaataa tggatacatt agtgttgtct   6060
attctttgtc tttgatgaag gttataaaaa aaataaacta tccgatttat gatgtgaata   6120
attacaaggc tgtgacgtta gatttctcat ggctggctaa atatgatagc gattatggtt   6180
attataataa aaaatcattt tctacagata tttcaatcat taatttgaat acggggggaa   6240
tagaattatt tttatcctta gacgaaatgc taaagagaac taattttaaa tgtaatattg   6300
atgttgaaca tgtggtcaat cattttatgt ttgctcccga tggacgttcc gttatgttca   6360
tacatcgata ctatacacct aaaggaaagc gtgaaaggtt aatacattgg aatttaataa   6420
atgataatgt tcgagtccta ataaatgaat cgattattag tcattgttgt tggaatggga   6480
atgatgaaat tataggtttt tttggtgcag aaatagattc gctaaattat tatagattgt   6540
caattgaatc ctgtaataca gagaaattgt tttttgatgc aagaaaatat tctgatggac   6600
atcctactat agttcataat agatatatta tatctgatac ttacccagat aaaaatagaa   6660
ttaaaaagtt gtttgtttat gaccttgtca aaaatgatta tcgcgagctt ggattatttt   6720
atgagtcaat gagttttttt tcttattctc gatgtgactt acatccaagg atctcggttg   6780
ataatagatt tttgtttgtt gattcagttc actcagggaa aagaaaacta tattttatga   6840
ggagtggtat ttgtgagtga tgttctagta tctttaatta tagtttgctt taatgcagag   6900
aagtatattg aaaaatctct tttggcattt attaatcaag atgttggatt agataaattt   6960
gaattgatta ttgtagatgg ggattcatct gataatacaa tatctattgt tcaggatgtt   7020
ttttctaaac atagcaacat taagcataaa attatcaata ataaaaaaag aactcttgct   7080
acgggttgga atattggggt gctagaagct aatggtaagt ttgtgtgtag agttgatgca   7140
catagtgata ttccaaataa ctatatatct aaattattag atgattattt taatattatg   7200
cagtttgatg atagcgttgt tggtgttgga ggtgtattaa ctaattctta taaaactaag   7260
tttggttcaa ttgtagcgga tttttatgca tcgaaatttg gtgttggtaa ttctccattt   7320
aggtgcgtag acaaaaataa tcgactaaaa aaaacagata cagctgtctt tgctttatat   7380
aataaagatg tgtttttga tgttggactt tttaatgaag tattagatag aaatcaagat   7440
attgattttc ataagagagt tttaagcaat aatttgtcat tatatacaga taatagttta   7500
tttgttgagt attatgttag agataatttt aaagatttca taaagaaagg ttttcttgat   7560
ggtttttggg ttgttatgtc tggagcatat tattttagac atatagtgcc actttttttt   7620
gttttgtatt taattgtatc tttttctctt ttctttgcta ctggtgatta tatatattta   7680
tctttttat tttttattt tcttatttct attttgtttt caattcgaga tgggcgaagt   7740
tttataggta gagtatttct tcctttata tttttgtctt atcatatttc ttatggatgt   7800
ggatcgttat tatctttttt gaaaaggtat tttaaatgaa aaattttatt ccttttgcgt   7860
tacctgaaat tggcgaagaa gaaattgcag aggtaattga ctctttacgt tcaggttgga   7920
ttacgacagg tcctaaggct aagcaatttg aacaagaatt ttctaattac ctaggagcga   7980
acgttcaatc attagctgtt aactctgcta cgtcgggctt acatttggct cttgaagctg   8040
ttggcgtaaa gccgggagac caagttattg tcccatcata tacattcact gctactgccg   8100
aaattgtcag gtaccttggt gctgatcctg taattgttga tgtagatcgt aaaacattta   8160
```

-continued

```
atatatcagt tgatgccatt gagaaggcta ttactaatga aacaaaggcg attattccag   8220
tacacttcgc tggattagct tgtgacatgg attcaatctt atcaattgct aaaaaatatg   8280
acctaaaggt tgtcgaggat gccgctcatg catttcctac aacatataaa ggaagtaaga   8340
taggaacgct tgattcagat gctacggttt ttagcttcta cgccaataaa actatgacaa   8400
ccggtgaagg cggaatggtt gtttcaaaaa ataaagatat aattgagcgt tgtaaggtaa   8460
tgcgtttaca tggaatcagt cgtgacgctt ttgaccggta ccagtctaaa actccttctt   8520
ggttttatga ggttgtagct ccagggttta aatacaatat gcctgatatc tgtgcggcaa   8580
tcggtattca tcaacttaga aagatcgatg attttcagaa aaaacgtcaa cgaatggcaa   8640
aaatttacga tgatgcgtta aaagaattgc cacttgaatt gcctgaatgg cctactaatg   8700
ctagtgatat tcatgcttgg catctatatc ctatccgctt aaaaaactgat tcggctatta   8760
atcgcgatga ttttattaag aagttatcag atcttggaat tggttgttct gtccatttta   8820
taccgttgca taagcaaccg gtttggcgtg atacatataa tttgaacgcc agtgactttc   8880
cagtttctga ggagtgttat ttaaatgaaa tatctattcc tctttatact aaaatgacgg   8940
atcaagatca gttgttcgtt atcaaatcga ttagacaatt atttatgtaa tggtatttta   9000
tattaaatga aacgtatttt tgatgttatc gtggcaggct taggcctgct ttttctattt   9060
cctgttttta tcattgtgtc aatgttaatt gttgctgatt ctaaaggggg ggttttttt   9120
aggcagtata gagttgggag atttgggaaa gattttagga tacataaatt tagaacgatg   9180
tttatcgatt cagaaaaaaa aggacggata acagttggtc aagatgctcg ggtaaccaga   9240
gttggatggt atttacggaa gtacaaaatc gatgagcttc ctcaattgat agatgttctt   9300
tctggaacaa tgagtttggt tggcccaaga ccggaagtga gggagtttat tgatgagtat   9360
cctgatgata taagggaaaa agttttatcg gttaggccag ggataactga cttagcatct   9420
atagaaatgg tagatgaaaa tgagattttg tctagttatg atgacccacg tagggcttat   9480
atagatataa ttcttccaat caagcaaaga tattatttag attatgttgc taacaattca   9540
gtaaagtatg attgtgtgat aatttggaaa actattatta agattttgtc gcgataataa   9600
ggtagtgtag gatgattgat agaatattgg agctgccaag aattgttaag agaggtatca   9660
tcatctgcat tgatgtagtt atggtgatat tctcattttg gttgtcttat tggttgaggc   9720
ttgatgagca aacggctttt cttagtgcac cgatgtggtt tgctgcagct attcttacca   9780
tatttaccgt gtttatattt atcaggattg ggctttatcg ggcagtctta cggtatgtta   9840
gtgcaaagat aatgttgcta ataccagttg gtattctggc ctcaacgtta tctcttgtcg   9900
ttatatcata ttcgctatcc ataatgttgc cgcgcactgt tgtcggaatt tattttttgg   9960
ttttactttt actgacatca ggctctagat tgctttttag aatgatactt aactatggag  10020
ttaagggtag tgcgcctgtt ttgatttatg gcgctggtga atctggccga caattattgc  10080
cagcattaat gcaggcaaaa gaatattttc ctgtggcatt tgtggatgat aatcctcgct  10140
tgcataaggc tgtcattcat ggtgtaacag tttatccctc ggataaactg agttaccttg  10200
tagatcgcta tggtataaag aaaattcttt tggcgatgcc gagcgtcagt aagtcacaaa  10260
ggcagaaagt gattactcgt ttagagcatc taccgtgtga agttctctct attccgggta  10320
tggtcgattt agtcgaaggt cgagcacaaa tcagtaatct aaaaaaagta tcgattgatg  10380
acttactagg tcgtgatccg gttgctcctg atgccaaatt gatggccgaa aacattactg  10440
gcaaagccgt tatggtcact ggggcgggag gctcgatcgg ctctgagctt tgtcgtcaaa  10500
ttgttcgata taagccggcc aaattggttc tatttgaact gtctgaatat gccctctacg  10560
```

-continued

```
ctattgagaa agagctctcg gcgctgtgcg acaaagaagt tttgaatgtt ccagtgatcc  10620
ctctgttggg ctcggtgcag cgtcagaatc gcttacagat ggtgatgaag tcctttggta  10680
ttcaaacggt ttatcatgcg gccgcttata aacatgtgcc tctggttgag cataatgtgg  10740
tggaaggggt acgtaataac gtgtttggta ccttgtactg cgctgagtca gcgatcgaaa  10800
gtggcgttga aacttttgtg ttgatttcca ccgataaagc ggtgcgcccg accaacacta  10860
tggggacaac taagcgtctg gccgaattgg tattgcaggc tttgtctgca cggcaaagcc  10920
aaactcgctt ttgtatggtg cgatttggta atgtactcgg ttcttcgggc tctgtcgtgc  10980
cgttgtttga aaaacagatt gcccaaggtg ggccagttac cttgactcat cgtgacatta  11040
ttcgctattt catgacaatt ccggaagcat cacagttggt gattcaagcg ggggcgatgg  11100
ggcatggcgg cgatgtcttt gtcttagaca tgggcgatcc ggtcaagatt tatgacttag  11160
ccaaacgcat gatccggtta agtggcttga gtgtacggga tgataaaaat ccagatggcg  11220
atattgccat tgaagttacg ggattacgtc caggggagaa actgtatgaa gaattactga  11280
ttggtgattc agttcaaggt acctctcatc cacgaattat gacggccaac gaagtgatgc  11340
taccgtggca ggatctatcg ctcttactta aagagctgga tcaagcttgt catgactttg  11400
atcatgagcg aattcgcagt ttgttgttac aagcaccagc ggcattcaat ccaactgatg  11460
atatttgcga tctagtttgg cagcagaaaa aatcgctgtt atcacaagcg agcaatgtca  11520
ttcgcctgtg attgcttagg tttaaccttc cacaccaatt cttcacctct cttacaaatc  11580
cccgctaggc ggtacatcgt gaccgccttt agcctgatgc ctgctcttta acaaacagga  11640
catcagtgta tgtttaaacc ttttagcgcc gaatttttcg gcactttctg gctggttctg  11700
ggtggctgtg gtagcgcctt gatctctgct gctttcccac agttaggtat aggcttttg  11760
ggcgtggcgt tggcgtttgg tctgacagta gtcaccatgg cttatgcggt cgggcacatc  11820
tctggtgcgc attttaaccc cgcggtgacc ttgggtctgt gggccggtgg acgcttccca  11880
gcagcgcgcg tgttacctta cattatcgct caggttatcg gcggtattgc cgctgcggca  11940
gtgctgtatg gtatcgccag cggtaaggct gggtttgatg cgacaaccag cggttttgcg  12000
gctaatggtt atggcctcca ttcacctggc ggctatgcgt taagcgcctg tatgctgagc  12060
gagtttgtcc tcagtgcgtt ttttgtccgg agcgacagaa aaacgcgctc ctgcgggctt  12120
tgcgccactg gcgattggtc tggtaatcac cccgtaaatt aactcgagta attaatgggc  12180
atcatttttc agctatttca tttataaaat aagttatgaa aaaaatcatc atattactaa  12240
cgacattttt cctgctttcg ggatgcacta ttcccagggc ggtatttaaa tccagcctta  12300
ttaatcagga cgatcctcgt tataatctgg tcgaagtcac gccgacatta aaactaagcg  12360
ctcccgatac tgtgccgaaa actattgtcg atccggtttt tgccgcaaat aactggcact  12420
ggacatcttt ggctaaaggc gatgtgctgc atatcactat tttatcctcg ggcggggctg  12480
gatatttatc caataacgcg agcggcgacc gtgcggattt tgaaaatatt cttgtgactg  12540
acagtaatac cgttcaggtg ccttatgccg ggacaatccc ggtttctgga ttggatgtga  12600
cgcaactggc tgatgagatc aaaaagcgac tttcgcgcgt tgtcctgaat cctcaggtga  12660
ttgtgacact taccgcccgc accggagcca tggtgacggt cgagggcagc gggaaaacgg  12720
gtcgataccc tctcgaacag agtatgaatc gtctgagtca tcttttggca acggcagtgg  12780
cagtagaaaa taccagcaca gatatgatgg aagttcacgt gacgcgccag cagcattatt  12840
tcactgcgcg actgtcagat atttatcagt atcccggatt ggatattgcc ttacagccgg  12900
```

atgaccgtat cactctgcgt caagtgaccg agtatgttaa tgtgctcggc gcagcaggtg 12960
ttcaggggaa acatgctctg gttcagcgtc attccagcgt cgtggatgct ttggcgctcg 13020
cgaaaggatt aaatgacaat cttgccgatc cgcaagcgat tttctgtac aagcataacg 13080
aagcggaaca ggcgaaacag cagatgcgta agctgaatat ctatcatgtc gatatgagcc 13140
aacctaactc ggtgttttta gcgcaggcca tacgagtgga caacggcgat gttatctata 13200
tctcgaacgc ctctttgact gatttcgcta aggtgaaagc cgcattcgat agctttttga 13260
cccgcggcac taattctttc taaggcgcgc cggtaccgaa ttcccgacag taagacgggt 13320
aagcctgttg atgataccgc tgccttactg ggtgcattag ccagtctgaa tgacctgtca 13380
cgggataatc cgaagtggtc agactggaaa atcagagggc aggaactgct gaacagcaaa 13440
aagtcagata gcaccacata gcagacccgc cataaaacgc cctgagaagc ccgtgacggg 13500
cttttcttgt attatgggta gtttccttgc atgaatccat aaaaggcgcc tgtagtgcca 13560
tttacccca ttcactgcca gagccgtgag cgcagcgaac tgaatgtcac gaaaaagaca 13620
gcgactcagg tgcctgatgg tcggagacaa aaggaatatt cagcgatttg cccgagcttg 13680
cgagggtgct acttaagcct ttagggtttt aaggtctgtt ttgtagagga gcaaacagcg 13740
tttgcgacat ccttttgtaa tactgcggaa ctgactaaag tagtgagtta tacacagggc 13800
tgggatctat tctttttatc ttttttatt ctttctttat tctataaatt ataaccactt 13860
gaatataaac aaaaaaaaca cacaaaggtc tagcggaatt tacagagggt ctagcagaat 13920
ttacaagttt tccagcaaag gtctagcaga atttacagat acccacaact caaaggaaaa 13980
ggactagtaa ttatcattga ctagcccatc tcaattggta tagtgattaa aatcacctag 14040
accaattgag atgtatgtct gaattagttg ttttcaaagc aaatgaacta gcgattagtc 14100
gctatgactt aacggagcat gaaaccaagc taattttatg ctgtgtggca ctactcaacc 14160
ccacgattga aaaccctaca aggaaagaac ggacggtatc gttcacttat aaccaatacg 14220
ctcagatgat gaacatcagt agggaaaatg cttatggtgt attagctaaa gcaaccagag 14280
agctgatgac gagaactgtg gaaatcagga atcctttggt taaaggcttt gagattttcc 14340
agtggacaaa ctatgccaag ttctcaagcg aaaaattaga attagttttt agtgaagaga 14400
tattgcctta tcttttccag ttaaaaaaat tcataaaata taatctggaa catgttaagt 14460
cttttgaaaa caaatactct atgaggattt atgagtggtt attaaaagaa ctaacacaaa 14520
agaaaactca caaggcaaat atagagatta gccttgatga atttaagttc atgttaatgc 14580
ttgaaaataa ctaccatgag tttaaaaggc ttaaccaatg ggttttgaaa ccaataagta 14640
aagatttaaa cacttacagc aatatgaaat tggtggttga taagcgaggc cgcccgactg 14700
atacgttgat tttccaagtt gaactagata gacaaatgga tctcgtaacc gaacttgaga 14760
acaaccagat aaaaatgaat ggtgacaaaa taccaacaac cattacatca gattcctacc 14820
tacataacgg actaagaaaa acactacacg atgctttaac tgcaaaaatt cagctcacca 14880
gttttgaggc aaaatttttg agtgacatgc aaagtaagta tgatctcaat ggttcgttct 14940
catggctcac gcaaaaacaa cgaaccacac tagagaacat actggctaaa tacggaagga 15000
tctgaggttc ttatggctct tgtatctatc agtgaagcat caagactaac aaacaaaagt 15060
agaacaactg ttcaccgtta catatcaaag ggaaaactgt ccatatgcac agatgaaaac 15120
ggtgtaaaaa agatagatac atcagagctt ttacgagttt ttggtgcatt caaagctgtt 15180
caccatgaac agatcgacaa tgtaacagat gaacagcatg taacacctaa tagaacaggt 15240
gaaaccagta aaacaaagca actagaacat gaaattgaac acctgagaca acttgttaca 15300

```
gctcaacagt cacacataga cagcctgaaa caggcgatgc tgcttatcga atcaaagctg  15360
ccgacaacac gggagccagt gacgcctccc gtggggaaaa aatcatggca attctggaag  15420
aaatagcgct ttcagccggc aaacctgaag ccggatctgc gattctgata acaaactagc  15480
aacaccagaa cagcccgttt gcgggcagca aaacccgtgg gaattaattc ccctgctcgc  15540
gcaggctggg tgccaagctc tcgggtaaca tcaaggcccg atccttggag cccttgccct  15600
cccgcacgat gatcgtgccg tgatcgaaat ccagatcctt gacccgcagt tgcaaaccct  15660
cactgatccg catgcccgtt ccatacagaa gctgggcgaa caaacgatgc tcgccttcca  15720
gaaaaccgag gatgcgaacc acttcatccg gggtcagcac caccggcaag cgccgcgacg  15780
gccgaggtct tccgatctcc tgaagccagg gcagatccgt gcacagcacc ttgccgtaga  15840
agaacagcaa ggccgccaat gcctgacgat gcgtggagac cgaaaccttg cgctcgttcg  15900
ccagccagga cagaaatgcc tcgacttcgc tgctgcccaa ggttgccggg tgacgcacac  15960
cgtggaaacg gatgaaggca cgaacccagt ggacataagc ctgttcggtt cgtaagctgt  16020
aatgcaagta gcgtgctagc ccgttcctca ttgatttgat tgctaacgtc atgagcatta  16080
ctctatcatt ccagaatgcc tcaatgaaca agttgtttga gaaagagtgt cgcaatgttg  16140
caaccagagc ccttaaatat gtacgccaga agaaaactga agggcgtctg gatgaagcat  16200
tgtctgtatt gattagcctg aaacgaattg agcctgatgt ttctcgtctg atgcgtgaat  16260
ataagcaaat tatcagatta tttaatgagt cacggaagga tggcggtagc actatcacgt  16320
cttatgaaca tctagactat gcgaaaaaat tactcgtttt tgatagcgaa aatgcctatg  16380
ccttgaaata tgccgcatta aatgcaatgc atttacgcga ctacacgcag gctttgcagt  16440
attggcagcg actggagaaa gtgaatggac caacggagcc ggtgacaagg cagatctcga  16500
cctgcataac cgcattacaa aaaaatacat cagggaagtc gtaacccggg gtgtaggctg  16560
gagctgcttc gaagttccta tactttctag agaataggaa cttcggaata ggaacttcaa  16620
gatcccctca cgctgccgca agcactcagg gcgcaagggc tgctaaagga agcggaacac  16680
gtagaaagcc agtccgcaga aacggtgctg accccggatg aatgtcagct actgggctat  16740
ctggacaagg gaaaacgcaa gcgcaaagag aaagcaggta gcttgcagtg ggcttacatg  16800
gcgatagcta gactgggcgg ttttatggac agcaagcgaa ccggaattgc cagctggggc  16860
gccctctggt aaggttggga agccctgcaa agtaaactgg atggctttct tgccgccaag  16920
gatctgatgg cgcaggggat caagatctga tcaagagaca ggatgaggat cgtttcgcat  16980
gattgaacaa gatggattgc acgcaggttc tccggccgct tgggtggaga ggctattcgg  17040
ctatgactgg gcacaacaga caatcggctg ctctgatgcc gccgtgttcc ggctgtcagc  17100
gcaggggcgc ccggttcttt ttgtcaagac cgacctgtcc ggtgccctga atgaactgca  17160
ggacgaggca gcgcggctat cgtggctggc cacgacgggc gttccttgcg cagctgtgct  17220
cgacgttgtc actgaagcgg gaagggactg gctgctattg ggcgaagtgc cggggcagga  17280
tctcctgtca tctcaccttg ctcctgccga gaaagtatcc atcatggctg atgcaatgcg  17340
gcggctgcat acgcttgatc cggctacctg cccattcgac caccaagcga aacatcgcat  17400
cgagcgagca cgtactcgga tggaagccgg tcttgtcgat caggatgatc tggacgaaga  17460
gcatcagggg ctcgcgccag ccgaactgtt cgccaggctc aaggcgcgca tgcccgacgg  17520
cgaggatctc gtcgtgaccc atggcgatgc ctgcttgccg aatatcatgg tggaaaatgg  17580
ccgcttttct ggattcatcg actgtggccg gctgggtgtg gcggaccgct atcaggacat  17640
```

-continued

```
agcgttggct acccgtgata ttgctgaaga gcttggcggc gaatgggctg accgcttcct  17700

cgtgctttac ggtatcgccg ctcccgattc gcagcgcatc gccttctatc gccttcttga  17760

cgagttcttc tgagcgggac tctggggttc gaaatgaccg accaagcgac gcccaacctg  17820

ccatcacgag atttcgattc caccgccgcc ttctatgaaa ggttgggctt cggaatcgtt  17880

ttccgggacg ccggctggat gatcctccag cgcggggatc tcatgctgga gttcttcgcc  17940

caccccagct tcaaaagcgc tctgaagttc ctatactttc tagagaatag gaacttcgga  18000

ataggaacta aggaggatat tcatatatgc attaatgtct aacaattcgt tcaagccgac  18060

gccgcttcgc ggcgcggctt aactcaagcg ttagatgcac taagcacata attgctcaca  18120

gccaaactat caggtcaagt ctgcttttat tatttttaag cgtgcataat aagccctaca  18180

caaattggga gatatatcat gaaaggctgg ctttttcttg ttatcgcaat agttggcgaa  18240

gtaatcgcaa catccgcatt aaaatctagc gagggcttta ct                    18282


<210> SEQ ID NO 25
<211> LENGTH: 33
<212> TYPE: DNA
<213> ORGANISM: Shigella sonnei
<220> FEATURE:
<221> NAME/KEY: misc_feature
<223> OTHER INFORMATION: prMD92

<400> SEQUENCE: 25

gttgcggtaa tggtataacg aaataacaga tac                                 33


<210> SEQ ID NO 26
<211> LENGTH: 25
<212> TYPE: DNA
<213> ORGANISM: Shigella sonnei

<400> SEQUENCE: 26

cacgcaatat ttcaatgatg gcaac                                          25


<210> SEQ ID NO 27
<211> LENGTH: 36
<212> TYPE: DNA
<213> ORGANISM: Shigella dysenteriae
<220> FEATURE:
<221> NAME/KEY: misc_feature
<223> OTHER INFORMATION: prMD127.dy.F.HindIII

<400> SEQUENCE: 27

gatcgaagct tggcattttt tgtcattttt ggatgc                              36


<210> SEQ ID NO 28
<211> LENGTH: 36
<212> TYPE: DNA
<213> ORGANISM: Shigella dysenteriae
<220> FEATURE:
<221> NAME/KEY: misc_feature
<223> OTHER INFORMATION: prMD128.dy.R.wbbP.BamHI

<400> SEQUENCE: 28

gatcgggatc catcgatatg gctgggtaag gtcatg                              36


<210> SEQ ID NO 29
<211> LENGTH: 38
<212> TYPE: DNA
<213> ORGANISM: Shigella dysenteriae
<220> FEATURE:
<221> NAME/KEY: misc_feature
<223> OTHER INFORMATION: prMD129.F.BamHI
```

<400> SEQUENCE: 29
gatcgggatc ctaatgaaaa tctgaccgaa tgtaacgg 38

<210> SEQ ID NO 30
<211> LENGTH: 39
<212> TYPE: DNA
<213> ORGANISM: Shigella dysenteriae
<220> FEATURE:
<221> NAME/KEY: misc_feature
<223> OTHER INFORMATION: prMD130.R.EcoRI

<400> SEQUENCE: 30
gatcggaatt ctcacattaa tgctaccaaa aagagtcgc 39

<210> SEQ ID NO 31
<211> LENGTH: 197
<212> TYPE: DNA
<213> ORGANISM: Shigella dysenteriae
<220> FEATURE:
<221> NAME/KEY: misc_feature
<223> OTHER INFORMATION: prMD151.lpp.R

<400> SEQUENCE: 31
aggaatggcg cctgcttttt ttattatttc cttggatgaa tcattatagt cagtagcaaa 60
agcatagact gaaatccctt tcttggttag tgtttttatt aaatccaatc taaacaaaat 120
catagcattt gctgtgttcc ctattattga gatcttcata tgtcctctcc tttcattatt 180
aataccctct agagttc 197

<210> SEQ ID NO 32
<211> LENGTH: 12797
<212> TYPE: DNA
<213> ORGANISM: Shigella dysenteriae
<220> FEATURE:
<221> NAME/KEY: misc_feature
<223> OTHER INFORMATION: Ty21a-Sdl (MD174) *S. dysenteriae* O-antigen genes integrated into tviD-VexA on the chromosome, expressed from lpp promoter 12797 bp

<400> SEQUENCE: 32
cacgcaatat ttcaatgatg gcaacgcatt ctctgaagct ttccatgccg gcattcaatc 60
gcagcgccta aatgatacgt ttatggaaac ggcgttatct ttggcaatca aattcagtga 120
tgaattgatt ttcatgcatg cgctcgagca gctactccgc catgagtcag aatttgcgct 180
gacggtattg tcgacgattc atgataccgg tctcgttatc cgcacagctt tctgcatcaa 240
gaatatgagc tatcatcaag cgcttcgcac ctcgtataaa gataaaatcc acgacgtttt 300
tgaggcatgg aacaataccg cgctgtcgct acattcggtt gatgattttg tctcactgag 360
tacttcgcta gcctatagct actctgcatt tatggtttat ccccattcac gtatttctcg 420
ctttaataat gaagttaaaa tggcatggcg cgataaatta agagaaatgt atgagcgtga 480
ggattatgaa aatatcctgg caggggcgaa aatagtgtgg ccacttctga agtttgatcc 540
cgttggcacc gtatattgtg caagaacgct ggtgaatctt ggtgcctgga aagacgcgtg 600
cacgttggcc cacatgacct tgattcgtaa ctcgaacatt accagcctgc agtcgattat 660
gttacgcagc atacgtcata ttaacaacat tccgttcctc attgatttga ttgctaacgt 720
catgagcatt actctatcat tccagaatgc ctcaatgaac aagttgtttg agaaagagtg 780
tcgcaatgtt gcaaccagag cccttaaata tgtacgccag aagaaaactg aagggcgtct 840
ggatgaagca ttgtctgtat tgattagcct gaaacgaatt gagcctgatg tttctcgtct 900

-continued

```
gatgcgtgaa tataagcaaa ttatcagatt atttaatgag tcacggaagg atggcggtag    960
cactatcacg tcttatgaac atctagacta tgcgaaaaaa ttactcgttt ttgatagcga   1020
aaatgcctat gccttgaaat atgccgcatt aaatgcaatg catttacgcg actacacgca   1080
ggctttgcag tattggcagc gactggagaa agtgaatgga ccaacggagc cggtgacaag   1140
gcagatctcg acctgcataa ccgcattaca aaaaaataca tcagggaagt cgtaacccgg   1200
ggtgtaggct ggagctgctt cgaagttcct atactttcta gagaatagga acttcggaat   1260
aggaactaag gaggatattc atatatgcat taatgtctaa caattcgttc aagccgacgc   1320
cgcttcgcgg cgcggcttaa ctcaagcgtt agatgcacta agcacataat tgctcacagc   1380
caaactatca ggtcaagtct gcttttatta tttttaagcg tgcataataa gccctacaca   1440
aattgggaga tatatcatga aaggctggct tttcttgtt atcgcaatag ttggcgaagt   1500
aatcgcaaca tccgcattaa aatctagcga gggctttact gtcgaccaaa aaaatattga   1560
caacataaaa aactttgtgt tatacttgta acgctacatg gagattaact caatctagct   1620
agagaggctt tacactttat gcttccggct cgtataatgt gtggaattgt gagcggataa   1680
caatttcaca caggaaacag ctatgaccat gattacggat tcactggaac tctagagggt   1740
attaataatg aaaggagagg acatatgaag atctcaataa tagggaacac agcaaatgct   1800
atgattttgt ttagattgga tttaataaaa acactaacca agaaagggat ttcagtctat   1860
gcttttgcta ctgactataa tgattcatcc aaggaaataa taaaaaaagc aggcgccatt   1920
cctgttgatt ataatttaag tcgcagtggt attaaccttg ctggtgattt atggaatact   1980
tacttattaa gtaaaaaact aaagaagata aaaccagatg ctattttatc tttttttca   2040
aagccctcta tctttggatc gttggctggt attttttcag gcgttaaaaa taataacgct   2100
atgcttgagg ggttaggttt tttatttaca gagcagccac atggaactcc gttaaaaaca   2160
aagttactta aaaatatcca ggttctcctg tataaaataa tatttccaca tatcaactca   2220
ttaatactcc ttaacaagga tgattatcat gatttgatag ataaatacaa aataaaatta   2280
aaatcttgcc atattcttgg tggcattggt ttagatatga ataattactg taaaagcacg   2340
ccaccaacaa atgaaatatc attcattttt atagctcgtt tgctagcaga aaaaggagtc   2400
aatgagtttg tgcttgccgc aaaaaaaata aaaaaaacac atcccaatgt tgaatttatt   2460
atacttggcg ctatagataa ggaaaacccc ggagggttat ctgaatctga cgtagatact   2520
ttaattaaat caggagttat ttcttatccc ggatttgttt ctaatgtggc tgattggatt   2580
gaaaaatcaa gcgtatttgt tcttccttcc tattatcgag agggagttcc tcgtagtaca   2640
caagaagcga tggctatggg gaggccgatt ttaactacta atttaccagg ctgcaaagaa   2700
acaattattg atggtgtgaa tggatatgtt gtaaaaaaat ggtcacatga agatcttgca   2760
gaaaaaatgc tgaagttaat taataatcct gaaaaaataa tcagtatggg agaagaaagt   2820
tataagttag caagagaaag attcgatgca aatgtaaata atgtaaagtt attaaaaata   2880
ctagggattc ctgattaata aacgaaaagc ggctctgatt cattcggaac taagaaccta   2940
tctcaatagg agctaaattc atgaccttac ccagccatat cgatggatcc taatgaaaat   3000
ctgaccgaat gtaacggttg ataagaaaat tataacggca gtgaagattc gtggcgaaag   3060
taatttgttg cgaatattcc tgccgttgtt ttatataaac aatcagaata acaaagagtt   3120
agcaatagga ttttcgtcaa agttttccag gattttcctt gtttccagag cggattggta   3180
agacaattag tgtttgaatt tttcgggttt agcgcgagtg ggtaacgctc gtcacatcgt   3240
```

-continued

```
ggacatgtat gcagtgctct ggtagctgta aagccagggg cggtagcgtg cattaatacc   3300
tctattaatc aaactgagag ccgcttattt cacagcatgc tctgaagtaa tatggaataa   3360
taaagtgaag atacttgtta ctggtggcgc aggatttatt ggttctgctg tagttcgtca   3420
cattataaat aatacgcagg atagtgttgt taatgtcgat aaattaacgt acgccggaaa   3480
cctggagtca cttgctgatg tttctgactc taaacgctat gtttttgaac atgcggatat   3540
ttgcgatgct gctgcaatgg cgcggatttt tgctcagcat cagccggatg cagtgatgca   3600
cctggctgct gaaagccatg tggatcgttc aattacaggc cctgcggcat ttattgaaac   3660
caatattgtt ggtacttatg tcctttttgga agcggctcgc aattactggt ctgctcttga   3720
tggcgacaag aaaaatagct tccgttttca tcatatttct actgacgaag tctatggtga   3780
tttgcctcat cctgacgaag taaataataa agaacaatta cccctcttta ctgagacgac   3840
agcttacgcg cctagtagtc cttattccgc atcaaaagca tccagcgatc atttagtccg   3900
tgcgtggaaa cgtacctatg gtttaccgac cattgtgact aactgttcga ataactacgg   3960
tccttatcac tttccggaaa aattgattcc actagtaatt cttaatgctc tggaaggtaa   4020
ggcattacct atttatggca aaggggatca aattcgtgac tggctgtatg ttgaagatca   4080
tgcgcgtgcg ttatatatcg tcgtaaccga aggtaaagcg ggtgaaactt ataacattgg   4140
tggacacaac gaaaagaaaa acatcgatgt agtgctcact atttgtgatt tgttggatga   4200
gattgtaccg aaagagaaat cttaccgcga gcaaattact tatgttgccg atcgcccggg   4260
acacgatcgc cgttatgcga ttgatgcaga gaagattagc cgcgaattgg gctggaaacc   4320
gcaggaaacg tttgagagcg ggattcgtaa aacggtggga tggtacctct ccaatacaaa   4380
atgggttgat aatgtaaaaa gtggtgccta tcaatcgtgg attgaacaga actatgaggg   4440
ccgccagtaa tgaatatcct ccttttcggc aaaacagggc aggtaggttg ggaactacag   4500
cgtgctctgg cacctctggg taatttgatt gctcttgatg ttcactccac tgattactgt   4560
ggtgatttta gtaatcctga aggtgtagct gaaaccgtaa gaagcattcg gcctgatatt   4620
attgtcaacg cagccgctca caccgcagta gacaaagcag aatcagaacc ggagtttgca   4680
caattactta acgcgacgag tgtcgaagcg atcgcgaaag cagccaatga agtcggcgcc   4740
tgggttattc actactctac tgactacgta tttccgggga ccggtgaaat accatggcag   4800
gaggcggatg caaccgcacc gctaaatgtt tacggtgaaa ccaagttagc tggagaaaaa   4860
gcattacaag agcattgtgc gaagcaccta attttccgta caagctgggt ctatgcaggt   4920
aaaggaaata acttcgccaa aacgatgttg cgtctgggaa aagagcgtga agaattagcc   4980
gttattaatg atcagtttgg tgcgccaaca ggtgctgaac tgctggctga ttgtacggca   5040
catgcaattc gtgtggcact gaataaacca gaagtcgcag gcttgtacca tctggtagcc   5100
actggtacca caacctggca cgattatgct gcgctggttt ttgaagaggc acgaaaagca   5160
ggtattcccc ttgcactcaa caagctcaac gcagtaccaa caacagctta tcctacacca   5220
gctcgtcgtc cacataactc tcgccttaat acagaaaaat ttcagcaaaa ttttgcgctt   5280
gttttgcctg actggcaggt tggcgtgaaa cgaatgctca acgaattatt tacgactaca   5340
gcaatttaat agtttttgca tcttgttcgt gatgatggag caagatgaat taaaaggaat   5400
gatgtaatga aaacgcgtaa aggtattatt ttagcgggtg gctctggtac tcgtctttat   5460
cctgtgacta tggctgtcag taaacagcta ttacctattt atgataagcc gatgatctat   5520
tacccgctct ctacactgat gttggcgggt attcgcgata ttctgattat tagtacgcca   5580
caggatactc ctcgttttca acaactcctg ggtgatggta gccagtgggg gttaaatctt   5640
```

```
cagtacaaag tgcaaccgag tccagatggt cttgcgcagg catttatcat cggtgaagag   5700
tttatcggtg gtgatgattg tgctctggtt ctcggtgata atatcttcta cggtcatgat   5760
ctgccgaagt taatggatgt cgctgtcaac aaagaaagtg gtgcaacggt atttgcctat   5820
cacgttaatg atcctgaacg ctacggtgtt gttgagtttg ataaaaacgg tacggcaatc   5880
agcctggaag aaaaaccgct acaaccaaaa agtaattatg cggtaaccgg gctttatttc   5940
tatgataacg acgttgtcga aatggcgaaa aaccttaagc cttctgcccg tggtgaactg   6000
gaaattaccg atattaaccg tatttatatg gagcaggggc gtttatccgt tgccatgatg   6060
ggacgtggtt atgcatggct ggacacgggg acacatcaaa gtcttattga agcaagcaac   6120
ttcattgcaa caattgaaga gcgccaaggg ttaaaggtat cttgcctgga agagattgct   6180
tatcgtaaag gctttattga cgcagagcag gttaatgtat tagccgaacc gctaaagaaa   6240
aatgcttatg gtcagtatct gttgaaaatg attaaaggtt attaaaaatg aatgtaatta   6300
aaactgaaat tccagatgta ttaattttcg agccgaaagt ttttggtgat gaacgtggtt   6360
tttttatgga aagctttaac cagaaagttt tcgaagaggc tgtagggcgg aaggttgaat   6420
ttgttcagga taaccattct aaatcaacta agggtgtgtt acgcggactg cactatcagt   6480
tggaacctta tgctcaaggt aaattagttc gttgtgttgt cggtgaagtt tttgatgtag   6540
cagttgatat tcgtaaatcg tcacctacat ttgggaaatg gattggggtg aatttgtctg   6600
ctgagaataa gcgtcagttg tggatacctg aaggatttgc gcatggattt ttggtgctga   6660
gtgaaacggc tgagtttgtt tataaaacaa caaactatta caatccaagt tttgaaaaaa   6720
gtatttcata ctcagatcct accattaaaa ttcagtggcc caatttacag gatatgcatt   6780
ttaaattatc aaataaggat ttgaatgcta agaacttttt taatgacaat agtttaatgc   6840
aatgaagaaa aatatattgc tcttgttctt agtacatggg gcaaattatt tgttcccgtt   6900
tatagttctt ccatatcaaa ctcgaatatt aagcatcgag acattcgcag atgtagcaaa   6960
aattcaagcc gctgtgatgc ttttatcttt aatcgtaaat tatggatata acttatcaag   7020
tacaagagct atagctaggg ccgtatctca agcagaaata aataagatct atagtgagac   7080
tcttattgta aaattattat tggcaaccat ttgtcttgca cttggttgcg tacatttgat   7140
gtatgtcaaa gagtactcat tgatatatcc ttttataatc agttcgatat atctttatgg   7200
tagtgcatta tttgctactt ggttattcca aggacttgag aaaatgaaag cggtcgttat   7260
agcaacaaca atcgctaaac tgactggtgt gatacttact tttattttag ttaagtctcc   7320
aaatgatata gttgcagctc tttttacaca aaacattggg atgtttataa gtggtataat   7380
atctatttat ttggtaagga aaaacaaata tgcaaccgta atatgttttc gacttaaaaa   7440
tattattgta agcttaaaag aagcgtggcc gtttttttta tcattagctg caacaagtgt   7500
atatacatat tttaatgtga ttttattatc tttttatgct ggcgactatg ttgtggcaaa   7560
ttttaatgct gctgataaat taagaatggc tgctcaaggg ttacttattc caataggaca   7620
ggctgttttc ccacgattat ctaaactaga gggctatgaa tatagttcta aacttaaaat   7680
ttatgcaata aggtatgcta tttttggtgt ttgcattagt gcgggacttg tatttttagg   7740
tcccatgtta actactattt atttaggcaa agaatattcg ttgtcaggag aatatcttca   7800
aagtatgttt ttactacctg ccactatttc aatatcgact atactgagtc aatggatgtt   7860
gatacctcaa ggcaaagaaa aaatattaag cagaatctat attctaggcg ccattgtcca   7920
tttattatat gcatttcctt tagtttacta ttatggggct tggggcatgg taatatcaat   7980
```

```
tttatttact gaagtcttaa ttgtattatt tatgcttaag gctgtgaaat gacttacttt   8040
actggtttta ttttaatatt gtttgctatt ataattaaaa gattaactcc aagtcaaagc   8100
aagaaaaata ttgtcttaat agctaatgcg ttttggggaa tattgttggt aggttatgct   8160
ttcaatgaac aatatttcgt accattaagt gcaacaacct tgttttttat acttgcattc   8220
ttatttttct ttagtatgac ttatatttta attgctagga gtggaagggt tgtttttttct   8280
ttcggtactg gttttataga aagcaaatat atttactggt ttgctgggat gattaatatt   8340
attagtatct gctttggcat tatcctttta tataataatc atttttcttt aaaagtaatg   8400
agagaaggaa ttttagatgg ttctattagt gggtttggat tggggataag tttgccactt   8460
tccttctgct gtatgtattt agcaagacat gagaataaaa aaaattattt ctattgtttt   8520
acactacttt cattcttgct tgcggtgtta tcaacttcaa agatcttctt aatattattc   8580
cttgtatata ttgttggaat aaatagttat gtaagcaaaa agaaattgct tatttatgga   8640
gtgtttgtat ttggactgtt cgctttatca agtattatct tgggtaagtt ctcttcagac   8700
cctgaaggca agattatttc agcaatattt gatacgttaa gggtttatct tttctcggga   8760
ttggcagcct ttaatcttta tgttgaaaag aatgccacgc tccccgaaaa tttacttttg   8820
tatccattta aggaggtttg ggggacgaca aaagatattc ccaaaactga tattttgcct   8880
tggatcaaca ttggtgtatg ggacacgaat gtatatacag cttttgcacc atggtatcag   8940
tcattgggat tatatgcagc tataattatt ggtattctct tagggtttta ttacgggata   9000
tggtttagct ttcgtcaaaa tttagctgtg ggtttttatc aaacattttt gtgttttcct   9060
cttttaatgt tgtttttcca ggagcattat ttgttgtcat ggaaaatgca ttttatttat   9120
tttttatgtg caattttatt agcgatgaga aaagcattag agtatgaata aatattgtat   9180
cttagtacta tttaatccag atataagtgt ttttattgat aatgtcaaaa agattttatc   9240
tttggatgta agtttatttg tatatgacaa ttcagcaaat aaacatgcat tccttgctct   9300
atcctcacaa gagcaaacaa agataaatta cttttcgata tgtgaaaata tcggattgtc   9360
gaaagcttat aatgagacac taaggcatat tcttgaattt aataagaatg tgaaaaataa   9420
aagcattaat gatagtgtgc tttttctcga ccaagactct gaagttgatt taaattccat   9480
caatattttg tttgaaacta tatcagcagc agagtctaat gtgatgatag tcgcggggaa   9540
tcccataagg agagatggac taccgtatat agattacccc cacactgtaa acaatgtaaa   9600
atttgtaatt agtagttatg ctgtgtatcg cttagacgca tttagaaaca tcggcttgtt   9660
tcaagaagat ttttttatag atcatatcga tagtgatttt tgttcaaggc tgataaaaag   9720
caattaccaa attctcctta gaaaagatgc cttttttat caaccaatag gaataaaacc   9780
attcaatctc tgtggtagat atttattccc tatcccatca caacaccgaa catattttca   9840
aattagaaat gctttttttaa gttacaggcg caatggtgtt acatttaatt ttttatttag   9900
ggaaattgta aatagattga ttatgagtat attctcaggc cttaacgaga aagacttatt   9960
gaaacgattg catttatatt taaaaggaat aaaagatggt cttaaaatgt aattcttggc  10020
tagaagtggg ggcgttgtga ttaaaaaaaa agtggcggcg ataattataa catataatcc  10080
agatctaaca attctgcgag aaagttatac gagtctatat aagcaagtcg ataaaataat  10140
tcttattgat aacaactcta caaactatca agaacttaag aagttattcg aaaaaaaaga  10200
aaaaataaaa atagtgccct tgagtgataa tataggacta gcagcagctc aaaatttagg  10260
tttgaactta gctattaaaa ataactatac ttatgctatt ttattcgatc aggatagcgt  10320
cttacaagac aatggaatta acagtttctt ttttgaattt gagaaattag ttagtgaaga  10380
```

```
aaaattaaat atagttgcca ttgggccaag tttttttgac gaaaagacag gaagacgctt  10440
tcggcctaca aaatttatcg gtccctttttt atatcccttt cgtaaaataa ccacaaaaaa  10500
tcctctaaca gaagttgact tcttgattgc ttctggttgt ttcataaaat tggagtgtat  10560
taaatcagcc ggaatgatga ctgaatcgtt attcatcgat tatattgatg ttgaatggtc  10620
atatcgtatg cgttcgtatg gctataagct atatattcat aatgatattc acatgagtca  10680
tttagtggga gaatctcgag ttaatttagg attgaaaact atttctttac atgggccgct  10740
aagacgatat tacttattta ggaattatat ttcaatttta aaagtgagat atataccgtt  10800
aggatataaa atacgtgagg gttttttttaa tatcggaaga tttttggtaa gtatgattat  10860
aactaaaaat agaaaaactt taattttata cactataaaa gcaattaagg acggaataaa  10920
taatgaaatg gggaaatata aaggctaaca acatattatg aaaaaaataa tacataacca  10980
agtgttgccg aaaatgtctg ggattcagca aatctctttt gatattttgt caggtcttaa  11040
agacaaggat gtacaaaaat ttatattatg cggtttacca gatggcagtt cagataatga  11100
atttaaaaag aaatttactg atataggtgt tagggttatt acgataccta cattaaaacg  11160
aaatatcggg tggcatgact ttcgatgttt cattgattta tacaattttt ttaaaaaaga  11220
aaaatttgat atagttcata caaactcaac taagccagga ataatagcta gaatagccgc  11280
tagattagcc gggacaaaac tcattattca cacagtacat ggaatcgcat ttcatagaaa  11340
agaaaatact gtaaggaaaa ttttgcgact ctttttggta gcattaatgt gagaattcta  11400
attaatgggc atcattttc agctatttca tttataaaat aagttatgaa aaaaatcatc  11460
atattactaa cgacattttt cctgctttcg ggatgcacta ttcccagggc ggtatttaaa  11520
tccagcctta ttaatcagga cgatcctcgt tataatctgg tcgaagtcac gccgacatta  11580
aaactaagcg ctcccgatac tgtgccgaaa actattgtcg atccggtttt tgccgcaaat  11640
aactggcact ggacatcttt ggctaaaggc gatgtgctgc atatcactat tttatcctcg  11700
ggcggggctg gatatttatc caataacgcg agcggcgacc gtgcggattt tgaaaatatt  11760
cttgtgactg acagtaatac cgttcaggtg ccttatgccg ggacaatccc ggtttctgga  11820
ttggatgtga cgcaactggc tgatgagatc aaaaagcgac tttcgcgcgt tgtcctgaat  11880
cctcaggtga ttgtgacact taccgcccgc accggagcca tggtgacggt cgagggcagc  11940
gggaaaacgg gtcgataccc tctcgaacag agtatgaatc gtctgagtca tcttttggca  12000
acggcagtgg cagtagaaaa taccagcaca gatatgatgg aagttcacgt gacgcgccag  12060
cagcattatt tcactgcgcg actgtcagat atttatcagt atcccggatt ggatattgcc  12120
ttacagccgg atgaccgtat cactctgcgt caagtgaccg agtatgttaa tgtgctcggc  12180
gcagcaggtg ttcaggggaa acatgctctg gttcagcgtc attccagcgt cgtggatgct  12240
ttggcgctcg cgaaaggatt aaatgacaat cttgccgatc cgcaagcgat tttctgtac  12300
aagcataacg aagcggaaca ggcgaaacag cagatgcgta agctgaatat ctatcatgtc  12360
gatatgagcc aacctaactc ggtgttttta gcgcaggcca tacgagtgga caacggcgat  12420
gttatctata tctcgaacgc ctctttgact gatttcgcta aggtgaaagc cgcattcgat  12480
agctttttga cccgcggcac taattctttc taatgtcgcc atatgaatat tttgaaaaat  12540
aattcttatt attttatgaa actcattacc gtctgtgagt taattatttt attgatgtca  12600
cgcgatatca aaacacgcta taacggtaat ttactaaact atatgatggt gctggccgta  12660
ccactggtat ggatatccat taccgttatt tcttttcaat atttaaatcg ctcggtgcca  12720
```

atatccactg acgatatcag ttttgttatt gcagggatat taccgtatct gttatttcgt 12780
tataccatta ccgcaac 12797

<210> SEQ ID NO 33
<211> LENGTH: 13151
<212> TYPE: DNA
<213> ORGANISM: Shigella dysenteriae
<220> FEATURE:
<221> NAME/KEY: misc_feature
<223> OTHER INFORMATION: Ty21a-Sd (MD149) *S. dysenteriae* O-antigen genes integrated into tviD-VexA on the chromosome, expressed from native promoter 13151bp

<400> SEQUENCE: 33
cacgcaatat ttcaatgatg gcaacgcatt ctctgaagct ttccatgccg gcattcaatc 60
gcagcgccta aatgatacgt ttatggaaac ggcgttatct ttggcaatca aattcagtga 120
tgaattgatt ttcatgcatg cgctcgagca gctactccgc catgagtcag aatttgcgct 180
gacggtattg tcgacgattc atgataccgg tctcgttatc cgcacagctt tctgcatcaa 240
gaatatgagc tatcatcaag cgcttcgcac ctcgtataaa gataaaatcc acgacgtttt 300
tgaggcatgg aacaataccg cgctgtcgct acattcggtt gatgattttg tctcactgag 360
tacttcgcta gcctatagct actctgcatt tatggtttat ccccattcac gtatttctcg 420
ctttaataat gaagttaaaa tggcatggcg cgataaatta agagaaatgt atgagcgtga 480
ggattatgaa aatatcctgg caggggcgaa aatagtgtgg ccacttctga agtttgatcc 540
cgttggcacc gtatattgtg caagaacgct ggtgaatctt ggtgcctgga aagacgcgtg 600
cacgttggcc cacatgacct tgattcgtaa ctcgaacatt accagcctgc agtcgattat 660
gttacgcagc atacgtcata ttaacaacat tccgttcctc attgatttga ttgctaacgt 720
catgagcatt actctatcat tccagaatgc ctcaatgaac aagttgtttg agaaagagtg 780
tcgcaatgtt gcaaccagag cccttaaata tgtacgccag aagaaaactg aagggcgtct 840
ggatgaagca ttgtctgtat tgattagcct gaaacgaatt gagcctgatg tttctcgtct 900
gatgcgtgaa tataagcaaa ttatcagatt atttaatgag tcacggaagg atggcggtag 960
cactatcacg tcttatgaac atctagacta tgcgaaaaaa ttactcgttt ttgatagcga 1020
aaatgcctat gccttgaaat atgccgcatt aaatgcaatg catttacgcg actacacgca 1080
ggctttgcag tattggcagc gactggagaa agtgaatgga ccaacggagc cggtgacaag 1140
gcagatctcg acctgcataa ccgcattaca aaaaaataca tcagggaagt cgtaacccgg 1200
ggtgtaggct ggagctgctt cgaagttcct atactttcta gagaatagga acttcggaat 1260
aggaactaag gaggatattc atatatgcat taatgtctaa caattcgttc aagccgacgc 1320
cgcttcgcgg cgcggcttaa ctcaagcgtt agatgcacta agcacataat tgctcacagc 1380
caaactatca ggtcaagtct gcttttatta tttttaagcg tgcataataa gccctacaca 1440
aattgggaga tatatcatga aaggctggct tttcttgtt atcgcaatag ttggcgaagt 1500
aatcgcaaca tccgcattaa aatctagcga gggctttact gtcgacgggc ggccgcaagc 1560
ttggcatttt ttgtcatttt tggatgcaga tgattactgg catccaaaaa aaactagaat 1620
tacaactatc atttattaat gatgaaaact tggatttttt aggttcaacg tgttccattg 1680
gtgagaaaaa taaccaagaa attaaccaag gaattaaaaa agaacattta aaattaaaaa 1740
taatttcatt taacatgatg ttgtttaaga attatttcca gactccagct gtcattatga 1800
aaagagatat ttttattcca tttaatgaga atcagcgttt ttcagaggac tacatgtcat 1860

-continued

```
ggcttgttat cgtttataat aaaaaaacaa atgtggatta atatatggaa gggatttggt   1920
ttttctcgat aaatttaact ttggagtgtc agggttgagt ggtaatttat ggttgatgga   1980
gaagtgggag ttaaaaaata tatttaactt cttgttgaaa ggtaaaataa tggcagtgcc   2040
tgcgatcttg ttttctttga taaaatatga aagaagatgc gctttaacaa agaaaaataa   2100
aggtaagggt aataaataat gaagatctca ataataggga acacagcaaa tgctatgatt   2160
ttgtttagat tggatttaat aaaaacacta accaagaaag ggatttcagt ctatgctttt   2220
gctactgact ataatgattc atccaaggaa ataataaaaa aagcaggcgc cattcctgtt   2280
gattataatt taagtcgcag tggtattaac cttgctggtg atttatggaa tacttactta   2340
ttaagtaaaa aactaaagaa gataaaacca gatgctattt tatctttttt ttcaaagccc   2400
tctatctttg gatcgttggc tggtattttt tcaggcgtta aaaataataa cgctatgctt   2460
gaggggttag gtttttattt tacagagcag ccacatggaa ctccgttaaa aacaaagtta   2520
cttaaaaata tccaggttct cctgtataaa ataatatttc cacatatcaa ctcattaata   2580
ctccttaaca aggatgatta tcatgatttg atagataaat acaaaataaa attaaaatct   2640
tgccatattc ttggtggcat tggtttagat atgaataatt actgtaaaag cacgccacca   2700
acaaatgaaa tatcattcat ttttatagct cgtttgctag cagaaaaagg agtcaatgag   2760
tttgtgcttg ccgcaaaaaa aataaaaaaa acacatccca atgttgaatt tattatactt   2820
ggcgctatag ataaggaaaa ccccggaggg ttatctgaat ctgacgtaga tactttaatt   2880
aaatcaggag ttatttctta tcccggattt gtttctaatg tggctgattg gattgaaaaa   2940
tcaagcgtat ttgttcttcc ttcctattat cgagagggag ttcctcgtag tacacaagaa   3000
gcgatggcta tggggaggcc gattttaact actaatttac caggctgcaa agaaacaatt   3060
attgatggtg tgaatggata tgttgtaaaa aaatggtcac atgaagatct tgcagaaaaa   3120
atgctgaagt taattaataa tcctgaaaaa ataatcagta tgggagaaga aagttataag   3180
ttagcaagag aaagattcga tgcaaatgta aataatgtaa agttattaaa aatactaggg   3240
attcctgatt aataaacgaa aagcggctct gattcattcg gaactaagaa cctatctcaa   3300
taggagctaa attcatgacc ttacccagcc atatcgatgg atcctaatga aaatctgacc   3360
gaatgtaacg gttgataaga aaattataac ggcagtgaag attcgtggcg aaagtaattt   3420
gttgcgaata ttcctgccgt tgttttatat aaacaatcag aataacaaag agttagcaat   3480
aggattttcg tcaaagtttt ccaggatttt ccttgtttcc agagcggatt ggtaagacaa   3540
ttagtgtttg aatttttcgg gtttagcgcg agtgggtaac gctcgtcaca tcgtggacat   3600
gtatgcagtg ctctggtagc tgtaaagcca ggggcggtag cgtgcattaa tacctctatt   3660
aatcaaactg agagccgctt atttcacagc atgctctgaa gtaatatgga ataataaagt   3720
gaagatactt gttactggtg gcgcaggatt tattggttct gctgtagttc gtcacattat   3780
aaataatacg caggatagtg ttgttaatgt cgataaatta acgtacgccg gaaacctgga   3840
gtcacttgct gatgtttctg actctaaacg ctatgttttt gaacatgcgg atatttgcga   3900
tgctgctgca atggcgcgga tttttgctca gcatcagccg gatgcagtga tgcacctggc   3960
tgctgaaagc catgtggatc gttcaattac aggccctgcg gcatttattg aaaccaatat   4020
tgttggtact tatgtccttt tggaagcggc tcgcaattac tggtctgctc ttgatggcga   4080
caagaaaaat agcttccgtt ttcatcatat ttctactgac gaagtctatg gtgatttgcc   4140
tcatcctgac gaagtaaata ataaagaaca attacccctc tttactgaga cgacagctta   4200
cgcgcctagt agtccttatt ccgcatcaaa agcatccagc gatcatttag tccgtgcgtg   4260
```

-continued

```
gaaacgtacc tatggtttac cgaccattgt gactaactgt tcgaataact acggtcctta   4320
tcactttccg gaaaaattga ttccactagt aattcttaat gctctggaag gtaaggcatt   4380
acctatttat ggcaaagggg atcaaattcg tgactggctg tatgttgaag atcatgcgcg   4440
tgcgttatat atcgtcgtaa ccgaaggtaa agcgggtgaa acttataaca ttggtggaca   4500
caacgaaaag aaaaacatcg atgtagtgct cactatttgt gatttgttgg atgagattgt   4560
accgaaagag aaatcttacc gcgagcaaat tacttatgtt gccgatcgcc cgggacacga   4620
tcgccgttat gcgattgatg cagagaagat tagccgcgaa ttgggctgga aaccgcagga   4680
aacgtttgag agcgggattc gtaaaacggt gggatggtac ctctccaata caaaatgggt   4740
tgataatgta aaaagtggtg cctatcaatc gtggattgaa cagaactatg agggccgcca   4800
gtaatgaata tcctcctttt cggcaaaaca gggcaggtag gttgggaact acagcgtgct   4860
ctggcacctc tgggtaattt gattgctctt gatgttcact ccactgatta ctgtggtgat   4920
tttagtaatc ctgaaggtgt agctgaaacc gtaagaagca ttcggcctga tattattgtc   4980
aacgcagccg ctcacaccgc agtagacaaa gcagaatcag aaccggagtt tgcacaatta   5040
cttaacgcga cgagtgtcga agcgatcgcg aaagcagcca atgaagtcgg cgcctgggtt   5100
attcactact ctactgacta cgtatttccg gggaccggtg aaataccatg gcaggaggcg   5160
gatgcaaccg caccgctaaa tgtttacggt gaaaccaagt tagctggaga aaaagcatta   5220
caagagcatt gtgcgaagca cctaattttc cgtacaagct gggtctatgc aggtaaagga   5280
aataacttcg ccaaaacgat gttgcgtctg ggaaaagagc gtgaagaatt agccgttatt   5340
aatgatcagt ttggtgcgcc aacaggtgct gaactgctgg ctgattgtac ggcacatgca   5400
attcgtgtgg cactgaataa accagaagtc gcaggcttgt accatctggt agccactggt   5460
accacaacct ggcacgatta tgctgcgctg gtttttgaag aggcacgaaa agcaggtatt   5520
ccccttgcac tcaacaagct caacgcagta ccaacaacag cttatcctac accagctcgt   5580
cgtccacata actctcgcct taatacagaa aaatttcagc aaaattttgc gcttgttttg   5640
cctgactggc aggttggcgt gaaacgaatg ctcaacgaat tatttacgac tacagcaatt   5700
taatagtttt tgcatcttgt tcgtgatgat ggagcaagat gaattaaaag gaatgatgta   5760
atgaaaacgc gtaaaggtat tattttagcg ggtggctctg gtactcgtct ttatcctgtg   5820
actatggctg tcagtaaaca gctattacct atttatgata agccgatgat ctattacccg   5880
ctctctacac tgatgttggc gggtattcgc gatattctga ttattagtac gccacaggat   5940
actcctcgtt ttcaacaact cctgggtgat ggtagccagt gggggttaaa tcttcagtac   6000
aaagtgcaac cgagtccaga tggtcttgcg caggcattta tcatcggtga agagtttatc   6060
ggtggtgatg attgtgctct ggttctcggt gataatatct tctacggtca tgatctgccg   6120
aagttaatgg atgtcgctgt caacaaagaa agtggtgcaa cggtatttgc ctatcacgtt   6180
aatgatcctg aacgctacgg tgttgttgag tttgataaaa acggtacggc aatcagcctg   6240
gaagaaaaac cgctacaacc aaaaagtaat tatgcggtaa ccgggcttta tttctatgat   6300
aacgacgttg tcgaaatggc gaaaaacctt aagccttctg cccgtggtga actggaaatt   6360
accgatatta accgtattta tatggagcag gggcgtttat ccgttgccat gatgggacgt   6420
ggttatgcat ggctggacac ggggacacat caaagtctta ttgaagcaag caacttcatt   6480
gcaacaattg aagagcgcca agggttaaag gtatcttgcc tggaagagat tgcttatcgt   6540
aaaggcttta ttgacgcaga gcaggttaat gtattagccg aaccgctaaa gaaaaatgct   6600
```

-continued

```
tatggtcagt atctgttgaa aatgattaaa ggttattaaa aatgaatgta attaaaactg   6660
aaattccaga tgtattaatt ttcgagccga aagtttttgg tgatgaacgt ggttttttta   6720
tggaaagctt taaccagaaa gttttcgaag aggctgtagg gcggaaggtt gaatttgttc   6780
aggataacca ttctaaatca actaagggtg tgttacgcgg actgcactat cagttggaac   6840
cttatgctca aggtaaatta gttcgttgtg ttgtcggtga agtttttgat gtagcagttg   6900
atattcgtaa atcgtcacct acatttggga aatggattgg ggtgaatttg tctgctgaga   6960
ataagcgtca gttgtggata cctgaaggat ttgcgcatgg atttttggtg ctgagtgaaa   7020
cggctgagtt tgtttataaa acaacaaact attacaatcc aagttttgaa aaaagtattt   7080
catactcaga tcctaccatt aaaattcagt ggcccaattt acaggatatg cattttaaat   7140
tatcaaataa ggatttgaat gctaagaact tttttaatga caatagttta atgcaatgaa   7200
gaaaaatata ttgctcttgt tcttagtaca tggggcaaat tatttgttcc cgtttatagt   7260
tcttccatat caaactcgaa tattaagcat cgagacattc gcagatgtag caaaaattca   7320
agccgctgtg atgcttttat ctttaatcgt aaattatgga tataacttat caagtacaag   7380
agctatagct agggccgtat ctcaagcaga aataaataag atctatagtg agactcttat   7440
tgtaaaatta ttattggcaa ccatttgtct tgcacttggt tgcgtacatt tgatgtatgt   7500
caaagagtac tcattgatat atccttttat aatcagttcg atatatcttt atggtagtgc   7560
attatttgct acttggttat tccaaggact tgagaaaatg aaagcggtcg ttatagcaac   7620
aacaatcgct aaactgactg gtgtgatact tacttttatt ttagttaagt ctccaaatga   7680
tatagttgca gctcttttta cacaaaacat tgggatgttt ataagtggta taatatctat   7740
ttatttggta aggaaaaaca aatatgcaac cgtaatatgt tttcgactta aaaatattat   7800
tgtaagctta aaagaagcgt ggccgttttt tttatcatta gctgcaacaa gtgtatatac   7860
atattttaat gtgattttat tatcttttta tgctggcgac tatgttgtgg caaattttaa   7920
tgctgctgat aaattaagaa tggctgctca agggttactt attccaatag gacaggctgt   7980
tttcccacga ttatctaaac tagagggcta tgaatatagt tctaaactta aaatttatgc   8040
aataaggtat gctatttttg gtgtttgcat tagtgcggga cttgtatttt taggtcccat   8100
gttaactact atttatttag gcaaagaata ttcgttgtca ggagaatatc ttcaaagtat   8160
gtttttacta cctgccacta tttcaatatc gactatactg agtcaatgga tgttgatacc   8220
tcaaggcaaa gaaaaaatat taagcagaat ctatattcta ggcgccattg tccatttatt   8280
atatgcattt cctttagttt actattatgg ggcttggggc atggtaatat caattttatt   8340
tactgaagtc ttaattgtat tatttatgct taaggctgtg aaatgactta ctttactggt   8400
tttattttaa tattgtttgc tattataatt aaaagattaa ctccaagtca aagcaagaaa   8460
aatattgtct taatagctaa tgcgttttgg ggaatattgt tggtaggtta tgctttcaat   8520
gaacaatatt tcgtaccatt aagtgcaaca accttgtttt ttatacttgc attcttattt   8580
ttctttagta tgacttatat tttaattgct aggagtggaa gggttgtttt ttctttcggt   8640
actggtttta tagaaagcaa atatatttac tggtttgctg ggatgattaa tattattagt   8700
atctgctttg gcattatcct tttatataat aatcattttt ctttaaaagt aatgagagaa   8760
ggaattttag atggttctat tagtgggttt ggattgggga taagtttgcc actttccttc   8820
tgctgtatgt atttagcaag acatgagaat aaaaaaaatt atttctattg ttttacacta   8880
ctttcattct tgcttgcggt gttatcaact tcaaagatct tcttaatatt attccttgta   8940
tatattgttg gaataaatag ttatgtaagc aaaaagaaat tgcttattta tggagtgttt   9000
```

```
gtatttggac tgttcgcttt atcaagtatt atcttgggta agttctcttc agaccctgaa   9060
ggcaagatta tttcagcaat atttgatacg ttaagggttt atcttttctc gggattggca   9120
gcctttaatc tttatgttga aaagaatgcc acgctccccg aaaatttact tttgtatcca   9180
tttaaggagg tttgggggac gacaaaagat attcccaaaa ctgatatttt gccttggatc   9240
aacattggtg tatgggacac gaatgtatat acagcttttg caccatggta tcagtcattg   9300
ggattatatg cagctataat tattggtatt ctcttagggt tttattacgg gatatggttt   9360
agctttcgtc aaaatttagc tgtgggtttt tatcaaacat ttttgtgttt tcctctttta   9420
atgttgtttt tccaggagca ttatttgttg tcatggaaaa tgcattttat ttattttta    9480
tgtgcaattt tattagcgat gagaaaagca ttagagtatg aataaatatt gtatcttagt   9540
actatttaat ccagatataa gtgtttttat tgataatgtc aaaaagattt tatctttgga   9600
tgtaagttta tttgtatatg acaattcagc aaataaacat gcattccttg ctctatcctc   9660
acaagagcaa acaaagataa attacttttc gatatgtgaa aatatcggat tgtcgaaagc   9720
ttataatgag acactaaggc atattcttga atttaataag aatgtgaaaa ataaaagcat   9780
taatgatagt gtgctttttc tcgaccaaga ctctgaagtt gatttaaatt ccatcaatat   9840
tttgtttgaa actatatcag cagcagagtc taatgtgatg atagtcgcgg ggaatcccat   9900
aaggagagat ggactaccgt atatagatta cccccacact gtaaacaatg taaaatttgt   9960
aattagtagt tatgctgtgt atcgcttaga cgcatttaga aacatcggct tgtttcaaga  10020
agattttttt atagatcata tcgatagtga tttttgttca aggctgataa aaagcaatta  10080
ccaaattctc cttagaaaag atgccttttt ttatcaacca ataggaataa aaccattcaa  10140
tctctgtggt agatatttat tccctatccc atcacaacac cgaacatatt ttcaaattag  10200
aaatgctttt ttaagttaca ggcgcaatgg tgttacattt aatttttat ttagggaaat   10260
tgtaaataga ttgattatga gtatattctc aggccttaac gagaaagact tattgaaacg  10320
attgcattta tatttaaaag gaataaaaga tggtcttaaa atgtaattct tggctagaag  10380
tgggggcgtt gtgattaaaa aaaaagtggc ggcgataatt ataacatata atccagatct  10440
aacaattctg cgagaaagtt atacgagtct atataagcaa gtcgataaaa taattcttat  10500
tgataacaac tctacaaact atcaagaact taagaagtta ttcgaaaaaa aagaaaaaat  10560
aaaaatagtg cccttgagtg ataatatagg actagcagca gctcaaaatt taggtttgaa  10620
cttagctatt aaaaataact atacttatgc tattttattc gatcaggata gcgtcttaca  10680
agacaatgga attaacagtt tctttttga atttgagaaa ttagttagtg aagaaaaatt   10740
aaatatagtt gccattgggc caagtttttt tgacgaaaag acaggaagac gctttcggcc  10800
tacaaaattt atcggtccct ttttatatcc ctttcgtaaa ataaccacaa aaaatcctct  10860
aacagaagtt gacttcttga ttgcttctgg ttgtttcata aaattggagt gtattaaatc  10920
agccggaatg atgactgaat cgttattcat cgattatatt gatgttgaat ggtcatatcg  10980
tatgcgttcg tatggctata agctatatat tcataatgat attcacatga gtcatttagt  11040
gggagaatct cgagttaatt taggattgaa aactatttct ttacatgggc cgctaagacg  11100
atattactta tttaggaatt atatttcaat tttaaaagtg agatatatac cgttaggata  11160
taaaatacgt gagggttttt ttaatatcgg aagattttg gtaagtatga ttataactaa   11220
aaatagaaaa actttaattt tatacactat aaaagcaatt aaggacggaa taaataatga  11280
aatggggaaa tataaaggct aacaacatat tatgaaaaaa ataatacata accaagtgtt  11340
```

gccgaaaatg tctgggattc agcaaatctc ttttgatatt ttgtcaggtc ttaaagacaa 11400
ggatgtacaa aaatttatat tatgcggttt accagatggc agttcagata atgaatttaa 11460
aaagaaattt actgatatag gtgttagggt tattacgata cctacattaa aacgaaatat 11520
cgggtggcat gactttcgat gtttcattga tttatacaat ttttttaaaa aagaaaaatt 11580
tgatatagtt catacaaact caactaagcc aggaataata gctagaatag ccgctagatt 11640
agccgggaca aaactcatta ttcacacagt acatggaatc gcatttcata gaaaagaaaa 11700
tactgtaagg aaaattttgc gactcttttt ggtagcatta atgtgagaat tctaattaat 11760
gggcatcatt tttcagctat ttcatttata aaataagtta tgaaaaaaat catcatatta 11820
ctaacgacat ttttcctgct ttcgggatgc actattccca gggcggtatt taaatccagc 11880
cttattaatc aggacgatcc tcgttataat ctggtcgaag tcacgccgac attaaaacta 11940
agcgctcccg atactgtgcc gaaaactatt gtcgatccgg tttttgccgc aaataactgg 12000
cactggacat ctttggctaa aggcgatgtg ctgcatatca ctattttatc ctcgggcggg 12060
gctggatatt tatccaataa cgcgagcggc gaccgtgcgg attttgaaaa tattcttgtg 12120
actgacagta ataccgttca ggtgccttat gccgggacaa tcccggtttc tggattggat 12180
gtgacgcaac tggctgatga gatcaaaaag cgactttcgc gcgttgtcct gaatcctcag 12240
gtgattgtga cacttaccgc ccgcaccgga gccatggtga cggtcgaggg cagcgggaaa 12300
acgggtcgat accctctcga acagagtatg aatcgtctga gtcatctttt ggcaacggca 12360
gtggcagtag aaaataccag cacagatatg atggaagttc acgtgacgcg ccagcagcat 12420
tatttcactg cgcgactgtc agatatttat cagtatcccg gattggatat tgccttacag 12480
ccggatgacc gtatcactct gcgtcaagtg accgagtatg ttaatgtgct cggcgcagca 12540
ggtgttcagg ggaaacatgc tctggttcag cgtcattcca gcgtcgtgga tgctttggcg 12600
ctcgcgaaag gattaaatga caatcttgcc gatccgcaag cgatttttct gtacaagcat 12660
aacgaagcgg aacaggcgaa acagcagatg cgtaagctga atatctatca tgtcgatatg 12720
agccaaccta actcggtgtt tttagcgcag gccatacgag tggacaacgg cgatgttatc 12780
tatatctcga acgcctcttt gactgatttc gctaaggtga aagccgcatt cgatagcttt 12840
ttgacccgcg gcactaattc tttctaatgt cgccatatga atattttgaa aaataattct 12900
tattatttta tgaaactcat taccgtctgt gagttaatta ttttattgat gtcacgcgat 12960
atcaaaacac gctataacgg taatttacta aactatatga tggtgctggc cgtaccactg 13020
gtatggatat ccattaccgt tatttctttt caatatttaa atcgctcggt gccaatatcc 13080
actgacgata tcagttttgt tattgcaggg atattaccgt atctgttatt tcgttatacc 13140
attaccgcaa c 13151

<210> SEQ ID NO 34
<211> LENGTH: 41
<212> TYPE: DNA
<213> ORGANISM: Artificial Sequence
<220> FEATURE:
<223> OTHER INFORMATION: Primer

<400> SEQUENCE: 34
gatcgggatc ctaatgaaaa tctgaccgga tgtaacggtt g 41

<210> SEQ ID NO 35
<211> LENGTH: 26
<212> TYPE: DNA
<213> ORGANISM: Artificial Sequence
<220> FEATURE:
<223> OTHER INFORMATION: Primer

<400> SEQUENCE: 35
gatcactcga gcgagaaatc ctagcg 26

<210> SEQ ID NO 36
<211> LENGTH: 26
<212> TYPE: DNA
<213> ORGANISM: Artificial Sequence
<220> FEATURE:
<223> OTHER INFORMATION: Primer

<400> SEQUENCE: 36
cccctcgcta ggatttctcg ctcgag 26

<210> SEQ ID NO 37
<211> LENGTH: 37
<212> TYPE: DNA
<213> ORGANISM: Artificial Sequence
<220> FEATURE:
<223> OTHER INFORMATION: Primer

<400> SEQUENCE: 37
gatcgggtac cttgttttct gagcgaatat atataag 37

<210> SEQ ID NO 38
<211> LENGTH: 84
<212> TYPE: DNA
<213> ORGANISM: Artificial Sequence
<220> FEATURE:
<223> OTHER INFORMATION: Primer

<400> SEQUENCE: 38
gatcggcggc cgcgacccaa aatggactat gacagaaaga tctgatattt ttcctcgcaa 60
aaatgaaaat atctcttgtc gttc 84

<210> SEQ ID NO 39
<211> LENGTH: 30
<212> TYPE: DNA
<213> ORGANISM: Artificial Sequence
<220> FEATURE:
<223> OTHER INFORMATION: Primer

<400> SEQUENCE: 39
gatcgggatc ctaaatatta aatggaagcc 30

<210> SEQ ID NO 40
<211> LENGTH: 36
<212> TYPE: DNA
<213> ORGANISM: Artificial Sequence
<220> FEATURE:
<223> OTHER INFORMATION: Primer

<400> SEQUENCE: 40
ataagaatgc ggccgcactg gctggaccca aaatgg 36

<210> SEQ ID NO 41
<211> LENGTH: 37
<212> TYPE: DNA
<213> ORGANISM: Artificial Sequence
<220> FEATURE:
<223> OTHER INFORMATION: Primer

<400> SEQUENCE: 41

-continued gatcaggatc ctcaatccag ggataattta ggcgaac 37

<210> SEQ ID NO 42
<211> LENGTH: 42
<212> TYPE: DNA
<213> ORGANISM: Artificial Sequence
<220> FEATURE:
<223> OTHER INFORMATION: Primer

<400> SEQUENCE: 42
gatcaggatc catcgattga gacttggatg atagacttca tg 42

<210> SEQ ID NO 43
<211> LENGTH: 50
<212> TYPE: DNA
<213> ORGANISM: Artificial Sequence
<220> FEATURE:
<223> OTHER INFORMATION: Primer

<400> SEQUENCE: 43
gatcaggatc cttatttttt tattaaatca agagttaacc atggagggag 50

<210> SEQ ID NO 44
<211> LENGTH: 32
<212> TYPE: DNA
<213> ORGANISM: Artificial Sequence
<220> FEATURE:
<223> OTHER INFORMATION: Primer

<400> SEQUENCE: 44
ttagaaagaa ttagtgccgc gggtcaaaaa gc 32

<210> SEQ ID NO 45
<211> LENGTH: 27
<212> TYPE: DNA
<213> ORGANISM: Artificial Sequence
<220> FEATURE:
<223> OTHER INFORMATION: Primer

<400> SEQUENCE: 45
ccgttcctca ttgatttgat tgctaac 27

<210> SEQ ID NO 46
<211> LENGTH: 25
<212> TYPE: DNA
<213> ORGANISM: Artificial Sequence
<220> FEATURE:
<223> OTHER INFORMATION: Primer

<400> SEQUENCE: 46
cggcaacata agtaatttgc tcacg 25

<210> SEQ ID NO 47
<211> LENGTH: 25
<212> TYPE: DNA
<213> ORGANISM: Artificial Sequence
<220> FEATURE:
<223> OTHER INFORMATION: Primer

<400> SEQUENCE: 47
cacgcaatat ttcaatgatg gcaac 25

<210> SEQ ID NO 48
<211> LENGTH: 33
<212> TYPE: DNA
<213> ORGANISM: Artificial Sequence -continued

```
<220> FEATURE:
<223> OTHER INFORMATION: Primer

<400> SEQUENCE: 48

gttgcggtaa tggtataacg aaataacaga tac                                33


<210> SEQ ID NO 49
<211> LENGTH: 31
<212> TYPE: DNA
<213> ORGANISM: Artificial Sequence
<220> FEATURE:
<223> OTHER INFORMATION: Primer

<400> SEQUENCE: 49

tatttattat gtgacgaaca acagcagaac c                                  31


<210> SEQ ID NO 50
<211> LENGTH: 188
<212> TYPE: DNA
<213> ORGANISM: Artificial Sequence
<220> FEATURE:
<223> OTHER INFORMATION: Primer

<400> SEQUENCE: 50

aattgactct gtggcatctt tacttccgtc atttatgaat acaatttcta cttcatatgg     60

cttcaactct tggaattcac gtaccgtttt atagaaaaca ggtatcgctt cttcttcatt    120

gaagacagga acgacaagag atattttcat atgtcctctc ctttcattat taataccctc    180

tagagttc                                                             188
```